US010478520B2

(12) United States Patent
Leimer et al.

(10) Patent No.: US 10,478,520 B2
(45) Date of Patent: Nov. 19, 2019

(54) USE OF SELF-ASSEMBLING POLYPEPTIDES AS TISSUE ADHESIVES

(71) Applicant: AMSilk GmbH, Planegg/Martinsried (DE)

(72) Inventors: Axel Leimer, Frankfurt am Main (DE); Lin Römer, Ottobrunn (DE); Nathalie Maksimovikj, München (DE)

(73) Assignee: Amsilk GmbH, Planegg/Martinsried (DE)

( * ) Notice: Subject to any disclaimer, the term of this patent is extended or adjusted under 35 U.S.C. 154(b) by 0 days.

(21) Appl. No.: 14/422,170

(22) PCT Filed: Aug. 14, 2013

(86) PCT No.: PCT/EP2013/067031
§ 371 (c)(1),
(2) Date: Feb. 17, 2015

(87) PCT Pub. No.: WO2014/027042
PCT Pub. Date: Feb. 20, 2014

(65) Prior Publication Data
US 2015/0328363 A1 Nov. 19, 2015

Related U.S. Application Data

(60) Provisional application No. 61/684,607, filed on Aug. 17, 2012.

(51) Int. Cl.
A61L 24/10 (2006.01)
A61F 2/02 (2006.01)
A61L 27/34 (2006.01)
A61L 27/54 (2006.01)

(52) U.S. Cl.
CPC ............ *A61L 24/10* (2013.01); *A61F 2/02* (2013.01); *A61L 24/102* (2013.01); *A61L 24/108* (2013.01); *A61L 27/34* (2013.01); *A61L 27/54* (2013.01); *A61F 2210/0076* (2013.01); *A61L 2300/252* (2013.01); *A61L 2300/606* (2013.01)

(58) Field of Classification Search
CPC ...................................................... A61L 24/10
See application file for complete search history.

(56) References Cited

U.S. PATENT DOCUMENTS

2008/0032934 A1* 2/2008 Ellis-Behnke .......... A61L 15/42 514/9.4
2011/0014263 A1* 1/2011 Altman .............. A61K 38/1767 424/423

FOREIGN PATENT DOCUMENTS

WO 2006/008163 A2 1/2006

OTHER PUBLICATIONS

Numata et al. Adv Drug Deliv Rev. Dec. 30, 2010; 62(15): 1497-1508.*
Wang (Nanolayer Biomaterial Coatings of Silk Fibroin for Controlled Release, J Control Release. Aug. 28, 2007; 121(3): 190-199.*
Altman, Silk-based biomaterials, Biomaterials 2003, 24:401-416 (Year: 2003).*
Horinek, Peptide adsorption on a hydrophobic surface results from an interplay of solvation, surface, and intrapeptide forces, PNAS 2008, 105:2842-2847 (Year: 2008).*
Kuhbier, Interactions between Spider Silk and Cells—NIH/3T3 Fibroblasts Seeded on Miniature Weaving Frames, PLoS One 2010, 5:1-9 (Year: 2010).*
Ruoslahti, "RGD and Other Recognition Sequences for Integrins," *Ann Rev Cell Dev Biol.*, vol. 12, pp. 697-715 (1996).
Spiess, et al., "Structural characterization and functionalization of engineered spider silk films," *Soft Matter*, vol. 6(1), pp. 4168-4174 (2010).
International Search Report for International Application No. PCT/EP2013/067031, dated May 26, 2014.

* cited by examiner

*Primary Examiner* — Karlheinz R. Skowronek
*Assistant Examiner* — Khalid Kader
(74) *Attorney, Agent, or Firm* — Kilpatrick Townsend & Stockton LLP

(57) ABSTRACT

The present invention relates to a self-assembling polypeptide for use as tissue adhesive. The present invention also relates to the use of a self-assembling polypeptide as tissue adhesive. Further, the invention is directed to the use of a self-assembling polypeptide to glue one or more cosmetic compounds on skin, mucosa, and/or hair. Furthermore, the invention is directed to a self-assembling polypeptide for use in gluing one or more pharmaceutical compounds on tissue, skin, mucosa, and/or hair.

Figure 1:
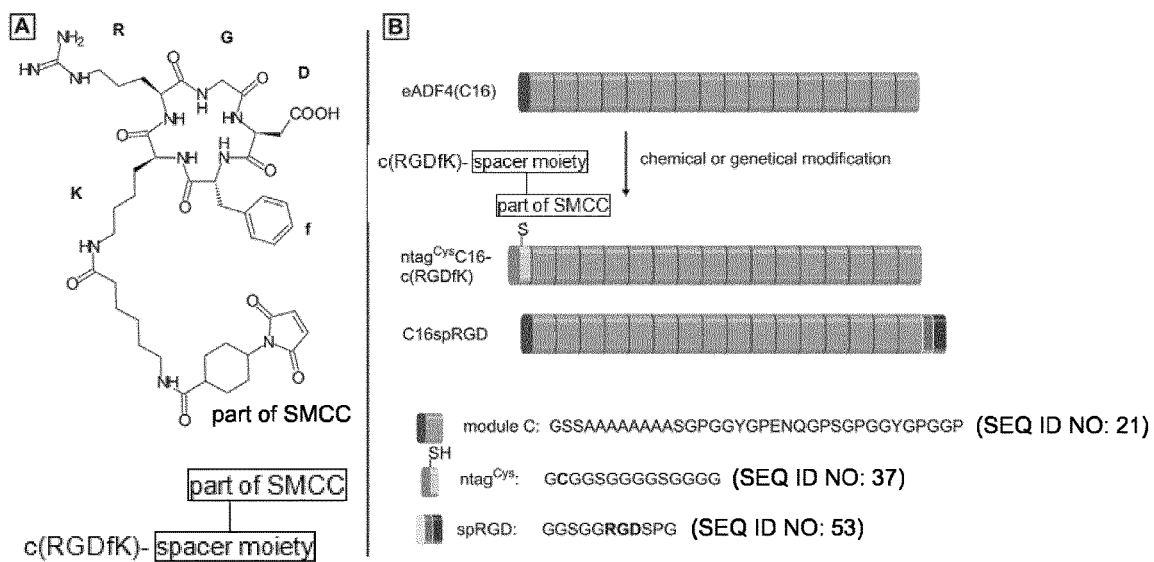

8 Claims, 7 Drawing Sheets
Specification includes a Sequence Listing.

A

B

C

D

A Top view:

B Side view:

C Side view:

A

B

C

```
                        SEQUENCE LISTING

<160> NUMBER OF SEQ ID NOS: 78

<210> SEQ ID NO 1
<211> LENGTH: 636
<212> TYPE: PRT
<213> ORGANISM: Araneus diadematus
<220> FEATURE:
<221> NAME/KEY: PEPTIDE
<222> LOCATION: (1)..(636)
<223> OTHER INFORMATION: ADF-3

<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gln Gly Pro
50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gln Gly Pro Tyr Gly Pro
            85                  90                  95

Gly Ser Ser Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
            115                 120                 125

Ala Ser Ala Ala Ala Ala Ala Gly Gly Tyr Gly Pro Gly Ser Gly
            130                 135                 140

Gln Gln Gly Pro Gly Gln Gln Gly Pro Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gly Pro Tyr
            180                 185                 190

Gly Pro Gly Ala Ser Ala Ala Ala Ala Ala Gly Gly Tyr Gly Pro
                195                 200                 205

Gly Ser Gly Gln Gln Gly Pro Gly Gln Gln Gly Pro Gly Gln Gln Gly
            210                 215                 220

Pro Gly Gly Gln Gly Pro Tyr Gly Pro Gly Ala Ser Ala Ala Ala
225                 230                 235                 240

Ala Ala Gly Gly Tyr Gly Pro Gly Tyr Gly Gln Gln Gly Pro Gly Gln
                245                 250                 255

Gln Gly Pro Gly Gly Gln Gly Pro Tyr Gly Pro Gly Ala Ser Ala Ala
                260                 265                 270

Ser Ala Ala Ser Gly Gly Tyr Gly Pro Gly Ser Gly Gln Gln Gly Pro
            275                 280                 285

Gly Gln Gln Gly Pro Gly Gly Gln Gly Pro Tyr Gly Pro Gly Ala Ser
```

```
                290              295              300
Ala Ala Ala Ala Ala Gly Gly Tyr Gly Pro Gly Ser Gly Gln Gln
305              310              315              320

Gly Pro Gly Gln Gln Gly Pro Gly Gln Gln Gly Pro Gly Gln Gln Gly
            325              330              335

Pro Gly Gly Gln Gly Pro Tyr Gly Pro Gly Ala Ser Ala Ala Ala Ala
            340              345              350

Ala Ala Gly Gly Tyr Gly Pro Gly Ser Gly Gln Gln Gly Pro Gly Gln
            355              360              365

Gln Gly Pro Gly Gln Gln Gly Pro Gly Gln Gln Gly Pro Gly Gln Gln
    370              375              380

Gly Pro Gly Gln Gln Gly Pro Gly Gln Gln Gly Pro Gly Gln Gln Gly
385              390              395              400

Pro Gly Gln Gln Gly Pro Gly Gln Gly Ala Tyr Gly Pro Gly Ala
            405              410              415

Ser Ala Ala Gly Ala Ala Gly Gly Tyr Gly Pro Gly Ser Gly Gln
    420              425              430

Gln Gly Pro Gly Gln Gln Gly Pro Gly Gln Gln Gly Pro Gly Gln Gln
    435              440              445

Gly Pro Gly Gln Gln Gly Pro Gly Gln Gln Gly Pro Gly Gln Gln Gly
    450              455              460

Pro Gly Gln Gln Gly Pro Tyr Gly Pro Gly Ala Ser Ala Ala Ala Ala
465              470              475              480

Ala Ala Gly Gly Tyr Gly Pro Gly Ser Gly Gln Gln Gly Pro Gly Gln
            485              490              495

Gln Gly Pro Gly Gln Gln Gly Pro Gly Gln Gly Pro Tyr Gly Pro
    500              505              510

Gly Ala Ala Ser Ala Ala Val Ser Val Gly Gly Tyr Gly Pro Gln Ser
    515              520              525

Ser Ser Val Pro Val Ala Ser Ala Val Ala Ser Arg Leu Ser Ser Pro
530              535              540

Ala Ala Ser Ser Arg Val Ser Ser Ala Val Ser Ser Leu Val Ser Ser
545              550              555              560

Gly Pro Thr Lys His Ala Ala Leu Ser Asn Thr Ile Ser Ser Val Val
            565              570              575

Ser Gln Val Ser Ala Ser Asn Pro Gly Leu Ser Gly Cys Asp Val Leu
        580              585              590

Val Gln Ala Leu Leu Glu Val Val Ser Ala Leu Val Ser Ile Leu Gly
        595              600              605

Ser Ser Ser Ile Gly Gln Ile Asn Tyr Gly Ala Ser Ala Gln Tyr Thr
610              615              620

Gln Met Val Gly Gln Ser Val Ala Gln Ala Leu Ala
625              630              635

<210> SEQ ID NO 2
<211> LENGTH: 410
<212> TYPE: PRT
<213> ORGANISM: Araneus diadematus
<220> FEATURE:
<221> NAME/KEY: PEPTIDE
<222> LOCATION: (1)..(410)
<223> OTHER INFORMATION: ADF-4

<400> SEQUENCE: 2

Ala Gly Ser Ser Ala Ala Ala Ala Ala Ala Ser Gly Ser Gly Gly
1               5                  10                  15
```

-continued

Tyr Gly Pro Glu Asn Gln Gly Pro Ser Gly Pro Val Ala Tyr Gly Pro
            20                  25                  30

Gly Gly Pro Val Ser Ser Ala Ala Ala Ala Ala Ala Gly Ser Gly
        35                  40                  45

Pro Gly Gly Tyr Gly Pro Glu Asn Gln Gly Pro Ser Gly Pro Gly Gly
50                  55                  60

Tyr Gly Pro Gly Ser Gly Ser Ser Ala Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
            100                 105                 110

Pro Gly Gly Pro Gly Ala Ser Ala Ala Ala Ala Ala Ala Ala Ala
            115                 120                 125

Ala Ser Gly Pro Gly Gly Tyr Gly Pro Gly Ser Gln Gly Pro Ser Gly
            130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
            180                 185                 190

Ala Ala Ala Ala Ala Gly Ser Gly Pro Gly Gly Tyr Gly Pro Glu
            195                 200                 205

Asn Gln Gly Pro Ser Gly Pro Gly Gly Tyr Gly Pro Gly Gly Ser Gly
            210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
            260                 265                 270

Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
        290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
            370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 5

```
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: consensus peptide motif
<220> FEATURE:
<221> NAME/KEY: MISC_FEATURE
<222> LOCATION: (4)..(5)
<223> OTHER INFORMATION: Xaa is any amino acid

<400> SEQUENCE: 3

Gly Pro Gly Xaa Xaa
1               5

<210> SEQ ID NO 4
<211> LENGTH: 5
<212> TYPE: PRT
<213> ORGANISM: Araneus diadematus
<220> FEATURE:
<221> NAME/KEY: VARIANT
<222> LOCATION: (4)..(4)
<223> OTHER INFORMATION: Gln may also be Ala, Ser, Gly, Tyr or Pro
<220> FEATURE:
<221> NAME/KEY: VARIANT
<222> LOCATION: (5)..(5)
<223> OTHER INFORMATION: Gln may also be Ala, Ser, Gly, Tyr or Pro

<400> SEQUENCE: 4

Gly Pro Gly Gln Gln
1               5

<210> SEQ ID NO 5
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 5

Gly Pro Gly Ala Ser
1               5

<210> SEQ ID NO 6
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-3)

<400> SEQUENCE: 6

Gly Pro Gly Ser Gly
1               5

<210> SEQ ID NO 7
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 7
```

```
Gly Pro Gly Gly Tyr
1               5

<210> SEQ ID NO 8
<211> LENGTH: 5
<212> TYPE: PRT
<213> ORGANISM: Araneus diadematus
<220> FEATURE:
<221> NAME/KEY: REPEAT
<222> LOCATION: (1)..(5)
<223> OTHER INFORMATION: peptide motif (ADF-4)

<400> SEQUENCE: 8

Gly Pro Gly Gly Pro
1               5

<210> SEQ ID NO 9
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 9

Gly Pro Gly Gly Ala
1               5

<210> SEQ ID NO 10
<211> LENGTH: 5
<212> TYPE: PRT
<213> ORGANISM: Unknown
<220> FEATURE:
<223> OTHER INFORMATION: phylum Arthropoda
<220> FEATURE:
<221> NAME/KEY: REPEAT
<222> LOCATION: (1)..(5)
<223> OTHER INFORMATION: peptide motif (resilin)

<400> SEQUENCE: 10

Gly Pro Gly Gly Gly
1               5

<210> SEQ ID NO 11
<211> LENGTH: 5
<212> TYPE: PRT
<213> ORGANISM: Nephila clavipes
<220> FEATURE:
<221> NAME/KEY: REPEAT
<222> LOCATION: (1)..(5)
<223> OTHER INFORMATION: peptide motif (flagelliform protein)

<400> SEQUENCE: 11

Gly Pro Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(5)
<223> OTHER INFORMATION: Ax peptide motif

<400> SEQUENCE: 12
```

```
Ala Ala Ala Ala Ala
1               5

<210> SEQ ID NO 13
<211> LENGTH: 6
<212> TYPE: PRT
<213> ORGANISM: Araneus diadematus
<220> FEATURE:
<221> NAME/KEY: REPEAT
<222> LOCATION: (1)..(6)
<223> OTHER INFORMATION: Ax peptide motif (ADF 3)

<400> SEQUENCE: 13

Ala Ala Ala Ala Ala Ala
1               5

<210> SEQ ID NO 14
<211> LENGTH: 7
<212> TYPE: PRT
<213> ORGANISM: Araneus diadematus
<220> FEATURE:
<221> NAME/KEY: REPEAT
<222> LOCATION: (1)..(7)
<223> OTHER INFORMATION: Ax peptide motif (ADF-4)

<400> SEQUENCE: 14

Ala Ala Ala Ala Ala Ala Ala
1               5

<210> SEQ ID NO 15
<211> LENGTH: 8
<212> TYPE: PRT
<213> ORGANISM: Araneus diadematus
<220> FEATURE:
<221> NAME/KEY: REPEAT
<222> LOCATION: (1)..(8)
<223> OTHER INFORMATION: Ax peptide motif (ADF-4)

<400> SEQUENCE: 15

Ala Ala Ala Ala Ala Ala Ala Ala
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: REPEAT
<222> LOCATION: (1)..(9)
<223> OTHER INFORMATION: Ax peptide motif

<400> SEQUENCE: 16

Ala Ala Ala Ala Ala Ala Ala Ala Ala
1               5

<210> SEQ ID NO 17
<211> LENGTH: 10
<212> TYPE: PRT
<213> ORGANISM: Araneus diadematus
<220> FEATURE:
<221> NAME/KEY: REPEAT
<222> LOCATION: (1)..(10)
<223> OTHER INFORMATION: Ax peptide motif (ADF-4)

<400> SEQUENCE: 17

Ala Ala Ala Ala Ala Ala Ala Ala Ala Ala
1               5                   10
```

```
<210> SEQ ID NO 18
<211> LENGTH: 9
<212> TYPE: PRT
<213> ORGANISM: Unknown
<220> FEATURE:
<223> OTHER INFORMATION: phylum Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 18

Gly Gly Arg Pro Ser Asp Thr Tyr Gly
1               5

<210> SEQ ID NO 19
<211> LENGTH: 9
<212> TYPE: PRT
<213> ORGANISM: Unknown
<220> FEATURE:
<223> OTHER INFORMATION: phylum Arthropoda
<220> FEATURE:
<221> NAME/KEY: REPEAT
<222> LOCATION: (1)..(9)
<223> OTHER INFORMATION: peptide motif (based on resilin)

<400> SEQUENCE: 19

Gly Gly Arg Pro Ser Ser Ser Tyr Gly
1               5

<210> SEQ ID NO 20
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module A (ADF-3)

<400> SEQUENCE: 20

Gly Pro Tyr Gly Pro Gly Ala Ser Ala Ala Ala Ala Ala Ala Gly Gly
1               5                   10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 21

Gly Ser Ser Ala Ala Ala Ala Ala Ala Ala Ala Ser Gly Pro Gly Gly
1               5                   10                  15

Tyr Gly Pro Glu Asn Gln Gly Pro Ser Gly Pro Gly Gly Tyr Gly Pro
            20                  25                  30

Gly Gly Pro
        35
```

```
<210> SEQ ID NO 22
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(20)
<223> OTHER INFORMATION: Module Q (ADF-3)

<400> SEQUENCE: 22

Gly Pro Gly Gln Gln Gly Pro Gly Gln Gln Gly Pro Gly Gln Gln Gly
1               5                   10                  15
Pro Gly Gln Gln
            20

<210> SEQ ID NO 23
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 23

Gly Gly Cys Gly
1

<210> SEQ ID NO 24
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 24

Gly Cys Gly Gly
1

<210> SEQ ID NO 25
<211> LENGTH: 34
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(34)
<223> OTHER INFORMATION: Module S (Resilin)

<400> SEQUENCE: 25

Pro Gly Ser Ser Ala Ala Ala Ala Ala Ala Ser Gly Pro Gly
1               5                   10                  15
Gln Gly Gln Gly Gln Gly Gln Gly Gln Gly Gly Arg Pro Ser Asp Thr
            20                  25                  30
Tyr Gly

<210> SEQ ID NO 26
<211> LENGTH: 39
<212> TYPE: PRT
```

```
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(39)
<223> OTHER INFORMATION: Module R (Resilin)

<400> SEQUENCE: 26

Ser Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Asn Gly Gly
                20                  25                  30

Arg Pro Ser Ser Ser Tyr Gly
        35

<210> SEQ ID NO 27
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 27

Gly Gly Lys Gly
1

<210> SEQ ID NO 28
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: peptide linker

<400> SEQUENCE: 28

Gly Lys Gly Gly
1

<210> SEQ ID NO 29
<211> LENGTH: 24
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(24)
<223> OTHER INFORMATION: Module Ac

<400> SEQUENCE: 29

Gly Pro Tyr Gly Pro Gly Ala Ser Ala Ala Ala Ala Ala Gly Gly
1               5                   10                  15

Tyr Gly Pro Gly Cys Gly Gln Gln
                20

<210> SEQ ID NO 30
<211> LENGTH: 24
<212> TYPE: PRT
<213> ORGANISM: Artificial Sequence
<220> FEATURE:
```

```
<223> OTHER INFORMATION: synthetic
<220> FEATURE:
<221> NAME/KEY: DOMAIN
<222> LOCATION: (1)..(24)
<223> OTHER INFORMATION: Module Ak

<400> SEQUENCE: 30

Gly Pro Tyr Gly Pro Gly Ala Ser Ala Ala Ala Ala Ala Gly Gly
1               5                   10                  15

Tyr Gly Pro Gly Lys Gly Gln Gln
            20

<210> SEQ ID NO 31
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 31

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35

<210> SEQ ID NO 32
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck1

<400> SEQUENCE: 32

Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Tyr Gly Pro
            20                  25                  30

Gly Gly Pro
        35

<210> SEQ ID NO 33
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ck2

<400> SEQUENCE: 33

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
            20                  25                  30
```

Gly Gly Pro
        35

<210> SEQ ID NO 34
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Ckc

<400> SEQUENCE: 34

Gly Ser Ser Ala Ala Ala Ala Ala Ala Ala Ser Gly Pro Gly Gly
1               5                   10                  15

Tyr Gly Pro Lys Asn Gln Gly Pro Cys Gly Pro Gly Gly Tyr Gly Pro
            20                  25                  30

Gly Gly Pro
        35

<210> SEQ ID NO 35
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG cys1

<400> SEQUENCE: 35

Gly Cys Gly Gly Gly Gly Gly Ser Gly Gly Gly Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG cys2

<400> SEQUENCE: 36

Gly Cys Gly Gly Gly Gly Gly Gly
1               5

<210> SEQ ID NO 37
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(14)
<223> OTHER INFORMATION: TAG cys3

<400> SEQUENCE: 37

Gly Cys Gly Gly Ser Gly Gly Gly Gly Ser Gly Gly Gly Gly
1               5                   10

-continued

```
<210> SEQ ID NO 38
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(13)
<223> OTHER INFORMATION: TAG lys1

<400> SEQUENCE: 38

Gly Lys Gly Gly Gly Gly Gly Gly Ser Gly Gly Gly Gly
1               5                   10

<210> SEQ ID NO 39
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: TAG lys2

<400> SEQUENCE: 39

Gly Lys Gly Gly Gly Gly Gly Gly
1               5

<210> SEQ ID NO 40
<211> LENGTH: 5
<212> TYPE: PRT
<213> ORGANISM: Unknown
<220> FEATURE:
<223> OTHER INFORMATION: phylum Arthropoda
<220> FEATURE:
<221> NAME/KEY: REPEAT
<222> LOCATION: (1)..(5)
<223> OTHER INFORMATION: peptide motif (resilin)

<400> SEQUENCE: 40

Gly Pro Gly Gln Gly
1               5

<210> SEQ ID NO 41
<211> LENGTH: 124
<212> TYPE: PRT
<213> ORGANISM: Artificial Sequence
<220> FEATURE:
<223> OTHER INFORMATION: synthetic based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 41

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
        35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80
```

```
Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
            100                 105                 110

Gln Met Val Gly Gln Ser Val Ala Gln Ala Leu Ala
        115                 120

<210> SEQ ID NO 42
<211> LENGTH: 109
<212> TYPE: PRT
<213> ORGANISM: Artificial Sequence
<220> FEATURE:
<223> OTHER INFORMATION: synthetic based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 42

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
        35                  40                  45

Leu Asn Ser Leu Val Ser Gln Ile Ser Ala Ser Asn Pro Gly Leu Ser
50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
            100                 105

<210> SEQ ID NO 43
<211> LENGTH: 747
<212> TYPE: PRT
<213> ORGANISM: Araneus diadematus
<220> FEATURE:
<221> NAME/KEY: PEPTIDE
<222> LOCATION: (1)..(747)
<223> OTHER INFORMATION: MaSp I

<400> SEQUENCE: 43

Gln Gly Ala Gly Ala Ala Ala Ala Ala Gly Gly Ala Gly Gln Gly
1               5                   10                  15

Gly Tyr Gly Gly Leu Gly Gly Gln Gly Ala Gly Gln Gly Gly Tyr Gly
            20                  25                  30

Gly Leu Gly Gly Gln Gly Ala Gly Gln Gly Ala Gly Ala Ala Ala Ala
        35                  40                  45

Ala Ala Ala Gly Gly Ala Gly Gln Gly Gly Tyr Gly Gly Leu Gly Ser
50                  55                  60

Gln Gly Ala Gly Arg Gly Gly Gln Gly Ala Gly Ala Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
        115                 120                 125
```

```
Gln Gly Ala Gly Arg Gly Gly Gln Gly Ala Ala Ala Ala Ala Gly
    130                 135                 140
Gly Ala Gly Gln Gly Gly Tyr Gly Gly Leu Gly Ser Gln Gly Ala Gly
145                 150                 155                 160
Arg Gly Gly Leu Gly Gly Gln Gly Ala Gly Ala Ala Ala Ala Ala
        165                 170                 175
Gly Gly Ala Gly Gln Gly Gly Tyr Gly Gly Leu Gly Gly Gln Gly Ala
            180                 185                 190
Gly Gln Gly Gly Tyr Gly Gly Leu Gly Ser Gln Gly Ala Gly Arg Gly
        195                 200                 205
Gly Leu Gly Gly Gln Gly Ala Gly Ala Ala Ala Ala Ala Ala Gly
    210                 215                 220
Gly Ala Gly Gln Gly Gly Leu Gly Gly Gln Gly Ala Gly Gln Gly Ala
225                 230                 235                 240
Gly Ala Ser Ala Ala Ala Ala Gly Gly Ala Gly Gln Gly Gly Tyr Gly
            245                 250                 255
Gly Leu Gly Ser Gln Gly Ala Gly Arg Gly Gly Glu Gly Ala Gly Ala
        260                 265                 270
Ala Ala Ala Ala Gly Gly Ala Gly Gln Gly Gly Tyr Gly Gly Leu
    275                 280                 285
Gly Gly Gln Gly Ala Gly Gln Gly Gly Tyr Gly Gly Leu Gly Ser Gln
    290                 295                 300
Gly Ala Gly Arg Gly Gly Leu Gly Gly Gln Gly Ala Gly Ala Ala Ala
305                 310                 315                 320
Ala Gly Gly Ala Gly Gln Gly Gly Leu Gly Gly Gln Gly Ala Gly Gln
            325                 330                 335
Gly Ala Gly Ala Ala Ala Ala Ala Gly Gly Ala Gly Gln Gly Gly
        340                 345                 350
Tyr Gly Gly Leu Gly Ser Gln Gly Ala Gly Arg Gly Gly Leu Gly Gly
        355                 360                 365
Gln Gly Ala Gly Ala Val Ala Ala Ala Ala Gly Gly Ala Gly Gln
    370                 375                 380
Gly Gly Tyr Gly Gly Leu Gly Ser Gln Gly Ala Gly Arg Gly Gly Gln
385                 390                 395                 400
Gly Ala Gly Ala Ala Ala Ala Ala Gly Gly Ala Gly Gln Arg Gly
            405                 410                 415
Tyr Gly Gly Leu Gly Asn Gln Gly Ala Gly Arg Gly Gly Leu Gly Gly
        420                 425                 430
Gln Gly Ala Gly Ala Ala Ala Ala Ala Gly Gly Ala Gly Gln
    435                 440                 445
Gly Gly Tyr Gly Gly Leu Gly Asn Gln Gly Ala Gly Arg Gly Gly Gln
    450                 455                 460
Gly Ala Ala Ala Ala Gly Gly Ala Gly Gln Gly Gly Tyr Gly Gly
465                 470                 475                 480
Leu Gly Ser Gln Gly Ala Gly Arg Gly Gly Gln Gly Ala Gly Ala Ala
            485                 490                 495
Ala Ala Ala Val Gly Ala Gly Gln Glu Gly Ile Arg Gly Gln Gly
        500                 505                 510
Ala Gly Gln Gly Gly Tyr Gly Gly Leu Gly Ser Gln Gly Ser Gly Arg
        515                 520                 525
Gly Gly Leu Gly Gly Gln Gly Ala Gly Ala Ala Ala Ala Ala Gly
    530                 535                 540
```

-continued

```
Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
                565                 570                 575

Gly Leu Gly Ser Gln Gly Ala Gly Arg Gly Gly Gln Gly Ala Gly Ala
                580                 585                 590

Ala Ala Ala Ala Gly Gly Ala Gly Gln Gly Gly Tyr Gly Gly Leu
            595                 600                 605

Gly Gly Gln Gly Val Gly Arg Gly Gly Leu Gly Gly Gln Gly Ala Gly
            610                 615                 620

Ala Ala Ala Gly Gly Ala Gly Gln Gly Gly Tyr Gly Gly Val Gly
625                 630                 635                 640

Ser Gly Ala Ser Ala Ala Ser Ala Ala Ala Ser Arg Leu Ser Ser Pro
                645                 650                 655

Gln Ala Ser Ser Arg Val Ser Ser Ala Val Ser Asn Leu Val Ala Ser
                660                 665                 670

Gly Pro Thr Asn Ser Ala Ala Leu Ser Ser Thr Ile Ser Asn Val Val
            675                 680                 685

Ser Gln Ile Gly Ala Ser Asn Pro Gly Leu Ser Gly Cys Asp Val Leu
690                 695                 700

Ile Gln Ala Leu Leu Glu Val Val Ser Ala Leu Ile Gln Ile Leu Gly
705                 710                 715                 720

Ser Ser Ser Ile Gly Gln Val Asn Tyr Gly Ser Ala Gly Gln Ala Thr
                725                 730                 735

Gln Ile Val Gly Gln Ser Val Tyr Gln Ala Leu
            740                 745

<210> SEQ ID NO 44
<211> LENGTH: 627
<212> TYPE: PRT
<213> ORGANISM: Araneus diadematus
<220> FEATURE:
<221> NAME/KEY: PEPTIDE
<222> LOCATION: (1)..(627)
<223> OTHER INFORMATION: MaSp II

<400> SEQUENCE: 44

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala
                20                  25                  30

Ala Ala Ala Ala Gly Pro Gly Gly Tyr Gly Pro Gly Gln Gln Gly Pro
            35                  40                  45

Gly Gly Tyr Gly Pro Gly Gln Gln Gly Pro Gly Arg Tyr Gly Pro Gly
        50                  55                  60

Gln Gln Gly Pro Ser Gly Pro Gly Ser Ala Ala Ala Ala Ala Gly
65                  70                  75                  80

Ser Gly Gln Gln Gly Pro Gly Gly Tyr Gly Pro Arg Gln Gln Gly Pro
                85                  90                  95

Gly Gly Tyr Gly Gln Gly Gln Gln Gly Pro Ser Gly Pro Gly Ser Ala
            100                 105                 110

Ala Ala Ser Ala Ala Ala Ser Ala Glu Ser Gly Gln Gln Gly Pro
        115                 120                 125

Gly Gly Tyr Gly Pro Gly Gln Gln Gly Pro Gly Gly Tyr Gly Pro Gly
        130                 135                 140

Gln Gln Gly Pro Gly Gly Tyr Gly Pro Gly Gln Gln Gly Pro Ser Gly
```

```
            145                 150                 155                 160
    Pro Gly Ser Ala Ala Ala Ala Ala Ala Ala Ser Gly Pro Gly Gln
                    165                 170                 175
    Gln Gly Pro Gly Gly Tyr Gly Pro Gly Gln Gln Gly Pro Gly Tyr
                    180                 185                 190
    Gly Pro Gly Gln Gln Gly Pro Ser Gly Pro Gly Ser Ala Ala Ala
                    195                 200                 205
    Ala Ala Ala Ala Ser Gly Pro Gly Gln Gln Gly Pro Gly Gly Tyr Gly
        210                 215                 220
    Pro Gly Gln Gln Gly Pro Gly Gly Tyr Gly Pro Gly Gln Gln Gly Leu
    225                 230                 235                 240
    Ser Gly Pro Gly Ser Ala Ala Ala Ala Ala Ala Gly Pro Gly Gln
                    245                 250                 255
    Gln Gly Pro Gly Gly Tyr Gly Pro Gly Gln Gln Gly Pro Ser Gly Pro
                    260                 265                 270
    Gly Ser Ala Ala Ala Ala Ala Ala Ala Gly Pro Gly Gly Tyr
        275                 280                 285
    Gly Pro Gly Gln Gln Gly Pro Gly Gly Tyr Gly Pro Gly Gln Gln Gly
        290                 295                 300
    Pro Ser Gly Ala Gly Ser Ala Ala Ala Ala Ala Ala Gly Pro Gly
    305                 310                 315                 320
    Gln Gln Gly Leu Gly Gly Tyr Gly Pro Gly Gln Gln Gly Pro Gly Gly
                    325                 330                 335
    Tyr Gly Pro Gly Gln Gln Gly Pro Gly Gly Tyr Gly Pro Gly Ser Ala
                    340                 345                 350
    Ser Ala Ala Ala Ala Ala Ala Gly Pro Gly Gln Gln Gly Pro Gly Gly
                    355                 360                 365
    Tyr Gly Pro Gly Gln Gln Gly Pro Ser Gly Pro Gly Ser Ala Ser Ala
                    370                 375                 380
    Ala Ala Ala Ala Ala Ala Gly Pro Gly Gly Tyr Gly Pro Gly Gln
    385                 390                 395                 400
    Gln Gly Pro Gly Gly Tyr Ala Pro Gly Gln Gln Gly Pro Ser Gly Pro
                    405                 410                 415
    Gly Ser Ala Ser Ala Ala Ala Ala Ala Ala Ala Gly Pro Gly Gly
                    420                 425                 430
    Tyr Gly Pro Gly Gln Gln Gly Pro Gly Gly Tyr Ala Pro Gly Gln Gln
                    435                 440                 445
    Gly Pro Ser Gly Pro Gly Ser Ala Ala Ala Ala Ala Ala Ala Ala
    450                 455                 460
    Gly Pro Gly Gly Tyr Gly Pro Ala Gln Gln Gly Pro Ser Pro Gly
    465                 470                 475                 480
    Ile Ala Ala Ser Ala Ser Ala Gly Pro Gly Gly Tyr Gly Pro Ala
                    485                 490                 495
    Gln Gln Gly Pro Ala Gly Tyr Gly Pro Gly Ser Ala Val Ala Ala Ser
                    500                 505                 510
    Ala Gly Ala Gly Ser Ala Gly Tyr Gly Pro Gly Ser Gln Ala Ser Ala
                    515                 520                 525
    Ala Ala Ser Arg Leu Ala Ser Pro Asp Ser Gly Ala Arg Val Ala Ser
    530                 535                 540
    Ala Val Ser Asn Leu Val Ser Gly Pro Thr Ser Ser Ala Ala Leu
    545                 550                 555                 560
    Ser Ser Val Ile Ser Asn Ala Val Ser Gln Ile Gly Ala Ser Asn Pro
                    565                 570                 575
```

```
Gly Leu Ser Gly Cys Asp Val Leu Ile Gln Ala Leu Glu Ile Val
            580                 585                 590

Ser Ala Cys Val Thr Ile Leu Ser Ser Ser Ile Gly Gln Val Asn
        595                 600                 605

Tyr Gly Ala Ala Ser Gln Phe Ala Gln Val Val Gly Gln Ser Val Leu
    610                 615                 620

Ser Ala Phe
625

<210> SEQ ID NO 45
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: PEPTIDE
<222> LOCATION: (1)..(5)
<223> OTHER INFORMATION: CAMP recognition sequence module

<400> SEQUENCE: 45

Ile Asp Ala Pro Ser
1               5

<210> SEQ ID NO 46
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(12)
<223> OTHER INFORMATION: CAMP recognition sequence module

<400> SEQUENCE: 46

His His Leu Gly Gly Ala Lys Gln Ala Gly Asp Val
1               5                   10

<210> SEQ ID NO 47
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(9)
<223> OTHER INFORMATION: CAMP recognition sequence module

<400> SEQUENCE: 47

Cys Asp Pro Gly Tyr Ile Gly Ser Arg
1               5

<210> SEQ ID NO 48
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(8)
<223> OTHER INFORMATION: CAMP recognition sequence module

<400> SEQUENCE: 48

Ala Glu Ile Asp Gly Ile Glu Leu
```

```
1               5

<210> SEQ ID NO 49
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: CAMP recognition sequence module

<400> SEQUENCE: 49

Gln Ile Asp Ser
1

<210> SEQ ID NO 50
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(4)
<223> OTHER INFORMATION: CAMP recognition sequence module

<400> SEQUENCE: 50

Arg Gly Asp Ser
1

<210> SEQ ID NO 51
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(5)
<223> OTHER INFORMATION: CAMP recognition sequence module

<400> SEQUENCE: 51

Gly Arg Gly Asp Ser
1               5

<210> SEQ ID NO 52
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(5)
<223> OTHER INFORMATION: CAMP recognition sequence module

<400> SEQUENCE: 52

Gly Arg Gly Asp Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: peptide
```

<222> LOCATION: (1)..(11)
<223> OTHER INFORMATION: CAMP recognition sequence module

<400> SEQUENCE: 53

Gly Gly Ser Gly Gly Arg Gly Asp Ser Pro Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(10)
<223> OTHER INFORMATION: CAMP recognition sequence module

<400> SEQUENCE: 54

Arg Gly Asp Ser Pro Ala Ser Ser Lys Pro
1               5                   10

<210> SEQ ID NO 55
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(14)
<223> OTHER INFORMATION: CAMP recognition sequence module

<400> SEQUENCE: 55

Cys Gly Gly Asn Gly Glu Pro Arg Gly Asp Tyr Arg Ala Tyr
1               5                   10

<210> SEQ ID NO 56
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 56

Gly Phe Pro Gly Glu Arg
1               5

<210> SEQ ID NO 57
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module Pro =
      Hydroxyproline (O)
<220> FEATURE:
<221> NAME/KEY: peptide
<222> LOCATION: (1)..(6)
<223> OTHER INFORMATION: CAMP recognition sequence module

```
<220> FEATURE:
<221> NAME/KEY: VARIANT
<222> LOCATION: (3)..(3)
<223> OTHER INFORMATION: Pro is Hydroxyproline (O)

<400> SEQUENCE: 57

Gly Leu Pro Gly Glu Arg
1               5

<210> SEQ ID NO 58
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module

<400> SEQUENCE: 58

Gly Ala Ser Gly Glu Arg
1               5

<210> SEQ ID NO 59
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 59

Gly Arg Pro Gly Glu Arg
1               5

<210> SEQ ID NO 60
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 60

Gly Met Pro Gly Glu Arg
1               5

<210> SEQ ID NO 61
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
```

```
<223> OTHER INFORMATION: CAMP recognition sequence module

<400> SEQUENCE: 61

Gly Leu Ser Gly Glu Arg
1               5

<210> SEQ ID NO 62
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 62

Gly Ala Pro Gly Glu Arg
1               5

<210> SEQ ID NO 63
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 63

Gly Phe Pro Gly Glu Lys
1               5

<210> SEQ ID NO 64
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 64

Gly Leu Pro Gly Glu Lys
1               5

<210> SEQ ID NO 65
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
```

```
<222> LOCATION: (1)..(6)
<223> OTHER INFORMATION: CAMP recognition sequence module

<400> SEQUENCE: 65

Gly Ala Ser Gly Glu Lys
1               5

<210> SEQ ID NO 66
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 66

Gly Arg Pro Gly Glu Lys
1               5

<210> SEQ ID NO 67
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 67

Gly Met Pro Gly Glu Lys
1               5

<210> SEQ ID NO 68
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module

<400> SEQUENCE: 68

Gly Leu Ser Gly Glu Lys
1               5

<210> SEQ ID NO 69
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
```

```
<221> NAME/KEY: VARIANT
<222> LOCATION: (3)..(3)
<223> OTHER INFORMATION: Pro is Hydroxyproline (O)

<400> SEQUENCE: 69

Gly Ala Pro Gly Glu Lys
1               5

<210> SEQ ID NO 70
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module
<220> FEATURE:
<221> NAME/KEY: VARIANT
<222> LOCATION: (3)..(3)
<223> OTHER INFORMATION: Pro is Hydroxyproline (O)

<400> SEQUENCE: 70

Gly Leu Pro Gly Glu Asn
1               5

<210> SEQ ID NO 71
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: peptide
<222> LOCATION: (1)..(6)
<223> OTHER INFORMATION: CAMP recognition sequence module

<400> SEQUENCE: 71

Gly Leu Lys Gly Glu Asn
1               5

<210> SEQ ID NO 72
<211> LENGTH: 39
<212> TYPE: DNA
<213> ORGANISM: Artificial Sequence
<220> FEATURE:
<223> OTHER INFORMATION: synthetic oligonucleotide for the RGD-tag

<400> SEQUENCE: 72
gatccatggg cggtcgtggt gactctccgg gttaatgaa                              39

<210> SEQ ID NO 73
<211> LENGTH: 39
<212> TYPE: DNA
<213> ORGANISM: Artificial Sequence
<220> FEATURE:
<223> OTHER INFORMATION: synthetic oligonucleotide for the RGD-tag

<400> SEQUENCE: 73
agctttcatt aacccggaga gtcaccacga ccgcccatg                              39

<210> SEQ ID NO 74
<211> LENGTH: 30
<212> TYPE: DNA
<213> ORGANISM: Artificial Sequence
<220> FEATURE:
<223> OTHER INFORMATION: synthetic oligonucleotide for the spacer
      sequence
```

<400> SEQUENCE: 74
gatccatggg cggtggctct ggttaatgaa 30

<210> SEQ ID NO 75
<211> LENGTH: 30
<212> TYPE: DNA
<213> ORGANISM: Artificial Sequence
<220> FEATURE:
<223> OTHER INFORMATION: synthetic oligonucleotide for the spacer sequence

<400> SEQUENCE: 75
agctttcatt aaccagagcc accgcccatg 30

<210> SEQ ID NO 76
<211> LENGTH: 136
<212> TYPE: PRT
<213> ORGANISM: Artificial Sequence
<220> FEATURE:
<223> OTHER INFORMATION: synthetic
<220> FEATURE:
<221> NAME/KEY: domain
<222> LOCATION: (1)..(136)
<223> OTHER INFORMATION: derived from Latrodectus hesperus

<400> SEQUENCE: 76

```
Met Gly Gln Ala Asn Thr Pro Trp Ser Ser Lys Ala Asn Ala Asp Ala
1               5                   10                  15

Phe Ile Asn Ser Phe Ile Ser Ala Ala Ser Asn Thr Gly Ser Phe Ser
            20                  25                  30

Gln Asp Gln Met Glu Asp Met Ser Leu Ile Gly Asn Thr Leu Met Ala
        35                  40                  45

Ala Met Asp Asn Met Gly Gly Arg Ile Thr Pro Ser Lys Leu Gln Ala
    50                  55                  60

Leu Asp Met Ala Phe Ala Ser Ser Val Ala Glu Ile Ala Ala Ser Glu
65                  70                  75                  80

Gly Gly Asp Leu Gly Val Thr Thr Asn Ala Ile Ala Asp Ala Leu Thr
                85                  90                  95

Ser Ala Phe Tyr Gln Thr Thr Gly Val Val Asn Ser Arg Phe Ile Ser
            100                 105                 110

Glu Ile Arg Ser Leu Ile Gly Met Phe Ala Gln Ala Ser Ala Asn Asp
        115                 120                 125

Val Tyr Ala Ser Ala Gly Ser Gly
    130                 135
```

<210> SEQ ID NO 77
<211> LENGTH: 137
<212> TYPE: PRT
<213> ORGANISM: Artificial Sequence
<220> FEATURE:
<223> OTHER INFORMATION: synthetic
<220> FEATURE:
<221> NAME/KEY: domain
<222> LOCATION: (1)..(137)
<223> OTHER INFORMATION: derived from Latrodectus hesperus

<400> SEQUENCE: 77

```
Met Gly Gln Ala Asn Thr Pro Trp Ser Ser Lys Glu Asn Ala Asp Ala
1               5                   10                  15

Phe Ile Gly Ala Phe Met Asn Ala Ala Ser Gln Ser Gly Ala Phe Ser
            20                  25                  30
```

-continued

```
Ser Asp Gln Ile Asp Asp Met Ser Val Ile Ser Asn Thr Leu Met Ala
        35                  40                  45

Ala Met Asp Asn Met Gly Gly Arg Ile Thr Gln Ser Lys Leu Gln Ala
 50                  55                  60

Leu Asp Met Ala Phe Ala Ser Ser Val Ala Glu Ile Ala Val Ala Asp
65                  70                  75                  80

Gly Gln Asn Val Gly Ala Ala Thr Asn Ala Ile Ser Asp Ala Leu Arg
                85                  90                  95

Ser Ala Phe Tyr Gln Thr Thr Gly Val Val Asn Asn Gln Phe Ile Thr
            100                 105                 110

Gly Ile Ser Ser Leu Ile Gly Met Phe Ala Gln Val Ser Gly Asn Glu
        115                 120                 125

Val Ser Tyr Ser Ser Ala Gly Ser Gly
    130                 135

<210> SEQ ID NO 78
<211> LENGTH: 587
<212> TYPE: PRT
<213> ORGANISM: Artificial Sequence
<220> FEATURE:
<223> OTHER INFORMATION: synthetic
<220> FEATURE:
<221> NAME/KEY: Protein
<222> LOCATION: (1)..(587)
<223> OTHER INFORMATION: C16spRGD with T7 TAG

<400> SEQUENCE: 78

Met Ala Ser Met Thr Gly Gly Gln Gln Met Gly Arg Gly Ser Met Gly
1               5                   10                  15

Ser Ser Ala Ala Ala Ala Ala Ala Ala Ser Gly Pro Gly Gly Tyr
            20                  25                  30

Gly Pro Glu Asn Gln Gly Pro Ser Gly Pro Gly Gly Tyr Gly Pro Gly
            35                  40                  45

Gly Pro Gly Ser Ser Ala Ala Ala Ala Ala Ala Ala Ser Gly Pro
        50                  55                  60

Gly Gly Tyr Gly Pro Glu Asn Gln Gly Pro Ser Gly Pro Gly Gly Tyr
65                  70                  75                  80

Gly Pro Gly Gly Pro Gly Ser Ser Ala Ala Ala Ala Ala Ala Ala
                85                  90                  95

Ser Gly Pro Gly Gly Tyr Gly Pro Glu Asn Gln Gly Pro Ser Gly Pro
            100                 105                 110

Gly Gly Tyr Gly Pro Gly Gly Pro Gly Ser Ser Ala Ala Ala Ala
        115                 120                 125

Ala Ala Ala Ser Gly Pro Gly Gly Tyr Gly Pro Glu Asn Gln Gly Pro
    130                 135                 140

Ser Gly Pro Gly Gly Tyr Gly Pro Gly Gly Pro Gly Ser Ser Ala Ala
145                 150                 155                 160

Ala Ala Ala Ala Ala Ser Gly Pro Gly Gly Tyr Gly Pro Glu Asn
                165                 170                 175

Gln Gly Pro Ser Gly Pro Gly Gly Tyr Gly Pro Gly Gly Pro Gly Ser
            180                 185                 190

Ser Ala Ala Ala Ala Ala Ala Ala Ser Gly Pro Gly Gly Tyr Gly
        195                 200                 205

Pro Glu Asn Gln Gly Pro Ser Gly Pro Gly Gly Tyr Gly Pro Gly Gly
    210                 215                 220

Pro Gly Ser Ser Ala Ala Ala Ala Ala Ala Ala Ser Gly Pro Gly
225                 230                 235                 240
```

```
Gly Tyr Gly Pro Glu Asn Gln Gly Pro Ser Gly Pro Gly Tyr Gly
                245                 250                 255
Pro Gly Gly Pro Gly Ser Ser Ala Ala Ala Ala Ala Ala Ala Ser
            260                 265                 270
Gly Pro Gly Gly Tyr Gly Pro Glu Asn Gln Gly Pro Ser Gly Pro Gly
        275                 280                 285
Gly Tyr Gly Pro Gly Gly Pro Gly Ser Ser Ala Ala Ala Ala Ala
    290                 295                 300
Ala Ala Ser Gly Pro Gly Gly Tyr Gly Pro Glu Asn Gln Gly Pro Ser
305                 310                 315                 320
Gly Pro Gly Gly Tyr Gly Pro Gly Gly Pro Gly Ser Ser Ala Ala Ala
                325                 330                 335
Ala Ala Ala Ala Ala Ser Gly Pro Gly Gly Tyr Gly Pro Glu Asn Gln
            340                 345                 350
Gly Pro Ser Gly Pro Gly Gly Tyr Gly Pro Gly Gly Pro Gly Ser Ser
            355                 360                 365
Ala Ala Ala Ala Ala Ala Ala Ser Gly Pro Gly Gly Tyr Gly Pro
    370                 375                 380
Glu Asn Gln Gly Pro Ser Gly Pro Gly Gly Tyr Gly Pro Gly Gly Pro
385                 390                 395                 400
Gly Ser Ser Ala Ala Ala Ala Ala Ala Ala Ser Gly Pro Gly Gly
            405                 410                 415
Tyr Gly Pro Glu Asn Gln Gly Pro Ser Gly Pro Gly Gly Tyr Gly Pro
            420                 425                 430
Gly Gly Pro Gly Ser Ser Ala Ala Ala Ala Ala Ala Ala Ser Gly
            435                 440                 445
Pro Gly Gly Tyr Gly Pro Glu Asn Gln Gly Pro Ser Gly Pro Gly Gly
    450                 455                 460
Tyr Gly Pro Gly Gly Pro Gly Ser Ser Ala Ala Ala Ala Ala Ala
465                 470                 475                 480
Ala Ser Gly Pro Gly Gly Tyr Gly Pro Glu Asn Gln Gly Pro Ser Gly
            485                 490                 495
Pro Gly Gly Tyr Gly Pro Gly Gly Pro Gly Ser Ser Ala Ala Ala Ala
        500                 505                 510
Ala Ala Ala Ser Gly Pro Gly Gly Tyr Gly Pro Glu Asn Gln Gly
    515                 520                 525
Pro Ser Gly Pro Gly Gly Tyr Gly Pro Gly Gly Pro Gly Ser Ser Ala
    530                 535                 540
Ala Ala Ala Ala Ala Ala Ser Gly Pro Gly Gly Tyr Gly Pro Glu
545                 550                 555                 560
Asn Gln Gly Pro Ser Gly Pro Gly Gly Tyr Gly Pro Gly Gly Pro Gly
                565                 570                 575
Gly Gly Ser Gly Gly Arg Gly Asp Ser Pro Gly
            580                 585
```

US 10,478,520 B2

USE OF SELF-ASSEMBLING POLYPEPTIDES AS TISSUE ADHESIVES

CROSS-REFERENCE TO RELATED APPLICATIONS

This application is the U.S. National Stage entry of PCT/EP2013/067031, filed Aug. 14, 2013, which claims priority to U.S. Provisional Application No. 61/684,607, filed Aug. 17, 2012.

REFERENCE TO SUBMISSION OF A SEQUENCE LISTING AS A TEXT FILE

The Sequence Listing written in file SUBSE-QTXT_95697-935988.txt, created on Jul. 31, 2015, 51,475 bytes, machine format IBM-PC, MS-Windows operating system, is hereby incorporated by reference in its entirety for all purposes.

The present invention relates to a self-assembling polypeptide for use as tissue adhesive. The present invention also relates to the use of a self-assembling polypeptide as tissue adhesive. Further, the invention is directed to the use of a self-assembling polypeptide to glue one or more cosmetic compounds on skin, mucosa, and/or hair. Furthermore, the invention is directed to a self-assembling polypeptide for use in gluing one or more pharmaceutical compounds on tissue, skin, mucosa, and/or hair.

BACKGROUND OF THE INVENTION

Tissue adhesives continue to evolve as an important technology for the physician, particularly surgeon. Years ago there was little routine use of these substances; however, in the past years there have been significant advances. It is becoming increasingly important for the physician, particularly surgeon, to be familiar with the indications and shortcomings of these compounds. Currently available tissue adhesives can be categorized as either fibrin tissue adhesives or acrylate-based tissue adhesives, e.g. cyanoacrylates. Although fibrin tissue adhesives and acrylate-based tissue adhesives, e.g. cyanoacrylates, are often discussed under the general topic of tissue adhesives, these two substances have different indications and mechanisms of action. Fibrin tissue adhesives use naturally occurring substrates that are part of normal endogenous clotting mechanisms. In contrast, the adhesion achieved by acrylate-based tissue adhesives, e.g. cyanoacrylates, is a result of synthetic compounds not naturally occurring in the human or animal body. These two types of adhesives also have different clinical indications. Fibrin tissue adhesives are typically applied below the dermis as a biologic hemostat or as a sealant for use with skin grafts and flaps. Acrylate-based tissue adhesives, e.g. cyanoacrylates, have been used most successfully at the level of the epidermis for superficial skin closure (see Toriumi D M, Raslan W F, Friedman M, et al. "Histotoxicity of cyanoacrylate tissue adhesives.", Arch Otolaryngol Head Neck Surg 1990; 116: 546-50).

The mechanism of action of fibrin tissue adhesives is best understood by reviewing basic blood coagulation physiology. During the normal clotting process, thrombin cleaves the large molecular weight protein fibrinogen into smaller fibrin subunits. These subunits then undergo both end-to-end and side-to-side polymerization. Factor XIII (plasma glutaminase), in the presence of calcium, enables the cross-linking of these polymerized subunits into a stable fibrin clot. Usually, fibrin tissue adhesives are packaged as two separate components that when mixed on the injured or surgical field simulate the interaction of these endogenous compounds and form the final fibrin clot. The first component is composed of fibrinogen, factor XIII, and calcium chloride, while the second component is made up of thrombin and an antifibrinolytic agent. Fibrin tissue adhesives have found several practical uses in surgery such as cardiac surgery, vascular surgery, plastic surgery, and reconstructive surgery as hemostatic agents as well as adhesives. They may also be used for the closure of both skin grafts and local skin flaps. There are a variety of applicators available to deliver fibrin tissue adhesives to the surgical field. The simplest is the sequential delivery of the first component and second component with two separate syringes. A dual-syringe applicator can also be used. Fibrin tissue adhesives have the advantage that they are biocompatible and biodegradable. They also show minimal tissue reactivity. However, fibrin tissue adhesives have the disadvantage that they are very expensive. In addition, fibrin tissue adhesives are not easy to handle. For example, the two components of the fibrin tissue adhesive have to be transported and stored deep frozen (e.g. at −20° C.). Thus, it is very important that the (distribution) cold chain is not interrupted. In addition, fibrin tissue adhesives have to be packed as two separate components to avoid fibrin clot formation before application. However, even after mixing, the processing time is very short before the fibrin clot formation is completed.

Acrylate-based tissue adhesives such as cyanoacrylates were first used in surgery 1959 when Coover (see Coover H W, Joyner F B, et al. "Chemistry and performance of cyanoacrylate adhesives." J Soc Plast Eng 1959; 15: 413-7) discovered their inherent adhesive properties. Cyanoacrylates include, but are not limited to, methyl-2-cyanoacrylate, buytl-2-cyanoacrylate, and octyl-2-cyanoacrylate. These compounds have their greatest utility in surgery such as facial plastic and reconstructive surgery as an alternative to traditional suture closure. They have also been used to close superficial wounds. In contrast to fibrin tissue adhesives, which rely on the interaction of endogenous compounds, the cyanoacrylate tissue adhesives are synthetic compounds that do not naturally occur in the human or animal body. One method of synthesizing an alkyl cyanoacrylate monomer is by reacting alkyl cyanoacetate with paraformaldehyde to form an intermediate compound. Heat applied to this intermediate compound causes depolymerization, resulting in an alkyl cyanoacrylate monomer liquid distillate (Toriumi D M, Raslan W F, Friedman M, et al. "Histotoxicity of cyanoacrylate tissue adhesives." Arch Otolaryngol Head Neck Surg 1990; 116: 546-50). Acrylate-based tissue adhesives, e.g. cyanoacrylates, are less expensive than fibroin tissue adhesives. However, acrylate-based tissue adhesives, e.g. cyanoacrylates, have been shown to be histotoxic when applied below the dermis. For example, when applied below the skin, cyanoacrylates may induce histotoxicity as a result of biodegradation of the polymer into cyanoacetate and formaldehyde. In addition, acrylate-based tissue adhesives have the disadvantage that they seal the treated area tight so that cells can not enter this area to reconnect the separated tissues.

Thus, there is a need for tissue adhesives which overcome the afore-mentioned problems.

The inventors of the present invention surprisingly found that self-assembling polypeptides, particularly silk polypeptides such as spider silk polypeptides, are ideal tissue adhesives as they meet the following criteria: sufficient binding strength, uncomplicated and time-independent application, tissue biocompatibility, no tissue reactivity such as allergic or inflammatory reactions, and reasonable costs. It is also remarkable that the adhesive effect is achieved without enzymatic and/or chemical reactions as described for fibrin-based and acrylate-based tissue adhesives. Further, when used as tissue adhesives, the self-assembling polypeptides, particularly silk polypeptides such as spider silk polypeptides, do not form an insurmountable barrier so that the glued sites can be entered and passed by cells to generate new tissue. Furthermore, the self-assembling polypeptides, particularly silk polypeptides such as spider silk polypeptides, have the advantage that they are flexible which reduces or even abolishes the tensile force acting on the affected area. In addition, in contrast to acrylate- and fibroin-based tissue adhesives, self-assembling polypeptides prevent or at least delay drying out of the glued tissues.

Systems for the recombinant production of self-assembling polypeptides, particularly silk polypeptides, e.g. spider silk polypeptides are known in the art. Particularly, systems for the recombinant production of spider silk polypeptides in *E. coli* have been developed in WO 2006/008163 and WO 2006/002827. As an example, it is referred to WO 2006/008163 (claiming priority of U.S. provisional application No. 60/590,196). In this expression system, single building blocks (=modules) can be varied freely and can thus be adapted to the requirements of the specific case. Modules of this type are disclosed also in Hummerich et al., "Primary structure elements of dragline silks and their contribution to protein solubility and assembly", 2004, Biochemistry 43, 13604-13612. Further modules are described in WO 2007/025719.

SUMMARY OF THE INVENTION

In a first aspect, the present invention relates to a self-assembling polypeptide for use as tissue adhesive.

In a second aspect, the present invention relates to the use of a self-assembling polypeptide as tissue adhesive.

In a third aspect, the present invention relates to the use of a self-assembling polypeptide to glue one or more cosmetic compounds on skin, mucosa, and/or hair.

In a fourth aspect, the present invention relates to a self-assembling polypeptide for use in gluing one or more pharmaceutical compounds on tissue, skin, mucosa, and/or hair.

In a fifth aspect, the present invention relates to an application combination comprising
i) a self-assembling polypeptide, and
ii) a factor enhancing self-assembly for use as tissue adhesive.

In a sixth aspect, the present invention relates to the use of an application combination comprising
i) a self-assembling polypeptide, and
ii) a factor enhancing self-assembly as tissue adhesive.

In a seventh aspect, the present invention relates to the use of an application combination comprising
i) a self-assembling polypeptide, and
ii) a factor enhancing self-assembly to glue one or more cosmetic compounds on skin, mucosa, and/or hair.

In an eight aspect, the present invention relates to an application combination comprising
i) a self-assembling polypeptide, and
ii) a factor enhancing self-assembly for use in gluing one or more pharmaceutical compounds on tissue, skin, mucosa, and/or hair.

In a ninth aspect, the present invention relates to a self-assembling polypeptide for use as organ protection and/or isolation material.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise herein, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS: needle, Matrix: Blosum62, Gap Open 10.0, Gap Extend 0.5.

Unless otherwise indicated, the terms "polypeptide" and "protein" are used interchangeably herein and mean any peptide-linked chain of amino acids, regardless of length or post-translational modification.

As mentioned above, the inventors of the present invention surprisingly found that self-assembling polypeptides, particularly silk polypeptides such as spider silk polypeptides, are ideal tissue adhesives as they meet the following criteria: sufficient binding strength, uncomplicated and time-independent application, tissue biocompatibility, no tissue reactivity such as allergic or inflammatory reactions, and reasonable costs. It is also remarkable that the adhesive effect is achieved without enzymatic and/or chemical reactions as described for fibrin and acrylate-based tissue adhesives. Further, when used as tissue adhesives, the self-assembling polypeptides, particularly silk polypeptides such as spider silk polypeptides, do not form an insurmountable barrier so that the glued sites can be entered and passed by cells to generate new tissue. Furthermore, the self-assembling polypeptides, particularly silk polypeptides such as spider silk polypeptides, have the advantage that they are flexible which reduces or even abolishes the tensile force acting on the effected area. In addition, in contrast to acrylate- and fibroin-based tissue adhesives, self-assembling polypeptides prevent or at least delay drying out of the glued tissues.

Thus, in a first aspect, the present invention relates to a self-assembling polypeptide for use as tissue adhesive.

The term "self-assembling polypeptide", as used herein, refers to a polypeptide which can perform self-assembly. "Self-assembly" is a term used to describe a process in which a disordered system of pre-existing polypeptides forms an organized structure or pattern as a consequence of specific, local interactions (e.g. van der Waals forces, hydrophobic interactions, hydrogen bonds, and/or salt-bridges, etc.) among the polypeptides themselves, without external direction or trigger although external factors might influence speed and nature of self-assembly. This particularly means that when two or more disordered and/or unfolded polypeptides are brought into contact, they interact with each other and consequently form a three dimensional structure. The change from a disordered system to an organised structure or pattern during self-assembly is characterized by a transition from a fluid state to a gelatinous and/or solid state and a corresponding increase in viscosity. The transition from a fluid state to a gelatinous state can be monitored, for example, by measurement of light scattering, rheology, or Circular Dichroism (CD). These techniques are known to the skilled person. The transition from a fluid state to a solid state can be monitored, for example, using optical methods.

Preferably, the self-assembling polypeptide is biodegradable, biocompatible, non-immunogenic and/or non-inflammatory.

The "tissue adhesive (also designated as tissue sealant or tissue glue)", as used herein, allows to connect, particularly reconnect, tissue layers, e.g. at least two tissue layers, with each other. Particularly, the tissue adhesive can provide a close, especially form-fit, connection between tissue layers, or in the event that the tissue layers are distant from each other, the tissue adhesive can fill the gap between the tissue layers, replace the missing tissue layers and/or bridge the missing tissue layers. Preferably, the gap has a size of no more than 1 cm, more preferably of no more than 0.75 cm, even more preferably of no more than 0.5 cm, most preferably of no more than 0.25 cm, e.g. of no more than 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm. Alternatively or additionally, the "tissue adhesive" allows to connect tissue layers to artificial surfaces, e.g. of medical devices such as implants, or allows to connect artificial surfaces, e.g. of medical devices such as implants, to tissue layers. Thereby, the medical devices such as implants can be embedded or incorporated in the tissue.

The tissue is preferably selected from the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, glands such as lymph and thyroid glands, eye, or pancreas, is, for example, comprised of multiple (different) tissues.

The inventors of the present invention further surprisingly found that the adhesive effect can be enhanced when a self-assembling polypeptide, particularly a silk polypeptide such as spider silk polypeptide, is used which further comprises a peptide having a cell adhesion mediating protein (CAMP) recognition sequence (e.g. RGD). This cell adhesion mediating protein (CAMP) recognition sequence (e.g. RGD) allows the binding of the peptide to CAMP proteins (e.g. integrins) which are present on the surface of cells and which are involved in the binding to other cells and/or to the extracellular matrix (ECM) in a process called cell adhesion. The surprising adhesive effect of RGD, as shown herein, is different to the effect known in the art that silk polypeptides containing RGD support cell growth. One remarkable difference between this embodiment of the invention and the state of the art is that the adhesive effect is exclusively based on a strong molecule interaction between the recognition sequence and CAMP and, thus, occurs within minutes or even faster whereas the cell adhesion effect previously described only occurs after days.

Thus, it is preferred that the self-assembling polypeptide further comprises at least one peptide, e.g. at least two peptides, particularly at least two identical peptides, which is (are) capable of enhancing the adhesive effect. The term "peptide" means a short polymer formed from the linking, in a defined order, of α-amino acids. The link between one amino acid residue and the next is called an amide bond or a peptide bond. Preferably, the at least one peptide, e.g. at least two peptides, particularly at least two identical peptides, which is (are) capable of enhancing the adhesive effect
  (i) is (are) composed of between 3 and 30 amino acids, more preferably between 3 and 20 amino acids, and even more preferably between 3 and 15 amino acids, e.g. 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and/or
  (ii) is (are) (a) linear peptide(s), cyclic peptide(s), or peptide analog(s).

It is particularly preferred that the at least one peptide, e.g. at least two peptides, particularly at least two identical peptides, is (are) capable of enhancing the adhesive effect by at least 10%, more preferably by at least 20%, even more preferably by at least 40%, and most preferably by at least 60% or 80%, e.g. by at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%. Tests to measure the adhesive effect are described in the experimental section.

It is more preferred that the at least one peptide, e.g. at least two peptides, particularly at least two identical peptides, which is (are) capable of enhancing the adhesive effect is (are) attached to the self-assembling polypeptide, e.g. to the N- and/or C-terminus of the self-assembling polypeptide.

Said attachment may occur via genetical fusion. For genetical fusion, for example, the peptide which is capable of enhancing the adhesive effect may be fused by genetic engineering to the self-assembling polypeptide.

Alternatively or additionally, said attachment may occur via chemical coupling, for example, via a covalent bond such as a peptide bond and/or non-peptide bond, e.g. disulfide-bond. Said attachment may be directly or indirectly, e.g. via a linker. The term "linker", as used herein, refers to a moiety that connects the peptide which is capable of enhancing the adhesive effect with the self-assembling polypeptide covalently. It may be comprised at the N- and/or C-terminus of the self-assembling polypeptide. In this case, the linker may be designated as TAG. Preferred herein are peptide linkers. This means that the peptide linker is an amino acid sequence that connects the peptide which is capable of enhancing the adhesive effect with the self-assembling polypeptide. The peptide linker may be connected to the peptide by a peptide or non-peptide bond and to the self-assembling polypeptide by a peptide or non-peptide bond. For example, the peptide linker may be connected (i) to the peptide and to the self-assembling polypeptide via a peptide bond, (ii) to the peptide and to the self-assembling polypeptide via a non-peptide bond, (iii) to the peptide via a non-peptide bond and to the self-assembling polypeptide via a peptide-bond, or (iv) to the peptide via a peptide-bond and to the self-assembling polypeptide via a non-peptide bond. When the peptide linker is connected to the peptide via a non-peptide bond, this may be done via a thiol-group of a cysteine (C) of the linker. In addition, when the peptide linker is connected to the peptide via a peptide-bond, this may be done via a ε-group of a lysine (K) residue of the linker. Typically, a peptide linker has a length of between 1 and 20 amino acids, e.g. 1, 2, 3, 4, 5, 6, 7, 8, 9, 10, 11, 12, 13, 14, 15, 16, 17, 18, 19, or 20 amino acids. It is preferred that said linker comprises at least one cysteine (C) or lysine (K) residue. It is also preferred that the amino sequence of the peptide linker is not immunogenic to human beings. For example, a linker having at least the amino acid sequence GC, CG, GK or KG, or having at least the amino acid sequence GCG, GKG or any other peptide linker, e.g. GGCG (SEQ ID NO: 23), GCGG (SEQ ID NO: 24), GGKG (SEQ ID NO: 27), or GKGG (SEQ ID NO: 28), can be used in the present invention. Also other linkers for the chemical coupling of two protein monomers, are known in the art and can be used.

Particularly, the at least one peptide, e.g. at least two peptides, particularly at least two identical peptides, can be attached to the self-assembling polypeptide or linker via a side group of an amino acid, e.g. via a thiol-group, amino-group, or carboxy-group, of said linker or self-assembling polypeptide. The attachment of the at least one peptide, e.g. at least two peptides, particularly at least two identical peptides, to the self-assembling polypeptide or linker can also take place via a reactive group (e.g. SMCC, Succinimidyl-4-(N-maleimidomethyl)cyclohexane-1-carboxylate) optionally comprising a spacer moiety, such as an amino-carboxylic acid, in particular an amino-carboxylic acid which comprises the amino group at the ω-C-atom. The reactive group optionally comprising a spacer moiety may be coupled to the peptide, linker and/or self-assembling polypeptide. Preferably, the amino-carboxylic acid comprises between 2 to 10 C-atoms, and more preferably between 4, 6, and 8 C-atoms, e.g. 2, 3, 4, 5, 6, 7, 8, 9, or 10 C-atoms. More preferably, the amino-carboxylic acid is 6-amino-hexanoic acid. The term "reactive group", as used herein, means any group which is capable of forming a covalent bond to a side group of an amino acid. Beyond that, the skilled person knows how to connect the peptide with the self-assembling polypeptide.

In a preferred embodiment, the self-assembling polypeptide further comprises an amino terminal and/or a carboxy terminal TAG selected from the group consisting of
i) $TAG^{CYS1}$ consisting of the amino acid sequence GCGGGGGGSGGGG (SEQ ID NO: 35),
ii) $TAG^{CYS2}$ consisting of the amino acid sequence GCGGGGGG (SEQ ID NO: 36),
iii) $TAG^{CYS3}$ consisting of the amino acid sequence GCGGSGGGSGGGG (SEQ ID NO: 37),
iv) $TAG^{LYS1}$ consisting of the amino acid sequence GKGGGGGGSGGGG (SEQ ID NO: 38), and
v) $TAG^{LYS2}$ consisting of the amino acid sequence GKGGGGGG (SEQ ID NO: 39).

Said TAG is preferably attached (e.g. covalently linked or coupled) to the N- and/or C-terminus of the self-assembling polypeptide. The thiol-group of the cysteine residue comprised in the above TAGs allows the coupling of the peptide to said TAGs and, thus, also to the self-assembling polypeptide. In a more preferred embodiment, the peptide which is capable of enhancing the adhesive effect is covalently coupled to the thiol-group of a cysteine residue of $TAG^{CYS3}$.

Preferably, the adhesive effect is mediated via binding of the peptide to a cell adhesion mediating protein (CAMP). Said binding is preferably a non-covalent binding, particularly a non-covalent and reversible binding. The term "cell adhesion mediating protein (CAMP)", as used herein, refers to a protein located on the cell surface involved in the binding with other cells and/or with the extracellular matrix (ECM) in a process called cell adhesion. Essentially, CAMPs help cells to stick to each other and to their surroundings. These proteins are typically transmembrane receptors and are composed of three domains: an intracellular domain that interacts with the cytoskeleton, a transmembrane domain, and an extracellular domain that interacts either with other CAMPs of the same kind (homophilic binding), or with other CAMPs or the extracellular matrix (heterophilic binding). Particularly the extracellular domain comprised in the CAMPs interacts with CAMP recognition sequences.

The term "cell adhesion", as used herein, refers to a mechanism which allows the coupling of cells to adjacent cells (cell-cell adhesion) and/or the coupling of cells to the surrounding ECM (cell-ECM adhesion). Cell adhesion is the basis for the establishment and development of multicellular organisms. Cell adhesion processes are important for cell morphogenesis and the development of tissues. Therefore, cell adhesion plays an important role during proliferation, migration, and/or differentiation. Particularly, the cell adhesion mechanism is a cellular process which includes wound healing, homeostasis, tumor growth, and metastasis.

Most of the CAMPs belong to three protein families: the integrins, the cadherins, and the selectins. Thus, in preferred embodiments of the present invention, the CAMP is an integrin, a selectin, or a cadherin.

The term "integrins", as used herein, refers to a family of receptors that mediate the attachment between a cell and the tissue that surrounds it, such as other cells and/or the extracellular matrix (ECM). Integrins are calcium dependent. They are a family of heterophilic CAMPs. Integrins are heterodimers containing two distinct chains, called α (alpha) and β (beta) subunits. The different combinations of α and β subunits result in a number of functional integrins. Integrin α/β heterodimers can be grouped into three subfamilies, namely ß1-integrin, ß2-integrin, and αv-integrin. Thus, for example, the integrin is selected from the group consisting of ß1-integrin, ß2-integrin, and αv-integrin.

The term "selectins (or cluster of differentiation 62/CD62 proteins)", as used herein, refers to a family of single-chain transmembrane glycoproteins that share similar properties to C-type lectins due to a related amino terminus and calcium-dependent binding. Selectins bind to sugar moieties and so are considered to be a type of lectin cell adhesion proteins that bind sugar polymers. They are a family of heterophilic CAMPs. Preferably, the selectin is selected from the group consisting of L-selectin, P-selectin, and E-selectin.

The term "cadherins (or calcium-dependent adhesion proteins)", as used herein, refers to a class of type-1 transmembrane proteins. They are a family of homophilic CAMPs. Cadherins play important roles in cell adhesion ensuring that cells within tissues are bound together. They are dependent on calcium ($Ca^{2+}$) ions to function, hence their name. Preferably, cadherins are selected from the group consisting of classical cadherins, desmosomal cadherins, protocadherins, and unconventional/ungrouped cadherins. It is particularly preferred that the (classical) cadherin is selected from the group consisting of E-cadherin, N-cadherin, and P-cadherin.

More preferably, the peptide which is capable of enhancing the adhesive effect comprises at least one CAMP recognition sequence, e.g. at least one, two, three, or four CAMP recognition sequence(s). The at least one CAMP recognition sequence particularly allows the binding of the peptide which is capable of enhancing the adhesive effect to the CAMP. Thus, in preferred embodiments of the invention, the adhesive effect is mediated via binding of the peptide by its at least one CAMP recognition sequence to the CAMP. Said binding is preferably a non-covalent binding, particularly a non-covalent and reversible binding.

CAMP recognition sequences occur naturally in CAMP-binding proteins, e.g. in fibronectin, fibrinogen, or vitronectin. Examples of CAMP-binding proteins, their CAMP recognition sequences and CAMPs to which they bind are listed in Table 1.

CAMP recognition sequences which may be used in the present invention comprise or consists of a RGD-containing module or a non-RGD-containing module.

The RGD sequence is the cell attachment site of a large number of extracellular matrix (EM), blood, and cell surface proteins. Particularly, integrins recognize this sequence (see, for example, Ruoslahti, E. "RGD and other recognition sequences for integrins.", Annual Review of Cell and Developmental Biology, 1996, Vol. 12, pages 697-715.). The RGD sequence is, for example, naturally comprised in the bone sialoprotein, in collagen, decorsin, disintegrin, fibronectin, fibrinogen, fibrillin, prothrombin, thrombospondin, tenascin, vitronectin, or in the von Willebrand factor. Proteins with a CAMP recognition sequence which differs from RGD are, for example, collagen, cytotactin/tenascin-C, epiligrin, factor X, α-Chain of fibrinogen, γ-Chain of fibrinogen, invasin, laminin, matrix metalloproteinase-2, neutrophil inhibitory factor, osteopontin, plasminogen, spectrin, tenascin, or VCAM-1.

The GER, GEN, and GEK sequences are, for example, cell attachment sites which are naturally comprised in collagens. Said sequences are particularly used by collagen-binding integrins (see, for example, Raynal, N. et al., "Use of synthetic peptides to locate novel integrin α2β1-binding motifs in human collagen III.", Journal of biological chemistry, 2006, Vol. 281, pages 3821-3831.) Further, the IDAPS sequence is, for example, a cell attachment site which is naturally comprised in fibronectin and the GPR and HHLG-GAKQAGDV sequences are, for example, cell attachment sites which are naturally comprised in fibrinogen. Particularly, integrins recognize these sequences. Furthermore, the CDPGYIGSR sequence is, for example, a cell attachment site which is naturally comprised in laminin, the AEIDGIEL sequence is, for example, a cell attachment site which is naturally comprised in tenascin, the QIDS sequence is, for example, a cell attachment site which is naturally comprised in VCAM-1, and the LDT sequence is, for example, a cell attachment site which is naturally comprised in MAdCAM-1.

TABLE 1

Examples of CAMP-binding proteins, their CAMP recognition sequences and CAMPs to which they bind.

| CAMP-binding protein | CAMP | CAMP recognition sequence |
| --- | --- | --- |
| Bone sialoprotein | Integrin | RGD |
| Collagen | Integrin | RGD |
| | | GFOGER |
| | | (O=Hydroxyproline) |
| Decorsin | Integrin | RGD |
| Disintegrin | Integrin | RGD |
| Fibronectin | Integrin | RGD |
| | | IDAPS |
| Fibrinogen | Integrin | RGD |
| α-Chain of fibrinogen | Integrin | GPR |
| γ-Chain of fibrinogen | Integrin | HHLGGAKQAGDV |
| Laminin | Integrin | CDPGYIGSR |
| MAdCAM-1 | Integrin | LDT |
| Prothrombin | Integrin | RGD |
| Thrombospondin | Integrin | RGD |
| Tenascin | Integrin | RGD |
| | | AEIDGIEL |
| VCAM-1 | Integrin | QIDS |
| Vitronectin | Integrin | RGD |
| von Willebrand factor | Integrin | RGD |

In preferred embodiments, the CAMP recognition sequence comprises a module containing or consisting of RGD, GER, GEK, GEN, IDAPS (SEQ ID NO: 45) or variants thereof, GPR, HHLGGAKQAGDV (SEQ ID NO: 46) or variants thereof, CDPGYIGSR (SEQ ID NO: 47) or variants thereof, AEIDGIEL (SEQ ID NO: 48) or variants thereof, QIDS (SEQ ID NO: 49), or LTD. In more preferred embodiments, the CAMP recognition sequence comprises a module containing or consisting of RGD.

As mentioned above, it is preferred that the peptide which is capable of enhancing the adhesive effect comprises at least one CAMP recognition sequence, e.g. at least one, two, three, or four CAMP recognition sequence(s). Preferably, said CAMP recognition sequence comprises a module containing or consisting of RGD, GER, GEK, GEN, IDAPS (SEQ ID NO: 45) or variants thereof, GPR, HHLG-GAKQAGDV (SEQ ID NO: 46) or variants thereof, CDP-GYIGSR (SEQ ID NO: 47) or variants thereof, AEIDGIEL (SEQ ID NO: 48) or variants thereof, QIDS (SEQ ID NO: 49), or LTD. Thus, for example, the peptide may comprise (i) one, two, three, or four RGD-containing modules, (ii) one, two, three, or four GER-containing modules, (iii) one, two, three, or four GEK-containing modules, (iv) one, two, three, or four GEN-containing modules, (v) one module containing RGD and one module containing GER, (vi) one module containing RGD and one module containing GEK, (vii) one module containing RGD and one module containing GEN, (viii) one module containing GER and one module containing GEK, (ix) one module containing GER and one module containing GEN, (x) one module containing GEK and one module containing GEN, (xi) one module containing RGD, one module containing GER, and one module containing GEK, (xii) one module containing RGD, one module containing GER, and one module containing GEN, (xiii) one module containing RGD, one module containing GEK, and one module containing GEN, (xiv), one module containing GER, one module containing GEK, and one module containing GEN, and (xv) one module containing RGD, one module containing GER, one module containing GEK, and one module containing GEN.

The above mentioned variants, i.e. IDAPS, HHLG-GAKQAGDV, CDPGYIGSR, or AEIDGIEL variants, differ from the IDAPS, HHLGGAKQAGDV, CDPGYIGSR, or AEIDGIEL references (wild-types) from which they are derived by up to 1, 2, 3, or 4 amino acid changes in the amino acid sequence (i.e. substitutions, additions, insertions, deletions, N-terminal truncations and/or C-terminal truncations). Such variants can alternatively or additionally be characterised by a certain degree of sequence identity to the references (wild-types) from which they are derived. Thus, the IDAPS, HHLGGAKQAGDV, CDPGYIGSR, or AEIDGIEL variants have a sequence identity of at least 85%, 86%, 87%, 88%, 89%, 90%, 91%, 92%, 93%, 94%, 95%, 96%, 97%, 98%, or 99% to the respective IDAPS, HHLGGAKQAGDV, CDPGYIGSR, or AEIDGIEL references (wild-types). It is particularly preferred that the sequence identity is at least 85% over the whole length, is at least 85% over the whole length, is at least 90% over the whole length, is at least 95% over the whole length, is at least 98% over the whole length, or is at least 99% over the whole length of the respective IDAPS, HHLG-GAKQAGDV, CDPGYIGSR, or AEIDGIEL references (wild-types).

Fragments (or deletion variants) of IDAPS, HHLG-GAKQAGDV, CDPGYIGSR, or AEIDGIEL have preferably a deletion of up to 1 or 2 amino acids at its N-terminus and/or at its C-terminus. The deletion can also be internally.

Additionally, the IDAPS, HHLGGAKQAGDV, CDPGYIGSR, or AEIDGIEL variants or fragments are only regarded as a IDAPS, HHLGGAKQAGDV, CDPGYIGSR, or AEIDGIEL variants or fragments within the context of the present invention, if the modifications with respect to the amino acid sequence on which the variants or fragments are based do not negatively affect the ability of the peptide to bind to the CAMP. The skilled person can readily assess whether the peptide comprising a modified CAMP recognition sequence is still able to bind to the CAMP, e.g. by performing protein binding studies. For example, the Isothermal Titration Calorimetry (ITC) is a powerful analytical tool which measures the binding affinity and thermodynamics between any two biomolecules. In addition, the Surface Plasmon Resonance (SPR) based technology can be used for studying biomolecular interactions in real time.

In even more preferred embodiments, the CAMP recognition sequence comprises a module containing a linear or cyclic RGD. A CAMP recognition sequence which comprises a module containing a linear RGD is preferred in cases where the peptide is fused by genetic engineering to the self-assembling polypeptide. In contrast thereto, a CAMP recognition sequence which comprises a module containing a cyclic RGD is preferred in cases where the peptide is fused by chemical coupling to the self-assembling polypeptide. In most preferred embodiments, the module containing a linear RGD is selected from the group consisting of RGDS (SEQ ID NO: 50), GRGDS (SEQ ID NO: 51), GRGDY (SEQ ID NO: 52), GGSGGRGDSPG (SEQ ID NO: 53), RGDSPASSKP (SEQ ID NO: 54), and CGGNGEPRGDYRAY (SEQ ID NO: 55), and/or the module containing a cyclic RGD is selected from the group consisting of c(RGDfK), c(RGDfC), and c(RGDfE). Thereby, RGD stands for the amino acids arginine (Arg), glycine (Gly), and aspartic acid (Asp); f stands for D-phenylalanine (D-Phe); and K stands for lysine (Lys), C stands for cysteine (Cys) and E stands for glutamic acid (Glu), respectively.

Alternatively or additionally, the CAMP recognition sequence comprising
i) a module containing GER is selected from the group consisting of GFOGER (SEQ ID NO: 56), GLOGER (SEQ ID NO: 57), GASGER (SEQ ID NO: 58), GROGER (SEQ ID NO: 59), GMOGER (SEQ ID NO: 60), GLSGER (SEQ ID NO: 61), and GAOGER (SEQ ID NO: 62),
ii) a module containing GEK is selected from the group consisting of GFOGEK (SEQ ID NO: 63), GLOGEK (SEQ ID NO: 64), GASGEK (SEQ ID NO: 65), GROGEK (SEQ ID NO: 66), GMOGEK (SEQ ID NO: 67), GLSGEK (SEQ ID NO: 68), and GAOGEK (SEQ ID NO: 69), or
iii) a module containing GEN is selected from the group consisting of GLOGEN (SEQ ID NO: 70) and GLKGEN (SEQ ID NO: 71).

The "O" in the above sequences refers to "hydroxyproline".

In a preferred embodiment of the invention, the peptide which is capable of enhancing the adhesive effect comprises at least one CAMP recognition sequence comprising or consisting of a module containing RGD, preferably a linear RGD, more preferably a linear RGD which is selected from the group consisting of RGDS (SEQ ID NO: 50), GRGDS (SEQ ID NO: 51), GRGDY (SEQ ID NO: 52), GGSGGRGDSPG (SEQ ID NO: 53), RGDSPASSKP (SEQ ID NO: 54), and CGGNGEPRGDYRAY (SEQ ID NO: 55), or a cyclic RGD, more preferably a cyclic RGD selected from the group consisting of c(RGDfK), c(RGDfC), and c(RGDfE), wherein the adhesive effect is mediated via binding of said peptide to an integrin as cell adhesion mediating protein (CAMP). Said binding is preferably a non-covalent binding, more preferably a non-covalent and reversible binding.

In another preferred embodiment of the invention, the peptide which is capable of enhancing the adhesive effect comprises at least one CAMP recognition sequence comprising or consisting of a module selected from the group consisting of (i) GER, preferably GFOGER (SEQ ID NO: 56), GLOGER (SEQ ID NO: 57), GASGER (SEQ ID NO: 58), GROGER (SEQ ID NO: 59), GMOGER (SEQ ID NO: 60), GLSGER (SEQ ID NO: 61), or GAOGER (SEQ ID NO: 62), (ii) GEK, preferably GFOGEK (SEQ ID NO: 63), GLOGEK (SEQ ID NO: 64), GASGEK (SEQ ID NO: 65), GROGEK (SEQ ID NO: 66), GMOGEK (SEQ ID NO: 67), GLSGEK (SEQ ID NO: 68), or GAOGEK (SEQ ID NO: 69), and (iii) GEN, preferably GLOGEN (SEQ ID NO: 70) or GLKGEN (SEQ ID NO: 71), wherein the adhesive effect is mediated via binding of said peptide to an integrin as cell adhesion mediating protein (CAMP). Said binding is preferably a non-covalent binding, more preferably a non-covalent and reversible binding. The "O" in the above sequences refers to "hydroxyproline".

Preferably, the self-assembling polypeptide is selected from the group consisting of a silk polypeptide, an elastin, a collagen, and a keratin. The silk polypeptide may be expressed in a recombinant, e.g. microbial, insect, plant, or mammalian expression system, i.e. separated from its natural milieu, (recombinant silk polypeptide), or may be harvested from natural sources, e.g. spider, silk worm, bee, mussel, or fly larvae. The silk polypeptide may be isolated or purified. In particular, a "purified silk polypeptide" or an "isolated silk polypeptide" is free or substantially free of cellular material, production/fermentation remnants, and/or other contaminating proteins from the cell or tissue source from which the protein is purified or isolated. The language "substantially free of cellular material" includes preparations of a silk polypeptide in which the silk polypeptide is separated from cellular components of the cells from which it is recombinantly produced. A silk polypeptide that is "substantially free" of cellular material, production/fermentation remnants, and/or other contaminating proteins from the cell or tissue source from which the protein is purified or isolated includes preparations of silk polypeptides having less than about 30%, 20%, 10%, 5%, 1%, or 0.1% (by dry weight) of contaminating protein and/or less than about 30%, 20%, 10%, 5%, 1%, or 0.1% (by dry weight) of contaminating lipid, DNA or salt.

It is more preferred that the silk polypeptide is a recombinant silk polypeptide. It is also more preferred that the silk polypeptide is a spider silk polypeptide, even more preferably a major ampullate silk polypeptide such as a dragline silk polypeptide, a minor ampullate silk polypeptide, or a flagelliform silk polypeptide of an orb-web spider (e.g. Araneidae or Araneoids), an insect silk polypeptide, a mussel byssus silk polypeptide, or a mixture thereof. The orb-web spider may be selected from the group consisting of *Araneus diadematus, Nephila clavipes*, and *Latrodectus hesperus*. The insect silk polypeptide may be of Lepidoptera, particularly Bombycidae such as *Bombyx mori*. The insect silk polypeptide may also be of Hymenoptera, particularly Apoidea such as Anthophila.

It is even more preferred that the silk polypeptide is a recombinant spider silk polypeptide, most preferably a recombinant major ampullate silk polypeptide such as a recombinant dragline silk polypeptide, a recombinant minor ampullate silk polypeptide, or a recombinant flagelliform silk polypeptide of an orb-web spider (e.g. Araneidae or Araneoids), a recombinant insect silk polypeptide, a recombinant mussel byssus silk polypeptide, or a mixture thereof. The orb-web spider may be selected from the group consisting of *Araneus diadematus, Nephila clavipes*, and *Latrodectus hesperus*. The recombinant insect silk polypeptide may be of Lepidoptera, particularly Bombycidae such as *Bombyx mori*. The insect silk polypeptide may also be of Hymenoptera, particularly Apoidea such as Anthophila.

It is also (alternatively or additionally) preferred that the silk polypeptide comprises, essentially consists of, or consists of at least two identical repetitive units. Said at least two identical repetitive units comprise or consists of identical copies of amino acid sequences of naturally occurring silk polypeptides or of variations of amino acid sequences of naturally-occurring silk polypeptides or of combinations of both.

The term a "repetitive unit", as used herein, refers to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence.

A "repetitive unit" having an amino acid sequence which is "substantially similar" to a corresponding amino acid sequence within a naturally occurring silk polypeptide (i.e. wild-type repetitive unit) is also similar with respect to its functional properties, e.g. a silk polypeptide comprising the "substantially similar repetitive unit" still has the ability to act as adhesive, particularly to function as tissue adhesive. The skilled person can readily assess whether the silk polypeptide comprising a "substantially similar repetitive unit" is still acting as adhesive, particularly is still functioning as tissue adhesive, for example, by conducting the adhesive or pulling test as described in the experimental section.

A "repetitive unit" having an amino acid sequence which is "identical" to the amino acid sequence of a naturally occurring silk polypeptide can be, for example, a portion of a silk polypeptide corresponding to one or more peptide motifs of MaSp I (SEQ ID NO: 43) MaSp II (SEQ ID NO: 44), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide can be, for example, a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2), but having one or more amino acid substitution(s) at (a) specific amino acid position(s).

The term, a "repetitive unit", as used herein, does not include the non-repetitive hydrophilic amino acid domain generally thought to be present at the amino terminus and/or carboxyl terminus of naturally occurring silk polypeptides.

The term a "repetitive unit", as used herein, further refers to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. Most preferably, the repetitive unit according to the invention consists of 3, 4, 5, 6, 7, 8, 9, 10, 12, 15, 18, 20, 24, 27, 28, 30, 34, 35, or 39 amino acids.

It should be noted that the terms "repetitive unit" and "repeat unit" can interchangeable be used in the context of the present invention.

In particularly preferred embodiments, the silk polypeptide is a polypeptide with an amino acid sequence which comprises or consists of at least 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the items 2, 6, or 16 represent the number of repetitive units) or multiple copies of two or more different repetitive units (e.g. $(AQ)_{24}$, or $(AQ)_{12}C_{16}$). Said silk polypeptide can further be modified by adding an artificial tag to facilitate the detection or purification of said protein (e.g. T7 tag).

The repetitive unit of the silk polypeptide can comprise or consist of an amino acid sequence of any region that comprises or consists of at least one peptide motif that repetitively occurs within a naturally occurring silk polypeptide known to one skilled in the art. Preferably, the repetitive unit of the silk polypeptide comprises or consists of an amino acid sequence of a region that comprises or consists of at least one peptide motif that repetitively occurs within an arthropod silk polypeptide, more preferably within a spider silk polypeptide, or an insect silk polypeptide. The repetitive unit of the silk polypeptide can also comprise or consist of an amino acid sequence of a region that comprises or consists of at least one peptide motif that repetitively occurs within a mussel silk polypeptide.

It is preferred that the spider silk repetitive unit comprises or consists of an amino acid sequence of a region that comprises or consists of at least one peptide motif that repetitively occurs within a naturally occurring major ampullate silk polypeptide (MaSp), such as a dragline silk polypeptide, a minor ampullate silk polypeptide (MiSp), or a flagelliform (FLAG) silk polypeptide. Most preferably, the repetitive unit comprises or consists of an amino acid sequence of a region that comprises or consists of at least one peptide motif that repetitively occurs within a naturally occurring dragline silk polypeptide or flagelliform silk polypeptide.

It is also preferred that the insect silk repetitive unit comprises or consists of an amino acid sequence of a region that comprises or consists of at least one peptide motif that repetitively occurs within a naturally occurring silk polypeptide of Lepidoptera. More preferably, the insect silk repetitive unit comprises or consists of an amino acid sequence of a region that comprises or consists of at least one peptide motif that repetitively occurs within a naturally occurring insect silk polypeptide of Bombycidae, most preferably of *Bombyx mori*.

The term "consensus sequence", as used herein, refers to an amino acid sequence which contains amino acids which frequently occur in a certain position (e.g. "G") and wherein, other amino acids which are not further determined are replaced by the place holder "X".

Preferably, the silk polypeptide comprises, essentially consists of, or consists of at least two identical repetitive units each comprising at least one, preferably one, consensus sequence selected from the group consisting of:
  i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q;
  iii) $A_x$, wherein x is an integer from 5 to 10;

iv) GGRPSDTYG; (SEQ ID NO: 18)
and
  v) GGRPSSSYG. (SEQ ID NO: 19)

More preferably, the above mentioned silk polypeptide has a molecular weight of at least 5 kDa, e.g. at least 5, 6, 7, 8, 9, 10, 11, 12, 13, 14, 15, 16, 17, 18, 19, or 20 kDa. Thus, in a more preferred embodiment, the self-assembling polypeptide has a molecular weight of at least 5 kDa, e.g. at least 5, 6, 7, 8, 9, 10, 11, 12, 13, 14, 15, 16, 17, 18, 19, or 20 kDa, and comprises at least two identical repetitive units each comprising at least one consensus sequence selected from the group consisting of:
  i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q;
  iii) $A_x$, wherein x is an integer from 5 to 10;

iv) GGRPSDTYG; (SEQ ID NO: 18)
and
  v) GGRPSSSYG. (SEQ ID NO: 19)

The iterated (peptide) motifs GPGXX (SEQ ID NO: 3) and GGX, i.e. glycine rich motifs, provide flexibility to the silk polypeptide and thus, to the thread formed from the silk protein containing said motifs. In detail, the iterated GPGXX (SEQ ID NO: 3) motif forms β-turn spiral structures, which imparts elasticity to the silk polypeptide. Major ampullate and flagelliform silks both have a GPGXX (SEQ ID NO: 3) motif. The iterated GGX motif is associated with a helical structure having three amino acids per turn and is found in most spider silks. The GGX motif may provide additional elastic properties to the silk. The iterated polyalanine $A_x$ (peptide) motif forms a crystalline β-sheet structure that provides strength to the silk polypeptide. (WO 03/057727). The GGRPSDTYG (SEQ ID NO: 18) and GGRPSSSYG (SEQ ID NO: 19) (peptide) motifs have been selected from Resilin (WO 08/155304). Resilin is an elastomeric protein found in most arthropods (arthropoda). It is located in specialised regions of the cuticle, providing low stiffness and high strength (Elvin et al., Nature (473): 999-1002, 2005).

Thus, in a preferred embodiment of the present invention, the silk polypeptide comprises or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In a further preferred embodiment of the present invention, the silk polypeptide comprises or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In an additionally preferred embodiment of the present invention, the silk polypeptide comprises or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In another preferred embodiment of the invention, the silk polypeptide comprises or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide comprises, essentially consists of, or consists of repetitive units, which comprise or consist of
  i) GPGAS (SEQ ID NO: 5), AAAAAA (SEQ ID NO: 13), GGY, and GPGSG (SEQ ID NO: 6) as amino acid sequence, preferably in this order,
  ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
  iv) GPGGA (SEQ ID NO: 9), GGP, GPGGA (SEQ ID NO: 9), GGP, GPGGA (SEQ ID NO: 9), and GGP as amino acid sequence, preferably in this order,
  v) AAAAAAAA (SEQ ID NO: 15), GPGQG (SEQ ID NO: 40), and GGR as amino acid sequence, preferably in this order,
  vi) AAAAAAAA (SEQ ID NO: 15), GPGGG (SEQ ID NO: 10), GGR, GGN, and GGR as amino acid sequence, preferably in this order,
  vii) GGA, GGA, GGA, GGS, GGA, and GGS as amino acid sequence, preferably in this order, and/or
  viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one, preferably one, consensus sequence selected from the group consisting of:

i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q;
  iii) $A_x$, wherein x is an integer from 5 to 10.

iv) GGRPSDTYG; (SEQ ID NO: 18)

and v) GGRPSSSYG. (SEQ ID NO: 19)

More preferably, the above mentioned silk polypeptide has a molecular weight of at least 5 kDa, e.g. at least 5, 6, 7, 8, 9, 10, 11, 12, 13, 14, 15, 16, 17, 18, 19, or 20 kDa. As mentioned above, at least two of the repetitive units comprised in the silk polypeptide are identical repetitive units.

Thus, the silk polypeptide preferably comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGQG (SEQ ID NO: 40), GPGGG (SEQ ID NO: 10), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk polypeptide comprises, essentially consists of, or consists of
  i) repetitive units which comprise or consist of GPGAS (SEQ ID NO: 5), AAAAAA (SEQ ID NO: 13), GGY, and GPGSG (SEQ ID NO: 6) as amino acid sequence, preferably in this order,
  ii) repetitive units which comprise or consist of AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  iii) repetitive units which comprise or consist of GPGQQ (SEQ ID NO: 4), GPGQQ (SEQ ID NO: 4), GPGQQ (SEQ ID NO: 4) and GPGQQ (SEQ ID NO: 4) as amino acid sequence,
  iv) repetitive units which comprise or consist of GPGGA (SEQ ID NO: 9), GGP, GPGGA (SEQ ID NO: 9), GGP, GPGGA (SEQ ID NO: 9), and GGP as amino acid sequence, preferably in this order,
  v) repetitive units which comprise or consist of AAAAAAAA (SEQ ID NO: 15), GPGQG (SEQ ID NO: 40), and GGR as amino acid sequence, preferably in this order, vi) repetitive units which comprise or consist of AAAAAAAA (SEQ ID NO: 15), GPGGG (SEQ ID NO: 10), GGR, GGN, and GGR as amino acid sequence, preferably in this order, vii) repetitive units which comprise or consist of GGA, GGA, GGA, GGS, GGA, and GGS as amino acid sequence, preferably in this order, and/or viii) repetitive units which comprise or consist of GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide comprises, essentially consists of, or consists of i) (GPGXX)$_n$ (SEQ ID NO: 3) as a repetitive unit, wherein X is any amino acid, preferably in each case independently selected from A, S, G, Y, P, and Q and n is 2, 3, 4, 5, 6, 7, 8, or 9;

ii) (GGX)$_n$ as a repetitive unit, wherein X is any amino acid, preferably in each case independently selected from Y, P, R, S, A, T, N and Q, more preferably in each case independently selected from Y, P and Q, and n is 2, 3, 4, 5, 6, 7, or 8; and/or iii) (A$_x$)$_n$ as a repetitive unit, wherein x is an integer from 5 to 10 and n is 2, 3, 4, 5, 6, 7, 8, 9, or 10.

More preferably, the above mentioned silk polypeptide has a molecular weight of at least 5 kDa, e.g. at least 5, 6, 7, 8, 9, 10, 11, 12, 13, 14, 15, 16, 17, 18, 19, or 20 kDa. As mentioned above, at least two of the repetitive units comprised in the silk polypeptides are identical repetitive units.

It is further preferred that the repetitive units are independently selected from module A (SEQ ID NO: 20), module C (SEQ ID NO: 21), module Q (SEQ ID NO: 22), module S (SEQ ID NO: 25), module R (SEQ ID NO: 26), or variants thereof (i.e. module A variants, module C variants, module Q variants, module S variants, or module R variants).

Modules A (SEQ ID NO: 20) and Q (SEQ ID NO: 22) are based on the amino acid sequence of ADF-3 of the spider *Araneus diadematus*. Module C (SEQ ID NO: 21) is based on the amino acid sequence of ADF-4 of the spider *Araneus diadematus*. Modules S (SEQ ID NO: 25) and R (SEQ ID NO: 26) are based on Resilin (Arthropoda) (WO 2008/155304).

Thus, in a preferred embodiment, the repetitive units of the silk polypeptide consist of module A: GPYGPGASAAAAAAGGYGPGSGQQ (SEQ ID NO: 20), module C: GSSAAAAAAAASGPGGYGPENQGPSGPGGYGPGGP (SEQ ID NO: 21), module Q: GPGQQGPGQQGPGQQGPGQQ (SEQ ID NO: 22), module S: PGSSAAAAAAAASGPGQGQGQGQGQGGRPSDTYG (SEQ ID NO: 25), module R: SAAAAAAAAGPGGGNGGRPSDTYGAPGGGNGGRPSSSYG (SEQ ID NO: 26), or variants thereof.

It is further particularly preferred that the silk polypeptide comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20), module C (SEQ ID NO: 21), module Q (SEQ ID NO: 22), module S (SEQ ID NO: 25), module R (SEQ ID NO: 26), or variants thereof (i.e. module A variants, module C variants, module Q variants, module S variants, or module R variants). It should be noted that at least two of the repetitive units comprised in the silk polypeptide are identical repetitive units (modules).

Thus, in a (particularly) preferred embodiment, the silk polypeptide comprises, essentially consists of, or consists of (i) repetitive unit(s) consisting of module A and/or repetitive unit(s) consisting of module A variants, (ii) repetitive unit(s) consisting of module C and/or repetitive unit(s) consisting of module C variants, (iii) repetitive unit(s) consisting of module Q and/or repetitive unit(s) consisting of module Q variants, (iv) (a) repetitive unit(s) consisting of module A and repetitive unit(s) consisting of module Q, (b) repetitive unit(s) consisting of module A and repetitive unit(s) consisting of module Q variants, (c) repetitive unit(s) consisting of module A variants and repetitive unit(s) consisting of module Q, (d) repetitive unit(s) consisting of module A variants and repetitive unit(s) consisting of module Q variants, (v) (a) repetitive unit(s) consisting of module A and repetitive unit(s) consisting of module C, (b) repetitive unit(s) consisting of module A and repetitive unit(s) consisting of module C variants, (c) repetitive unit(s) consisting of module A variants and repetitive unit(s) consisting of module C, (d) repetitive unit(s) consisting of module A variants and repetitive unit(s) consisting of module C variants, (vi) (a) repetitive unit(s) consisting of module C and repetitive unit(s) consisting of module Q, (b) repetitive unit(s) consisting of module C and repetitive unit(s) consisting of module Q variants, (c) repetitive unit(s) consisting of module C variants and repetitive unit(s) consisting of module Q, (d) repetitive unit(s) consisting of module C variants and repetitive unit(s) consisting of module Q variants, or (vii) (a) repetitive unit(s) consisting of module A, repetitive unit(s) consisting of module Q and repetitive unit(s) consisting of module C, (b) repetitive unit(s) consisting of module A, repetitive unit(s) consisting of module Q and repetitive unit(s) consisting of module C variants, (c) repetitive unit(s) consisting of module A, repetitive unit(s) consisting of module Q variants and repetitive unit(s) consisting of module C, (d) repetitive unit(s) consisting of module A variants, repetitive unit(s) consisting of module Q and repetitive unit(s) consisting of module C, (e) repetitive unit(s) consisting of module A, repetitive unit(s) consisting of module Q variants and repetitive unit(s) consisting of module C variants, (f) repetitive unit(s) consisting of module A variants, repetitive unit(s) consisting of module Q variants and repetitive unit(s) consisting of module C, (g) repetitive unit(s) consisting of module A variants, repetitive unit(s) consisting of module Q and repetitive unit(s) consisting of module C variants, (h) repetitive unit(s) consisting of module A variants, repetitive unit(s) consisting of module Q variants and repetitive unit(s) consisting of module C variants.

The modules A, C, Q, S, R, or variants thereof (i.e. module A variants, module C variants, module Q variants, module S variants, or module R variants) can also be combined or concatenated with each other in any combination and in any number of each, i.e. module (repetitive unit) A can be combined with module (repetitive unit) Q (i.e. combination AQ), module (repetitive unit) C can be combined with module (repetitive unit) Q (i.e. combination CQ), module (repetitive unit) Q can be combined with module (repetitive unit) A and with module (repetitive unit) Q (i.e. combination QAQ), module (repetitive unit) A can be combined with module (repetitive unit) A and with module (repetitive unit) Q (i.e. combination AAQ), etc., under the proviso that the silk polypeptide comprises or consists of at least two repetitive units which are identical. For example, the silk polypeptide can comprise or consist of $A_n$, $(AA)_n$, $(AQ)_n$, $(QA)_n$, $Q_n$, $(QQ)_n$, $(QAQ)_n$, $(AQA)_n$, $C_n$, $(CC)_n$, $(CCC)_n$, $(CQ)_n$, $(QC)_n$, $(QCQ)_n$, $(CQC)_n$, $(AA)_nQ_n$, $(QQ)_nA_n$, $(AAA)_nQ_n$, $(QQQ)_nA_n$, $(AQQ)_n$, $(QQA)_n$, $S_n$, $R_n$, $(SS)_n$, $(SR)_n$, $(RS)_n$, or $(RR)_n$, wherein n is at least 2, preferably 4, 8, 9, 10, 12, 16, 20, 24, or 32. In case that the silk polypeptide consists of $(AQ)_{12}$, it is noted that module (repetitive unit) A is 12 times present and module (repetitive unit) Q is also 12 times present in the silk polypeptide and that, thus, the silk polypeptide consists of 24 modules (repetitive units). The arrangement of the modules (repeat units) of a silk polypeptide consisting of $(AQ)_{12}$ is as follows: AQAQAQAQAQAQAQAQAQAQAQAQ. Further, in case that the silk polypeptide of the modules (repeat units) of a silk polypeptide consists of $(QAQ)_8$, it is noted that module (repeat unit) A is 8 times present and module (repetitive unit) Q is 16 times present in the silk polypeptide and that, thus, the silk polypeptide consists of 24 modules (repetitive units). The arrangement of the modules (repeat units) of a silk polypeptide consisting of $(QAQ)_8$ is as follows: QAQQAQQAQQAQQAQQAQQAQQAQ. The silk polypeptide can also comprise or consist of $(A*Q)_n$, $(AQ*)_n$, $(A*Q*)_n$, $(Q*A)_n$, $(QA*)_n$, $(Q*A*)_n$, $(QAQ*)_n$, $(QA*Q)_n$, $(Q*AQ)_n$, $(QA*Q*)_n$, $(Q*A*Q)_n$, $(Q*AQ*)_n$, $(Q*A*Q*)_n$, $(AQA*)_n$, $(AQ*A)_n$, $(A*QA)_n$, $(AQ*A*)_n$, $(A*Q*A)_n$, $(A*QA*)_n$, $(A*Q*A*)_n$, wherein n is at least 2, preferably 4, 8, 9, 10, 12, 16, 20, 24, or 32 and wherein * indicates a module variant, i.e. module A or Q variant.

The terms "combined with each other" or "concatenated with each other", as used herein, mean that the modules (repetitive units) are directly combined or concatenated with each other, or mean that the modules (repetitive units) are combined or concatenated with each other via one or more spacer amino acids. Thus, in one embodiment, the modules (repetitive units) comprised in the silk polypeptide are directly combined or concatenated with each other. In another embodiment, the modules (repetitive units) comprised in the silk polypeptide are combined or concatenated with each other via one or more spacer amino acids, preferably via 1 to 25 or 1 to 20 spacer amino acids, more preferably via 1 to 15 or 1 to 10 spacer amino acids, and most preferably, via 1 to 5 spacer amino acids, e.g. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acid may be any amino acid naturally occurring in proteins. Preferably, said spacer amino acid is not proline. It is preferred that the spacer amino acid contains a charged group(s). Preferably, the spacer amino acid containing a charged group(s) is independently selected from the group consisting of aspartate, glutamate, histidine, and lysine. Said spacer amino acid should be an amino acid which does not negatively affect the ability of a silk polypeptide to act as adhesive, particularly to function as tissue adhesive. Further, said spacer amino acid should be an amino acid which does not cause steric hindrance, e.g. an amino acid having a small size such as lysine and cysteine. In more preferred embodiments, the silk polypeptide comprises modules which are directly combined with each other and modules which are combined with each other via 1 to 25 or 1 to 20 spacer amino acids, more preferably via 1 to 15 or 1 to 10 spacer amino acids, and most preferably, via 1 to 5 spacer amino acids, e.g. via 2, 3, 4, 5, 6, 7, 8, 9, 10, 11, 12, 13, 14, 15, 16, 17, 18, 19, 20, 21, 22, 23, 24, or 25 spacer amino acids.

A module A, C, Q, S, or R variant differs from the reference (wild-type) module A, C, Q, S, or R from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference (wild-type) module from which it is derived. Thus, a module A, C, Q, S, or R variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, S, or R. Preferably, the sequence identity is over a continuous stretch of at least 10, 15, 18, 20, 24, 27, 28, 30, 34, 35, or more amino acids, preferably over the whole length of the respective reference (wild-type) module A, C, Q, S, or R.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, S, or R. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, S, or R.

A fragment (or deletion variant) of module A, C, Q, S, or R has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, S, or R variant or fragment is only regarded as a module A, C, Q, S, or R variant or fragment within the context of the present invention, if the modifications with respect to the amino acid sequence on which the variant or fragment is based do not negatively affect the ability of the silk polypeptide to act as adhesive, particularly to function as tissue adhesive. The skilled person can readily assess whether the silk polypeptide comprising a module A, C, Q, S, or R variant or fragment is still acting as adhesive, particularly to function as tissue adhesive, for example, by conducting the adhesive or pulling test as described in the experimental section.

It is more preferred that the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). The modules $A^C$ (SEQ ID NO: 29), $A^K$ (SEQ ID NO: 30), $C^C$ (SEQ ID NO: 31), $C^{K1}$ (SEQ ID NO: 32), $C^{K2}$ (SEQ ID NO: 33) and $C^{KC}$ (SEQ ID NO: 34) are variants of the module A which is based on the amino acid sequence of ADF-3 of the spider *Araneus diadematus* and of module C which is based on the amino acid sequence of ADF-4 of the spider *Araneus diadematus* (WO 2007/025719). In module $A^C$ (SEQ ID NO: 29) the amino acid S (serine) at position 21 has been replaced by the amino acid C (cysteine), in module $A^K$ (SEQ ID NO: 30) the amino acid S at position 21 has been replaced by the amino acid K (lysine), in module $C^C$ (SEQ ID NO: 31) the amino acid S at position 25 has been replaced by the amino acid 25 by C, in module $C^{K1}$ (SEQ ID NO: 32) the amino acid S at position 25 has been replaced by the amino acid K, in module $C^{K2}$ (SEQ ID NO: 33) the amino acid E (glutamate) at position 20 has been replaced by the amino acid K, and in module $C^{KC}$ (SEQ ID NO: 34) the amino acid E at position 20 has been replaced by the amino acid K and the amino acid S at position 25 has been replaced by the amino acid C (WO 2007/025719). Thus, in a more preferred embodiment, the repetitive units in the silk polypeptide consist of module $A^C$: GPYGPGASAAAAAAGGYG-PGCGQQ (SEQ ID NO: 29), module $A^K$: GPYGP-GASAAAAAAGGYGPGKGQQ (SEQ ID NO: 30), module $C^C$: GSSAAAAAAAASGPGGYGPENQGPCGPGGYG-PGGP (SEQ ID NO: 31), module $C^{K1}$: GSSAAAAAAAAS-GPGGYGPENQGPKGPGGYGPGGP (SEQ ID NO: 32), module $C^{K2}$: GSSAAAAAAAASGPGGYGPKNQGPS-GPGGYGPGGP (SEQ ID NO: 33), or module $C^{KC}$: GSSAAAAAAAASGPGGYGPKNQGPCGPGGYGPGGP (SEQ ID NO: 34).

It is even more preferred that the silk polypeptide comprises, essentially consists of, or consists of between 2 to 80 repetitive units, between 3 to 80 repetitive units, or between 4 to 60 repetitive units, preferably between 8 to 48 repetitive units, or between 10 to 40 repetitive units and most preferably between 16 to 32 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). It should be noted that at least two of the repetitive units comprised in the silk polypeptide are identical repetitive units (modules).

It is most preferred that the silk polypeptide comprises, essentially consists of, or consists of between 2 to 80 repetitive units, between 3 to 80 repetitive units or between 4 to 60 repetitive units, preferably between 8 to 48 repetitive units, or between 10 to 40 repetitive units and most preferably between 16 to 32 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20) or variants thereof, module C (SEQ ID NO: 21) or variants thereof, module Q (SEQ ID NO: 22) or variants thereof, module S (SEQ ID NO: 25) or variants thereof, module R (SEQ ID NO: 26) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33), or module $C^{KC}$ (SEQ ID NO: 34). Again, it should be noted that at least two of the repetitive units comprised in the silk polypeptide are identical repetitive units (modules).

The modules $A^K$, $C^C$, $C^{K1}$, $C^{K2}$ and $C^{KC}$ can also be combined with the modules A, C, Q, S, or R, i.e. module (repetitive unit) $A^K$ can be combined with module (repetitive unit) C (i.e. combination $A^KC$), or module (repetitive unit) $C^C$ can be combined with module (repetitive unit) C (i.e. combination $C^CC$), etc., under the proviso that the silk polypeptide comprises or consists of at least two repetitive units which are identical. Thus, the silk polypeptide can also comprise or consist of the modules $(AQA^K)_n$, $(QA^K)_n$, $(QA^KQ)_n$, $(A^KQA)_n$, $(A^KQA^K)_n$, $(CC^C)_n$, $(CC^CC)_n$, $(C^CC^CC)_n$, $(CC^CC_C)_n$, $(C^CQ)_n$, $(QC^C)_n$, $(QC^CQ)_n$, $(C^CQC)_n$, $(CQC^C)_n$, $(C^CQC^C)_n$, $(CC^{K1})_n$, $(C^{K1}C)_n$, $(C^{K1}CC)_n$, $(CC^{K1}C)_n$, $(C^{KC}C^{KC}C)_n$, $(CC^{KC}C^{KC})_n$, $(C^{KC}Q)_n$, $(QC^{KC})_n$, $(QC^{KC}Q)_n$, $(A^KC^{K1}Q)_n$, $(QC^{K2}A^K)_n$, or $(C^{K1}C^{K2}C)_n$, wherein n is at least 2, preferably 4, 5, 6, 7, 8, 10, 12, 16, or 20. As to the terms "combined with each other" or "concatenated with each other", it is referred to the definitions provided above. For example, the silk polypeptide comprises or consists of the modules $C_{16}C^C$, $C^CC_{16}$, $C_8C^CC_8$, $C_8C^C_8$, $C^C_8C_8$, $C_4C^C_8C_4$, $C^C_4C_8C^C_4$, $C^C(AQ)_{24}$, or $(AQ)_{24}$ $C^C$.

The silk polypeptide can further comprise at least one non-repetitive (NR) unit, e.g. at least 1, 2, 3, 4, 5, 6, or more NR unit(s), preferably one NR unit. In the context of the present invention, the term "non-repetitive (NR) unit" refers to a region of amino acids present in a naturally occurring silk polypeptide that displays no obvious repetition pattern (non-repetitive unit or NR unit). Preferably, the amino acid sequence of the non-repetitive unit corresponds to a non-repetitive amino acid sequence of naturally occurring dragline polypeptides, preferably of ADF-3 (SEQ ID NO: 1) or ADF-4 (SEQ ID NO: 2), or to an amino acid sequence substantially similar thereto. The amino acid sequence of the non-repetitive unit may also correspond to a non-repetitive amino acid sequence of black widow. More preferably, the amino acid sequence of the non-repetitive unit corresponds to a non-repetitive carboxy terminal amino acid sequence of naturally occurring dragline polypeptides, preferably of ADF-3 (SEQ ID NO: 1) or ADF-4 (SEQ ID NO: 2), or to an amino acid sequence substantially similar thereto. Even more preferably, the amino acid sequence of the non-repetitive unit corresponds to a non-repetitive carboxy terminal amino acid sequence of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxy terminal) amino acid sequence of naturally occurring dragline polypeptides, preferably of ADF-3 (SEQ ID NO: 1) or ADF-4 (SEQ ID NO: 2). A "non-repetitive unit" having an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO: 1) or ADF-4 (SEQ ID NO: 2), is also similar with respect to its functional properties, e.g. a silk polypeptide comprising the "substantially similar non-repetitive unit" still has the ability to act as adhesive, particularly to function as tissue adhesive. The skilled person can readily assess whether the silk polypeptide comprising the "substantially similar non-repetitive unit" is still acting as adhesive, particularly is still functioning as tissue adhesive, for example, by conducting the adhesive or pulling test as described in the experimental section.

Most preferably, the non-repetitive (NR) unit is NR3 (SEQ ID NO: 41) or variants thereof, NR4 (SEQ ID NO: 42) or variants thereof, NR5 (SEQ ID NO: 76) or variants thereof, or NR6 (SEQ ID NO: 77) or variants thereof. The NR3 (SEQ ID NO: 41) unit is based on the amino acid sequence of ADF-3 of the spider *Araneus diadematus* and the NR4 (SEQ ID NO: 42) unit is based on the amino acid sequence of ADF-4 of the spider *Araneus diadematus* (WO 2006/008163). In addition, the NR5 (SEQ ID NO: 76) unit and the NR6 (SEQ ID NO: 77) unit is derived from *Latrodectus hesperus*.

A NR3, NR4, NR5, or NR6 unit variant differs from the reference NR3 (SEQ ID NO: 41), NR4 (SEQ ID NO: 42), NR5 (SEQ ID NO: 76), or NR6 (SEQ ID NO: 77) unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3, NR4, NR5, or NR6 unit variant can alternatively or additionally be characterised by a certain degree of sequence identity to the reference NR3, NR4, NR5, or NR6 unit from which it is derived. Thus, a NR3, NR4, NR5, or NR6 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3, NR4, NR5, or NR6 unit. Preferably, the sequence identity is over a continuous stretch of at least 10, 20, 30, 40, 50, 60, 70, 80, 90, or more amino acids, preferably over the whole length of the respective reference NR3, NR4, NR5, or NR6 unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3, NR4, NR5, or NR6 unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3, NR4, NR5, or NR6 unit.

A fragment (or deletion variant) of a NR3, NR4, NR5, or NR6 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3, NR4, NR5, or NR6 unit variant or fragment is only regarded as a NR3, NR4, NR5, or NR6 unit variant or fragment within the context of the present invention, if the modifications with respect to the amino acid sequence on which the variant or fragment is based do not negatively affect the ability of a silk polypeptide to act as adhesive, particularly to function as tissue adhesive. The skilled person can readily assess whether the silk polypeptide comprising a NR3, NR4, NR5, or NR6 unit variant or fragment is still acting as adhesive, particularly to function as tissue adhesive, for example, by conducting the adhesive or pulling test as described in the experimental section.

Preferably, the silk polypeptide is selected from the group consisting of ADF-3 (SEQ ID NO: 1) or variants thereof, ADF-4 (SEQ ID NO: 2) or variants thereof, MaSp I (SEQ ID NO: 43) or variants thereof, MaSp II (SEQ ID NO: 44) or variants thereof, $(C)_m$, $(C)_m NR_z$, $NR_z(C)_m$, $(AQ)_n$, $(AQ)_n NR_z$, $NR_z(AQ)_n$, $(QAQ)_o$, $NR_z(QAQ)_o$, $(QAQ)_o NR_z$, wherein m is an integer of 8 to 48 (i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48), n is an integer of 6 to 24 (i.e. 6, 7, 8, 9, 10, 11, 12, 13, 14, 15, 16, 17, 18, 19, 20, 21, 22, 23, or 24), o is an integer of 8 to 16 (i.e. 8, 9, 10, 11, 12, 13, 14, 15, or 16), z is an integer of 1 to 3 (i.e. 1, 2, or 3), and NR stands for a non-repetitive unit. The above mentioned formulas are defined by one of the following: In the formula i) $(C)_m$, a "m" number of C modules, namely 8 to 48 C modules, represented by the amino acid sequence according to SEQ ID NO: 21, are combined with each other, ii) $(C)_m NR_z$, a "m" number of C modules, namely 8 to 48 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, is present (z=1) or are combined with each other (z=2 or 3), wherein said non-repetitive (NR) unit(s) is (are) further combined with a "m" number of C modules, namely 8 to 48 C modules, represented by the amino acid sequence according to SEQ ID NO: 21, iv) $(AQ)_n$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, v) $(AQ)_n NR_z$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, vi) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, is present (z=1) or are combined with each other (z=2 or 3), wherein said non-repetitive (NR) unit(s) is (are) further combined with a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, vii) $(QAQ)_o$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, viii) $(QAQ)_o NR_z$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, and ix) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 41, NR4 represented by the amino acid sequence according to SEQ ID NO: 42, NR5 represented by the amino acid sequence according to SEQ ID NO: 76, or NR6 represented by the amino acid sequence according to SEQ ID NO: 77, is present (z=1) or are combined with each other (z=2 or 3), wherein said non-repetitive (NR) unit(s) is (are) further combined with a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20.

More preferably, the silk polypeptide is $C_{16}NR4$, $C_{32}NR4$, $(AQ)_{12}NR3$, $(AQ)_{24}NR3$, $(AQ)_{12}$, $(AQ)_{24}$, $C_{16}$, $C_{32}$, $NR4C_{16}NR4$, $NR4C_{32}NR4$, $NR3C_{16}NR3$, $NR3C_{32}NR3$, $NR4(AQ)_{12}NR4$, $NR4(AQ)_{24}NR4$, $NR3(AQ)_{12}NR3$, $NR3(AQ)_{24}NR3$, $(QAQ)_8$ or $(QAQ)_{16}$.

An ADF-3, ADF-4, MaSp I or MaSp II variant differs from the reference (wild-type) ADF-3 (SEQ ID NO: 1), ADF-4 (SEQ ID NO: 2), MaSp I (SEQ ID NO: 43) or MaSp II (SEQ ID NO: 44) polypeptide from which it is derived by up to 150 (up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150) amino acid changes in the amino acid sequence (i.e. substitutions, insertions, deletions, N-terminal truncations and/or C-terminal truncations). Such a variant can alternatively or additionally be characterised by a certain degree of sequence identity to the reference (wild-type) polypeptide from which it is derived. Thus, an ADF-3, ADF-4, MaSp I or MaSp II variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) ADF-3, ADF-4, MaSp I or MaSp II polypeptide. Preferably, the sequence identity is over a continuous stretch of at least 20, 25, 30, 35, 40, 50, 60, 70, 80, 90, 100, 120, 150, 180, 200, 250, 300, 350, 400, or more amino acids, preferably over the whole length of the respective reference (wild-type) ADF-3, ADF-4, MaSp I or MaSp II polypeptide.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) ADF-3, ADF-4, MaSp I or MaSp II polypeptide. It is further particularly preferred that the sequence identity is at least 80% over a continuous stretch of at least 20, 30, 50, 100, 150, 200, 250, or 300 amino acids, is at least 85% over a continuous stretch of at least 20, 30, 50, 100, 150, 200, 250, or 300 amino acids, is at least 90% over a continuous stretch of at least 20, 30, 50, 100, 150, 200, 250, or 300 amino acids, is at least 95% over a continuous stretch of at least 20, 30, 50, 100, 150, 200, 250, or 300 amino acids, is at least 98% over a continuous stretch of at least 20, 30, 50, 100, 150, 200, 250, or 300 amino acids, or is at least 99% over a continuous stretch of at least 20, 30, 50, 100, 150, 200, 250, or 300 amino acids of the respective reference (wild-type) ADF-3, ADF-4, MaSp I or MaSp II polypeptide.

A fragment (or deletion variant) of the ADF-3 (SEQ ID NO: 1) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 350, 370, 400, 420, 450, 470, 500, 520, 550, 570, 600, or 610 amino acids at its N-terminus and/or at its C-terminus. The deletion can also be internally.

A fragment (or deletion variant) of the ADF-4 (SEQ ID NO: 2) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 330, 340, 350, 360, 370, 380, or 390 amino acids at its N-terminus and/or at its C-terminus. The deletion can also be internally.

A fragment (or deletion variant) of the MaSp I (SEQ ID NO: 43) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 620, 640, 660, 670, 680, or 690 amino acids at its N-terminus and/or at its C-terminus. The deletion can also be internally.

A fragment (or deletion variant) of the MaSp II (SEQ ID NO: 44) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 520, 540, 560, or 570 amino acids at its N-terminus and/or at its C-terminus. The deletion can also be internally.

Additionally, the ADF-3, ADF-4, MaSp I or MaSp II variant or fragment is only regarded as an ADF-3, ADF-4, MaSp I or MaSp II variant or fragment within the context of the present invention, if the modifications with respect to the amino acid sequence on which the variant or fragment is based do not negatively affect the ability of the silk polypeptide to act as adhesive, particularly to function as tissue adhesive. The skilled person can readily assess whether the silk polypeptide comprising a NR or NR4 unit variant or fragment is still acting as adhesive, particularly to function as tissue adhesive, for example, by conducting the adhesive or pulling test as described in the experimental section.

In a preferred embodiment of the invention, the silk polypeptide, preferably the spider silk polypeptide, more preferably major ampullate silk polypeptide such as dragline silk polypeptide, minor ampullate silk polypeptide, or flagelliform silk polypeptide of an orb-web spider (e.g. Araneidae or Araneoids), the insect silk polypeptide, or the mussel byssus silk polypeptide comprises, preferably attached (e.g. covalently linked or coupled) to the N- and/or C-terminus, a peptide capable of enhancing the adhesive effect which comprises at least one CAMP recognition sequence comprising or consisting of a module containing RGD, preferably a linear ROD, more preferably a linear RGD which is selected from the group consisting of RGDS (SEQ ID NO: 50), GRGDS (SEQ ID NO: 51), GRGDY (SEQ ID NO: 52), GGSGGRGDSPG (SEQ ID NO: 53), RGDSPASSKP (SEQ ID NO: 54), and CGGNGEPRGDYRAY (SEQ ID NO: 55), or a cyclic RGD, more preferably a cyclic RGD selected from the group consisting of c(RGDfK), c(RGDfC), and c(RGDfE).

In a more preferred embodiment of the invention, the silk polypeptide, preferably the spider silk polypeptide, more preferably major ampullate silk polypeptide such as dragline silk polypeptide, minor ampullate silk polypeptide, or flagelliform silk polypeptide of an orb-web spider (e.g. Araneidae or Araneoids), the insect silk polypeptide, or the mussel byssus silk polypeptide comprises, preferably attached (e.g. covalently linked or coupled) to the N- and/or C-terminus, more preferably attached (e.g. covalently linked or coupled) to the C-terminus, a peptide capable of enhancing the adhesive effect which comprises at least one CAMP recognition sequence comprising or consisting of a module containing GGSGGRGDSPG (SEQ ID NO: 53) (see, for example, FIG. 1B).

In another more preferred embodiment of the invention, the silk polypeptide, preferably the spider silk polypeptide, more preferably major ampullate silk polypeptide such as dragline silk polypeptide, minor ampullate silk polypeptide, or flagelliform silk polypeptide of an orb-web spider (e.g. Araneidae or Araneoids), the insect silk polypeptide, or the mussel byssus silk polypeptide comprises an amino terminal and/or a carboxy terminal TAG, preferably an amino terminal TAG, selected from the group consisting of $TAG^{CYS1}$ (SEQ ID NO: 35), $TAG^{CYS2}$ (SEQ ID NO: 36), $TAG^{CYS3}$ (SEQ ID NO: 37), $TAG^{LYS1}$ (SEQ ID NO: 38) and $TAG^{LYS2}$ (SEQ ID NO: 39), preferably $TAG^{CYS3}$ (SEQ ID NO: 37), and further comprises a peptide capable of enhancing the adhesive effect which comprises at least one CAMP recognition sequence comprising or consisting of a module containing c(RGDfK), c(RGDfC), or c(RGDfE), preferably c(RGDfK). Said TAG(s) is (are) preferably attached (e.g. covalently linked or coupled) to the N-terminus and/or C-terminus of said silk polypeptide, and/or said peptide is preferably attached (e.g. covalently linked or coupled) to said TAG(s). It is particularly preferred that said peptide is covalently coupled to the thiol group of a cysteine residue comprised in the amino terminal and/or carboxy terminal TAG selected from the group consisting of $TAG^{CYS1}$ (SEQ ID NO: 35), $TAG^{CYS2}$ (SEQ ID NO: 36), and $TAG^{CYS3}$ (SEQ ID NO: 37) (see, for example, FIG. 1A).

In another preferred embodiment of the invention, the silk polypeptide, preferably the spider silk polypeptide, more preferably major ampullate silk polypeptide such as a dragline silk polypeptide, minor ampullate silk polypeptide, or flagelliform silk polypeptide of an orb-web spider (e.g. Araneidae or Araneoids), the insect silk polypeptide, or the mussel byssus silk polypeptide comprises, preferably attached to the N- and/or C-terminus, a peptide capable of enhancing the adhesive effect which comprises at least one CAMP recognition sequence comprising or consisting of a module selected from the group consisting of (i) GER, preferably GFOGER (SEQ ID NO: 56), GLOGER (SEQ ID NO: 57), GASGER (SEQ ID NO: 58), GROGER (SEQ ID NO: 59), GMOGER (SEQ ID NO: 60), GLSGER (SEQ ID NO: 61), or GAOGER (SEQ ID NO: 62), (ii) GEK, preferably GFOGEK (SEQ ID NO: 63), GLOGEK (SEQ ID NO: 64), GASGEK (SEQ ID NO: 65), GROGEK (SEQ ID NO: 66), GMOGEK (SEQ ID NO: 67), GLSGEK (SEQ ID NO: 68), or GAOGEK (SEQ ID NO: 69), and (iii) GEN, preferably GLOGEN (SEQ ID NO: 70) or GLKGEN (SEQ ID NO: 71). The "O" in the above sequences refers to "hydroxyproline".

The above mentioned adhesive effect is preferably mediated via binding (e.g. non-covalent binding, particularly non-covalent and reversible binding) of said peptide to an integrin as cell adhesion mediating protein (CAMP). Additionally or alternatively, the above mentioned silk polypeptides are recombinant silk polypeptides.

The self-assembling polypeptide, as described herein, may be provided in several preferential compositions including, but not limited to, solid compositions such as powdery compositions, liquid compositions such as aqueous compositions, e.g. aqueous solutions, emulsions, or suspensions, aerosols such as dry or liquid aerosols, pump sprays, and pasty compositions. These compositions comprising the self-assembling polypeptide may additionally comprise one or more pharmaceutical compounds such as therapeutic or diagnostic compounds.

The self-assembling polypeptide, as described herein, may further be provided as film, gel, particularly hydrogel, foam, mesh, scaffold, patch, nonwoven, or layer, particularly covering or coating layer. The film, gel, particularly hydrogel, foam, mesh, scaffold, path, nonwoven, or layer, particularly covering or coating layer, comprising the self-assembling polypeptide may additionally comprise one or more pharmaceutical compounds.

The self-assembling polypeptide, as described herein, may also be applied to several preferential objects including, but not limited to, meshes, scaffolds, patches, nonwovens, and implants, for example, dental implants, microchip implants, soft tissue implants such as silicone implants, or implants with a silicone surface (e.g. cochlea implants). Due to this application, the objects including, but not limited to, meshes, scaffolds, patches, nonwovens, and implants, for example, dental implants, microchip implants, soft tissue implants such as silicone implants, or implants with a silicone surface (e.g. cochlea implants) may be covered or coated, e.g. partially or completely covered or coated, with the self-assembling polypeptide.

It can be applied to these objects via dip-coating, spraying, or dropping. For dip-coating, preferential objects are dipped into liquid compositions such as aqueous compositions, e.g. aqueous solutions, comprising the self-assembling polypeptide. Further, for spraying, liquid compositions such as aqueous compositions, e.g. aqueous solutions, comprising the self-assembling polypeptide are sprayed onto preferential objects. Furthermore, for dropping, liquid compositions such as aqueous compositions, e.g. aqueous solutions, comprising the self-assembling polypeptide are dropped onto preferential objects. These liquid compositions comprising the self-assembling polypeptide may additionally comprise one or more pharmaceutical compounds such as therapeutic or diagnostic compounds.

The term "pharmaceutical compound", as used herein, is defined below. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof.

Thus, in a preferred embodiment of the present invention, the self-assembling polypeptide, as described herein, is for use as tissue adhesive, wherein the self-assembling polypeptide is provided (i) as film, gel, particularly hydrogel, foam, mesh, scaffold, patch, nonwoven or layer, particularly covering or coating layer, or (ii) comprised in and/or on an object, e.g. a mesh, scaffold, patch, nonwoven or implant, for example, dental implant, microchip implant, soft tissue implant such as silicone implant or implant with a silicone surface (e.g. cochlea implant). Said object (e.g. mesh, scaffold, patch or nonwoven), may be inserted into the wound (e.g. inserted into the cut or gap of the wound) and may be left in the wound.

In preferred embodiments of the invention, the self-assembling polypeptide, as described herein, is for use as tissue adhesive
i) in the treatment of a wound,
ii) in the treatment of a sutured wound,
iii) in the reduction or prevention of fibrosis, particularly capsular fibrosis, and/or in the reduction or prevention of scarring,
iv) in the fixation of transplants, preferably tissue transplants or organ transplants, more preferably skin transplants,
v) in the fixation of medical devices, preferably implants, more preferably silicone implants or implants with a silicone surface, and/or
vi) in surgical interventions.

As mentioned above, the self-assembling polypeptide, as described herein, is for use as tissue adhesive in the treatment of a wound. The inventors of the present invention surprisingly found that the self-assembling polypeptide, as described herein, can be used to reconnect tissue layers of a wound with each other. Particularly, the tissue adhesive can provide a close, especially form-fit, connection between tissue layers, or in the event that the tissue layers are distant from each other, the tissue adhesive can fill the gap between the tissue layers, replace the missing tissue layers and/or bridge the missing tissue layers. Preferably, the gap has a size of no more than 1 cm, more preferably of no more than 0.75 cm, even more preferably of no more than 0.5 cm, most preferably of no more than 0.25 cm, e.g. of no more than 0.01, 0.015, 0.02, 0.025, 0.0.3, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1 cm.

The term "wound", as used herein, includes damages to any tissue in a patient. As used herein, the term "patient" means any mammal or bird that may benefit from the tissue adhesive as described herein. Preferably, the patient is selected from the group consisting of a laboratory animal (including, for example, a mouse or rat), a domestic animal (including, for example, a guinea pig, rabbit, chicken, turkey, pig, sheep, goat, camel, cow, horse, donkey, cat, or dog), and primates (including, for example, a chimpanzee and a human being). It is particularly preferred that the patient is a human being. Alternatively, the patient is selected from the group consisting of a human being and an animal.

The wound may be comprised on the surface of the body of a patient, e.g. human being, (i.e. a superficial wound), or may be comprised within the body of a patient, e.g. human being (i.e. an internal wound). The wound may have been caused by any means including, but not limited to, infections, inflammations, surgical interventions, external components such as sharp objects, e.g. scalpels, knifes or nails, and external circumstances, such as accidents, e.g. bicycle, motor vehicle, or auto accidents.

It is particularly preferred that the wound is selected from the group consisting of a topical wound, deep wound, gaping wound, stab wound, puncture wound, penetration wound, surgical incision, laceration, cut, and trauma (e.g. blunt or sharp trauma). The term "topical wound", as used herein, refers to a wound on the tissue surface. The term "puncture wound", as used herein, refers to a wound caused by an object puncturing tissue(s), e.g. multiple (different) tissues, particularly an organ, e.g. skin, such as a nail or needle. The term "penetration wound", as used herein, refers to a wound caused by an object entering and coming out from the tissue(s), e.g. multiple (different) tissues, particularly an organ, e.g. skin, such as a nail or needle. The term "surgical incision", as used herein, refers to a wound caused by a sharp object, e.g. a scalpel or knife, during surgery. The term "trauma", as used herein, is defined as an injury caused by a physical fore, e.g. include the consequences of motor vehicle accidents.

The wound may be located in or on the surface of a tissue. The tissue may be selected form the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, glands such as lymph and thyroid glands, eye, or pancreas, is, for example, comprised of multiple (different) tissues. Thus, the wound may also be located in an organ, particularly encompassing multiple (different) tissues or tissue layers. Particularly, the wound is a skin lesion.

In preferred embodiments of the invention, the self-assembling polypeptide, as described herein, is for use as tissue adhesive in (i) the topical treatment of a wound site and/or (ii) the treatment of an internal wound site, e.g. in case of deeper wounds or during surgical procedures.

As mentioned above, the self-assembling polypeptide, as described herein, is for use as tissue adhesive in the treatment of a sutured wound. The inventors of the present invention surprisingly found that the self-assembling polypeptide, as described herein, can be used to further seal a sutured wound. In this case, the self-assembling polypeptide acting as a tissue adhesive can further fix and/or glue the sutured tissue layers with each other. This may strengthen the effect of the wound suture, prevent after-bleeding, and/or avoid subsequent infections, e.g. bacterial or viral infections. Sutured wounds which are treated with the self-assembling polypeptide, as described herein, advantageously exhibit reduced or no scarring and/or show a shortened healing. It is particularly preferred that the sutured wound is selected from the group consisting of a topical wound, deep wound, gaping wound, stab wound, puncture wound, penetration wound, surgical incision, laceration, cut, and trauma (e.g. blunt trauma or sharp trauma).

As mentioned above, the self-assembling polypeptide, as described herein, is for use as tissue adhesive in the reduction or prevention of fibrosis, particularly capsular fibrosis, and/or in the reduction or prevention of scarring. Preferably, wounds which are glued with the self-assembling polypeptide, particularly silk polypeptide, as described herein, exhibit reduced or no scarring and/or show a reduced or no fibrosis, particularly capsular fibrosis.

Further, as mentioned above, the self-assembling polypeptide, as described herein, is for use as tissue adhesive in the fixation of transplants, preferably tissue transplants or organ transplants, more preferably skin transplants. The inventors surprisingly found that the self-assembling polypeptide can be used in the fixation of transplants, preferably tissue transplants or organ transplants, more preferably skin transplants. Particularly skin transplants have the disadvantage that they tend to slip after application. This is especially caused by patient movements which cannot be completely obviated. Under these circumstances, the correct healing process is delayed or even prevented. The skin transplants are preferably selected from the group consisting of autologous skin transplants (also designated as autografts), isogeneic skin transplants (also designated as isografts or syngrafts), allogeneic skin transplants (also designated as allografts), xenogenic skin transplants (also designated as xenografts or heterografts), and prosthetic skin transplants (also designated as prosthetic grafts). The meaning of these terms is clear for the skilled person. In order to fix the transplants, e.g. tissue transplants or organ transplants such as skin transplants, to tissue or in the body cavity, the surface area of the transplants, e.g. tissue transplants or organ transplants such as skin transplants, that will be in contact with the tissue or body cavity may be covered or coated, e.g. partially or completely covered or coated, with the self-assembling polypeptide. Alternatively or additionally, the tissue or body cavity that will be in contact with the transplants, e.g. tissue transplants or organs transplants such as skin transplants, may be covered or coated, e.g. partially or completely covered or coated, with the self-assembling polypeptide.

Furthermore, as mentioned above, the self-assembling polypeptide, as described herein, is for use as a tissue adhesive in the fixation of medical devices such as implants. The inventors surprisingly found that the self-assembling polypeptide, as described herein, can be used to connect tissue layers to artificial surfaces, e.g. of medical devices such as implants, or can be used to connect artificial surfaces, e.g. of medical devices such as implants, to tissue layers. For this purpose, the tissue layers or artificial surfaces, e.g. of the medical devices such as implants, can be covered or coated, e.g. partially or completely covered or coated, with the self-assembling polypeptide. Thereby, the medical devices such as implants are fixed, particularly embedded or incorporated, in the tissue.

The term "medical device", as used herein, refers to an instrument, apparatus, implant, or other similar or related article, which is intended for use in the diagnosis of diseases or other conditions, or in the cure, mitigation, treatment or prevention of diseases, or which is intended to affect the structure or any function of the body and which does not achieve any of its primary intended purposes through chemical action within or on the body. Particularly, medical devices achieve their principal action by physical, physicochemical, or mechanical means. It is preferred that the medical devices are selected from the group consisting of implants, preferably dental implants, microchip implants, soft tissue implants such as silicone implants, or implants with a silicone surface (e.g. cochlea implants), cardiac pacemakers, pumps, preferably insulin pumps, cannula, preferably cannula for the drainage of liquor, ichor, or blood, deposits, preferably drug deposits, fixations, preferably internal or external fixations ("fixateur externe" in French), prostheses, preferably neuroprostheses, and sensors, preferably sensors measuring the body temperature, blood pressure, or pulse rate. The silicone implants or implants with a silicone surface may also be breast implants.

The medical device may be a subdermal or transdermal medical device, e.g. a transdermal or subdermal implant. A subdermal medical device is a device that is completely buried in the skin, while a transdermal medical device is placed under the skin, but also protrudes out of it.

In addition, as mentioned above, the self-assembling polypeptide as described herein is for use in surgical interventions. It is also particularly preferred that the surgical interventions are selected from the group consisting of cardiovascular surgical interventions, cardiothoracic surgical interventions, gastrointestinal surgical interventions, pneumothoracic surgical interventions, neurosurgical interventions, urological surgical interventions, dental surgical interventions, reconstructive surgical interventions, surgical interventions in the ear, surgical interventions in the nose, surgical interventions in the throat area, lymphatic, biliary and cerebrospinal fistulae, air leakages during thoracic and pulmonary surgical interventions, orthopaedic surgical interventions, gynaecological surgical interventions, cosmetical surgical interventions, and vascular surgical interventions. It is particularly preferred that the cosmetical or reconstructive surgical interventions include the insertion of implants, preferably dental implants, soft tissue implants such as silicone implants, or implants with a silicone surface (e.g. cochlea implants). The silicone implants or implants with a silicone surface may also be breast implants.

The self-assembling polypeptide as tissue adhesive may be used as part of a composition such as an aqueous solution having a temperature of 20° C. and a pH of between 4.5 and 7.0 such as of between 4.5 and 6.5, between 4.8 and 5.9, or of between 5.4 and 5.9. The adhesive effect of the self-assembling polypeptide can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide can be improved by decreasing the pH of the composition such as aqueous solution by 0.1 to 2.5 pH units, e.g. by 0.1 to 0.5 pH units, below the pH of the tissue to be glued. The tissue to be glued may have a pH of between 4.5 and 7.0 such as of between 4.5 and 6.5, of between 4.8 and 5.9, or of between 5.4 and 5.9.

The first aspect of the present invention, as described above, can alternatively be worded as follows: In a first aspect, the present invention relates to a method of using a self-assembling polypeptide as tissue adhesive.

In a second aspect, the present invention relates to the use of a self-assembling polypeptide as tissue adhesive. Said use may be an in vivo, in vitro or ex vivo use, preferably an in vitro or ex vivo use. As to the definition of the terms "self-assembling polypeptide" and "tissue adhesive", it is referred to the first aspect of the present invention. The tissue is preferably selected from the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, adrenal glands, lymph and thyroid glands, eye, or pancreas, is, for example, comprised of multiple (different) tissues. As to the preferred embodiments of the "self-assembling polypeptide", particularly silk polypeptide, elastin, collagen, or keratin, it is also referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

As mentioned above, the present invention relates to the use of a self-assembling polypeptide, e.g. silk polypeptide such as spider silk polypeptide, as tissue adhesive. Preferably, the self-assembling polypeptide is used to process food. In one embodiment, the self-assembling polypeptide is used to glue tissues, preferably meat, more preferably pork, beef, chicken, or turkey.

The second aspect of the present invention, as described above, can alternatively be worded as follows: In a second aspect, the present invention relates to a method of using a self-assembling polypeptide as tissue adhesive.

In a third aspect, the present invention relates to the use of a self-assembling polypeptide to glue one or more cosmetic compounds on skin, mucosa, and/or hair, particularly on skin surfaces, mucosa surfaces and/or hair surfaces.

As to the definition of the term "self-assembling polypeptide" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

The term "cosmetic compound (also designated as cosmetic substance)", as used herein, refers to a substance intended mainly for external use on the body surface, e.g. human body surface, or in the oral cavity, e.g. of a human, for cleaning and personal hygiene to alter the appearance or body odor or to convey scent. In particular, it is meant that a cosmetic substance is a molecule which shows a certain predictable effect. Such an effect molecule can be, for example, a proteinaceous molecule (e.g. an enzyme) or a non-proteinaceous molecule (e.g. a dye, pigment, photoprotective agent, vitamin, provitamin, an antioxidant, conditioner, or a compound comprising metal ions).

Among the proteinaceous molecules, enzymes are preferred. Examples for useful enzymes include, but are not limited to, oxidases, peroxidases, proteases, glucanases, mutanases, tyrosinases, metal-binding enzymes, lactoperoxidases, lysozymes, aminoglycosidases, glucose oxidases, super oxide dismutases, photolyases, proteins binding heavy metals, T4 endonucleases, catalases, and reductases such as thioredoxin-reductases. Also preferred are proteinaceous substances which do not possess an enzymatic function. Examples for non-enzymatic proteinaceous molecules include, but are not limited to, antimicrobial peptides, hydrophobins, collagens, keratins, proteins binding heavy metals, proteins binding odorants, proteins binding cellulose, proteins binding starch, and proteins binding keratin. Other preferred proteinaceous molecules are, for example, protein hydrolysates, e.g. protein hydrolysates of plant or animal sources. Said protein hydrolysates can be of marine origin.

Among the non-proteinaceous molecules, UV-protective agents, antioxidants, vitamins, provitamins and their precursors and their derivatives, dyes, polysaccharides, or fragrances are preferred. The term "UV-protective agent", as used herein, refers to an organic substance which can absorb specific wavelengths in the range of UV-wavelengths. The absorbed energy can then emitted in form of longer wave radiation, e.g. heat. The term "antioxidant", as used herein, refers to a compound that interrupts the photochemical reaction chain triggered by UV radiation when penetrating into the skin. Typical examples of antioxidants include, but are not limited to, super oxide dismutase, catalase, tocopherol (vitamin E), ascorbic acid (vitamin C), coenzyme Q10 (ubiquinane), and quinione. Examples of vitamins, provitamins and their precursors include, but are not limited to, β-carotene (provitamin of vitamin A), ascorbic acid (vitamin C), tocopherol (vitamin E), the vitamins, provitamins and their precursors of the vitamin B group encompassing vitamin $B_1$ (thiamine), vitamin $B_2$ (ribotlavin), vitamin $B_3$ (nicotinic acid or nicotinamid), vitamin $B_5$ (panthothenic acid and panthenol), vitamin $B_6$ (5-hydroxymethyl-2-methylpyridin-3-ol, also known as pyridoxine, pyridoasamine or pyridoxal) and vitamin $B_7$ (biotin). Examples of dyes include, but are not limited to, food dyes, semi-permanent dyes, permanent dyes, reactive dyes, and oxidation dyes. Useful dyes are for example described in Rowe Colour Index, $3^{rd}$ edition, Society of Dyers and Colourists, Bradford, England, 1971. The use of the self-assembling protein particularly allows the gluing of tattoos such as temporary tattoos on skin surfaces.

In addition, the cosmetic compounds may be proteins, particularly glycoproteins or lipoproteins, fragrances, stem cells, infrared-reflective compounds, infrared-absorbent compounds, mixtures of infrared-reflective compounds and infrared-absorbent compounds, argan oils, hyaluronic acids, sea silt extracts, gelee royale, gold extracts, medihoney, sacha inchi-oils, or allatonins.

More preferably, the cosmetic compounds are dyes, fragrances, stem cells, enzymes, vitamins, UV protective agents, or antioxidants.

As mentioned above, the self-assembling polypeptide is used to glue one or more cosmetic compounds on skin, mucosa, and/or hair. The skin may be selected from the group consisting of facial skin, the skin of the arms (e.g. upper or under arms), the skin of the feet, and the skin of the legs, the mucosa may be selected from the group consisting of oral mucosa, nasal mucosa, lingual mucosa, labial mucosa, and palatal mucosa, and/or the hair may be selected from the group consisting of scalp hair, eyelashes, the hair of the arms, the hair of the feet, the hair of the legs, facial hair, and pubic hair.

The self-assembling polypeptide may be used as part of a composition such as an aqueous solution having a temperature of 20° C. and a pH of between 4.5 and 7.0 such as of between 4.5 and 6.5, between 4.8 and 5.9, or of between 5.4 and 5.9 in order to glue one or more cosmetic compounds on skin, mucosa, and/or hair. The adhesive effect of the self-assembling polypeptide can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide can be improved by decreasing the pH of the composition such as aqueous solution by 0.1 to 2.5 pH units, e.g. by 0.1 to 0.5 pH units, below the pH of the skin, mucosa, and/or hair to be treated. The skin, mucosa, and/or hair to be treated may have a pH of between 4.5 and 7.0 such as of between 4.5 and 6.5, of between 4.8 and 5.9, or of between 5.4 and 5.9.

The third aspect of the present invention, as described above, can alternatively be worded as follows: In a third aspect, the present invention relates to a method of using a self-assembling polypeptide to glue one or more cosmetic compounds on skin, mucosa, and/or hair.

In a fourth aspect, the present invention relates to a self assembling polypeptide for use in gluing one or more pharmaceutical compounds on tissue, skin, mucosa, and/or hair.

As to the definition of the term "self-assembling polypeptide" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

The term "pharmaceutical compound", as used herein, refers to any biological or chemical substance, particularly pharmacological, metabolic, or immunological substance, which may be used in the treatment, cure, prophylaxis, prevention, or diagnosis of a pathological condition, e.g. a disease or disorder, or which may be used to otherwise enhance physical, psychical or mental well-being. Accordingly, the term "pharmaceutical compound" envisaged in the context of the present invention includes any compound with therapeutic, diagnostic, or prophylactic effects. For example, the pharmaceutical compound can be a compound that affects or participates in tissue growth, cell growth, cell differentiation, a compound that is able to invoke a biological action such as an immune response, or a compound that can play any other role in one or more biological processes. Preferably, the pharmaceutical compound is selected from the group consisting of an anti-microbial compound, such as an antibacterial compound (e.g. an antibiotic), an anti-viral compound or an anti-fungal compound, an immunosuppressive compound, an anti-inflammatory compound, an anti-allergic compound, an anti-coagulant, an anti-rheumatic compound, an anti-psoriatic compound, a sedative compound, a muscle relaxant, an anti-migraine compound, an anti-depressant, an insect repellent, a growth factor, a hormone, a hormone antagonist, an antioxidant, a protein, such as a glycoprotein, lipoprotein, or an enzyme (e.g. hyaluronidases), a polysaccharide, a free radical scavenger, a radiotherapeutic compound, a photodynamic therapy compound, a dye such as a fluorescent dye, and a contrast agent.

As mentioned above, the self assembling polypeptide is for use in gluing one or more pharmaceutical compounds on tissue, skin, mucosa, and/or hair. The tissue may be selected from the group consisting of connective tissue, muscle tissue, nervous tissue, epithelial tissue, and combinations thereof (e.g. multiple (different) tissues such as from an organ, for example, stomach, small intestine, large intestine, bowel, rectum, oesophagus, lung, spleen, brain, heart, kidney, liver, skin, adrenal glands, lymph and thyroid glands, eye, or pancreas), the skin may be selected from the group consisting of facial skin, the skin of the arms (e.g. upper or under arms), the skin of the feet, and the skin of the legs, the mucosa may be selected from the group consisting of oral mucosa, nasal mucosa, lingual mucosa, labial mucosa, palatal mucosa, alveolar mucosa, bowel mucosa, bronchial mucosa, gastric mucosa, intestinal mucosa, ruminal mucosa and stomach mucosa, and/or the hair may be selected from the group consisting of scalp hair, eyelashes, the hair of the arms, the hair of the feet, the hair of the legs, facial hair, and pubic hair. Particularly, the tissue may be a peri-operative or post-operative tissue.

The self-assembling polypeptide may be used as part of a composition such as an aqueous solution having a temperature of 20° C. and a pH of between 4.5 and 7.0 such as of between 4.5 and 6.5, between 4.8 and 5.9, or of between 5.4 and 5.9 in order to glue one or more pharmaceutical compounds on tissue, skin, mucosa, and/or hair. The adhesive effect of the self-assembling polypeptide can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide can be improved by decreasing the pH of the composition such as aqueous solution by 0.1 to 2.5 pH units, e.g. by 0.1 to 0.5 pH units, below the pH of the tissue, skin, mucosa, and/or hair to be treated. The tissue, skin, mucosa, and/or hair to be treated may have a pH of between 4.5 and 7.0 such as of between 4.5 and 6.5, of between 4.8 and 5.9, or of between 5.4 and 5.9.

The fourth aspect of the present invention, as described above, can alternatively be worded as follows: In a fourth aspect, the present invention relates to a method of using a self-assembling polypeptide to glue one or more pharmaceutical compounds on tissue, skin, mucosa, and/or hair.

In a fifth aspect, the present invention relates to an application combination (or simply to a combination) comprising
i) a self-assembling polypeptide, and
ii) a factor enhancing self-assembly
for use as tissue adhesive.

The term "application combination", as used herein, refers to a combination of at least two components, a self-assembling polypeptide and a factor enhancing self-assembly, which can be applied to surfaces to be glued. The application combination may be applied to tissue to function as tissue adhesive, particularly to (re)connect tissue layers with each other (see fifth and sixth aspect of the present invention). It may also be applied to skin, mucosa, and/or hair to glue one or more cosmetic compounds to these surfaces (see seventh aspect of the present invention) or to tissue, skin, mucosa, and/or hair to glue one or more pharmaceutical compounds to these surfaces (see eighth aspect of the present invention).

As to the definition of the terms "self-assembling polypeptide", "self assembly", and "tissue adhesive", it is referred to the first aspect of the present invention. The tissue is preferably selected from the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, adrenal glands, lymph and thyroid glands, eye, or pancreas, is, for example, comprised of multiple (different) tissues. As to the preferred embodiments of the "self-assembling polypeptide", particularly silk polypeptide, elastin, collagen, or keratin, it is also referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

The term "a factor enhancing self-assembly", as used herein, refers to a molecule which enhances the process in which a disordered system of pre-existing polypeptides forms an organised structure or pattern as a consequence of specific, local interactions (e.g. van der Waals forces, hydrophobic interactions, hydrogen bonds, and/or salt-bridges, etc.) among the polypeptides themselves. It particularly enhances this process by accelerating self-assembly. The change from a disordered system to an organised structure or pattern during self-assembly is characterized by a transition from a fluid state to a gelatinous and/or solid state and a corresponding increase in viscosity. The transition from a fluid to a gelatinous state can be monitored, for example, by measurement of light scattering, rheology, or Circular Dichroism (CD). The transition from a fluid to a solid state can be monitored, for example, by optical methods. These techniques are known to the skilled person. Preferably, the factor enhancing self-assembly is selected from the group consisting of alcohols, sulfates, phosphates, and a cross-linking agent.

The term "cross-linking" agent refers to a compound which is able to form chemical links between molecular chains such as protein chains to build a three-dimensional network of connected molecules such as proteins. Preferably, the cross-linking agent has the following formula (I):

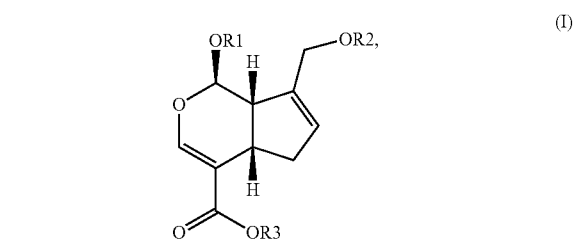

wherein
R1 is selected from the group consisting of H, $C_1$ to $C_6$ alkyl, preferably $C_1$ to $C_4$ alkyl, $C_1$ to $C_6$ hydroxyalkyl, preferably $C_1$ to $C_4$ hydroxyalkyl, and $CH_2$—C(O)O—R4, wherein R4 is $C_1$ to $C_4$ alkyl,
R2 is selected from the group consisting of H, $C_1$ to $C_6$ alkyl, preferably $C_1$ to $C_4$ alkyl, $C_1$ to $C_6$ hydroxyalkyl, preferably C, to $C_4$ hydroxyalkyl, and $CH_2$—C(O)O—R4, wherein R4 is $C_1$ to $C_4$ alkyl, and
R3 is selected from the group consisting of H, $C_1$ to $C_6$ alkyl, preferably $C_1$ to $C_4$ alkyl, more preferably $CH_3$, and $C_1$ to $C_6$ hydroxyalkyl, preferably $C_1$ to $C_4$ hydroxyalkyl. It is particularly preferred that R1 and R2 are identical, e.g. that R1 and R2 are H, and/or that R3 is H or $CH_3$. More preferably, the cross-linking agent is genipin having the following formula (II):

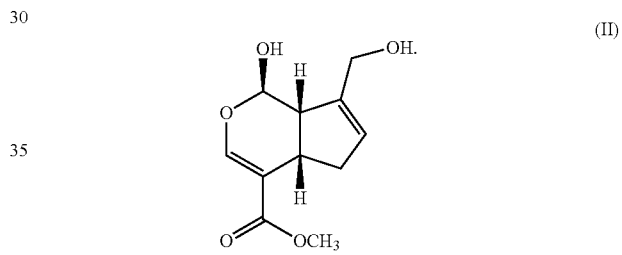

Genipin is a chemical compound found in *gardenia* fruit extract. It is an aglycone derived from an iridoid glycoside called geniposide present in fruit of *Gardenia iasminoides*. Genipin is an excellent natural cross-linker for proteins. It enhances or facilitates self-assembly of polypeptides such as silk polypeptides.

It is preferred that the self-assembling polypeptide and the factor enhancing self-assembly are consecutively or simultaneously applied. For consecutive applications, the self-assembling polypeptide may be applied first and the factor enhancing self-assembly may be applied afterwards, or the factor enhancing self-assembly may be applied first and the self-assembling polypeptide may be applied afterwards. For example, the first component (e.g. the self-assembling polypeptide or the factor enhancing self-assembly) is spread on the tissue area, e.g. wound, and then the second component (e.g. the factor enhancing self-assembly or the self-assembling polypeptide) is spread on the same tissue area, e.g. wound. For simultaneous applications, the self-assembling polypeptide and the factor enhancing self-assembly may be applied at the same time, preferably comprised in a two component application combination device or in form of a two component application combination. For example, the two components (i.e. the self-assembling polypeptide and the factor enhancing self-assembly) of the two component application combination device are spread simultaneously on the tissue area, e.g. wound. The two component application combination device may include two separate syringes, one may be filled with the self-assembling polypeptide and one may be filled with the factor enhancing self-assembly. A dual syringe two component application combination device may also be used.

It is further preferred that
i) the self-assembling polypeptide is comprised in a composition, and/or
ii) the factor enhancing self-assembly is comprised in a composition.

The composition may be a solid composition such as a powdery composition, a liquid composition such as an aqueous composition, e.g. an aqueous solution, an emulsion, or a suspension, an aerosol such as a dry or liquid aerosol, a pump spray, or a pasty composition. Preferably, the composition comprising the self-assembling polypeptide and the composition comprising the factor enhancing self-assembly are of the same type. More preferably, the self-assembling polypeptide is comprised in a liquid composition, particularly in an aqueous composition, e.g. an aqueous solution, and/or the factor enhancing self-assembly is comprised in a liquid composition, particularly aqueous composition, e.g. aqueous solution.

It is particularly preferred that the composition comprising the self-assembling polypeptide and/or the composition comprising the factor enhancing self-assembly further comprises one or more pharmaceutical compounds. The term "pharmaceutical compound" is defined above. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof.

In preferred embodiments of the invention, the application composition comprising the self-assembling polypeptide and the factor enhancing self-assembly, as described herein, is for use as tissue adhesive
i) in the treatment of a wound,
ii) in the treatment of a sutured wound,
iii) in the reduction or prevention of fibrosis, particularly capsular fibrosis, and/or in the reduction or prevention of scarring,
iv) in the fixation of transplants, preferably tissue transplants or organ transplants, more preferably skin transplants,
v) in the fixation of medical devices, preferably implants, more preferably silicone implants or implants with a silicone surface, and/or
vi) in surgical interventions.

As to the definition of the terms "wound" and "medical devices" and as to the preferred embodiments of the "wounds", "sutured wounds", "transplants", "medical devices", "implants", and "surgical interventions", it is referred to the first aspect of the present invention.

The fifth aspect of the present invention, as described above, can alternatively be worded as follows: In a fifth aspect, the present invention relates to a method of using an application combination comprising a self-assembling polypeptide and a factor enhancing self-assembly as tissue adhesive.

In a sixth aspect, the present invention relates to the use of an application combination (or simply of a combination) comprising
i) a self-assembling polypeptide, and
ii) a factor enhancing self-assembly
as tissue adhesive.

The use may be an in vivo, in vitro, or ex vivo use, preferably an in vitro or ex vivo use. As to the definition of the terms "self-assembling polypeptide", "self assembly", and "tissue adhesive", it is referred to the first aspect of the present invention. The tissue is preferably selected from the group consisting of connective tissue, muscle tissue, nervous tissue, epithelial tissue, and combinations thereof, e.g. multiple (different) tissues. An organ, e.g. stomach, small intestine, large intestine, bowel, rectum, oesophagus, lung, spleen, brain, heart, kidney, liver, skin, adrenal glands, lymph and thyroid glands, eye, or pancreas, is, for example, comprised of multiple (different) tissues. As to the preferred embodiments of the "self-assembling polypeptide", particularly "silk polypeptide", it is also referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention. Further, as to the definition of the terms "application combination", and "a factor enhancing self-assembly", it is referred to the fifth aspect of the present invention. Preferably, the factor enhancing self-assembly is selected from the group consisting of alcohols, sulfates, phosphates, and a cross-linking agent. As to the definition of the term "cross-linking agent" and as to preferred embodiments of the "cross-linking agent", it is referred to the fifth aspect of the present invention. It is particularly preferred that the cross-linking agent is genipin.

It is preferred that the self-assembling polypeptide and the factor enhancing self-assembly are consecutively or simultaneously applied. For consecutive applications, the self-assembling polypeptide may be applied first and the factor enhancing self-assembly may be applied afterwards, or the factor enhancing self-assembly may be applied first and the self-assembling polypeptide may be applied afterwards. For simultaneous applications, the self-assembling polypeptide and the factor enhancing self-assembly may be applied at the same time, preferably comprised in a two component application combination device or in form of a two component application combination. For example, the two components (i.e. the self-assembling polypeptide and the factor enhancing self-assembly) of the two component application combination device are spread simultaneously on the tissue area, e.g. wound. The two component application combination device may include two separate syringes, one may be filled with the self-assembling polypeptide and one may be filled with the factor enhancing self-assembly. A dual syringe two component application combination device may also be used.

It is further preferred that
i) the self-assembling polypeptide is comprised in a composition, and/or
ii) the factor enhancing self-assembly is comprised in a composition.

The composition may be a solid composition such as a powdery composition, a liquid composition such as an aqueous composition, e.g. an aqueous solution, an emulsion, or a suspension, an aerosol such as a dry or liquid aerosol, a pump spray, or a pasty composition. Preferably, the composition comprising the self-assembling polypeptide and the composition comprising the factor enhancing self-assembly are of the same type. More preferably, the self-assembling polypeptide is comprised in a liquid composition, particularly in an aqueous composition, e.g. an aqueous solution, and/or the factor enhancing self-assembly is comprised in a liquid composition, particularly aqueous composition, e.g. aqueous solution.

It is particularly preferred that the composition comprising the self-assembling polypeptide and/or the composition comprising the factor enhancing self-assembly further comprises one or more pharmaceutical compounds. The term "pharmaceutical compound" is defined above. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof.

As mentioned above, the present invention relates to the use of an application combination comprising a self-assembling polypeptide, e.g. silk polypeptide such as spider silk polypeptide, and a factor enhancing self-assembly as tissue adhesive. Preferably, the application combination is used to process food. In one embodiment, the application combination is used to glue tissues, preferably meat, more preferably pork, beef, chicken, or turkey.

The sixth aspect of the present invention, as described above, can alternatively be worded as follows: In a sixth aspect, the present invention relates to a method of using an application combination comprising a self-assembling polypeptide and a factor enhancing self-assembly as tissue adhesive.

In a seventh aspect, the present invention relates to the use of an application combination (or simply of a combination) comprising
  i) a self-assembling polypeptide, and
  ii) a factor enhancing self-assembly
to glue one or more cosmetic compounds on skin, mucosa, and/or hair.

As to the definition of the terms "self-assembling polypeptide" and "self-assembly" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention. Further, as to the definition of the terms "application combination", and "a factor enhancing self-assembly", it is referred to the fifth aspect of the present invention. Preferably, the factor enhancing self-assembly is selected from the group consisting of alcohols, sulfates, phosphates, and a cross-linking agent. As to the definition of the term "cross-linking agent" and as to preferred embodiments of the "cross-linking agent", it is referred to the fifth aspect of the present invention. It is particularly preferred that the cross-linking agent is genipin.

It is preferred that the self-assembling polypeptide and the factor enhancing self-assembly are consecutively or simultaneously applied. For consecutive applications, the self-assembling polypeptide may be applied first and the factor enhancing self-assembly may be applied afterwards, or the factor enhancing self-assembly may be applied first and the self-assembling polypeptide may be applied afterwards. For example, the first component (e.g. the self-assembling polypeptide or the factor enhancing self-assembly) is spread on the tissue area, e.g. wound, and then the second component (e.g. the factor enhancing self-assembly or the self-assembling polypeptide) is spread on the same tissue area, e.g. wound. For simultaneous applications, the self-assembling polypeptide and the factor enhancing self-assembly may be applied at the same time, preferably comprised in a two component application combination device or in form of a two component application combination. For example, the two components (i.e. the self-assembling polypeptide and the factor enhancing self-assembly) of the two component application combination device are spread simultaneously on the tissue area, e.g. wound. The two component application combination device may include two separate syringes, one may be filled with the self-assembling polypeptide and one may be filled with the factor enhancing self-assembly. A dual syringe two component application combination device may also be used.

It is further preferred that
  i) the self-assembling polypeptide is comprised in a composition, and/or
  ii) the factor enhancing self-assembly is comprised in a composition.

The composition may be a solid composition such as a powdery composition, a liquid composition such as an aqueous composition, e.g. an aqueous solution, an emulsion, or a suspension, an aerosol such as a dry or liquid aerosol, a pump spray, or a pasty composition. Preferably, the composition comprising the self-assembling polypeptide and the composition comprising the factor enhancing self-assembly are of the same type. More preferably, the self-assembling polypeptide is comprised in a liquid composition, particularly in an aqueous composition, e.g. an aqueous solution, and/or the factor enhancing self-assembly is comprised in a liquid composition, particularly aqueous composition, e.g. aqueous solution.

As to the definition of the term "cosmetic compound" and as to preferred embodiments of the "cosmetic compound", "skin", "mucosa", and "hair", it is referred to the third aspect of the present invention.

The seventh aspect of the present invention, as described above, can alternatively be worded as follows: In a seventh aspect, the present invention relates to a method of using an application combination comprising a self-assembling polypeptide and a factor enhancing self-assembly to glue one or more cosmetic compounds on skin, mucosa, and/or hair.

In an eighth aspect, the present invention relates to an application combination (or simply a combination) comprising
  i) a self-assembling polypeptide, and
  ii) a factor enhancing self-assembly
for use in gluing one or more pharmaceutical compounds on tissue, skin, mucosa, and/or hair.

As to the definition of the terms "self-assembling polypeptide" and "self-assembly" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention. Further, as to the definition of the terms "application combination", and "a factor enhancing self-assembly", it is referred to the fifth aspect of the present invention. Preferably, the factor enhancing self-assembly is selected from the group consisting of alcohols, sulfates, phosphates, and a cross-linking agent. As to the definition of the term "cross-linking agent" and as to preferred embodiments of the "cross-linking agent", it is referred to the fifth aspect of the present invention. It is particularly preferred that the cross-linking agent is genipin.

It is preferred that the self-assembling polypeptide and the factor enhancing self-assembly are consecutively or simultaneously applied. For consecutive applications, the self-assembling polypeptide may be applied first and the factor enhancing self-assembly may be applied afterwards, or the factor enhancing self-assembly may be applied first and the self-assembling polypeptide may be applied afterwards. For example, the first component (e.g. the self-assembling polypeptide or the factor enhancing self-assembly) is spread on the tissue area, e.g. wound, and then the second component (e.g. the factor enhancing self-assembly or the self-assembling polypeptide) is spread on the same tissue area, e.g. wound. For simultaneous applications, the self-assembling polypeptide and the factor enhancing self-assembly may be applied at the same time, preferably comprised in a two component application combination device or in form of a two component application combination. For example, the two components (i.e. the self-assembling polypeptide and the factor enhancing self-assembly) of the two component application combination device are spread simultaneously on the tissue area, e.g. wound. The two component application combination device may include two separate syringes, one may be filled with the self-assembling polypeptide and one may be filled with the factor enhancing self-assembly. A dual syringe two component application combination device may also be used.

It is further preferred that
i) the self-assembling polypeptide is comprised in a composition, and/or
ii) the factor enhancing self-assembly is comprised in a composition.

The composition may be a solid composition such as a powdery composition, a liquid composition such as an aqueous composition, e.g. an aqueous solution, an emulsion, or a suspension, an aerosol such as a dry or liquid aerosol, a pump spray, or a pasty composition. Preferably, the composition comprising the self-assembling polypeptide and the composition comprising the factor enhancing self-assembly are of the same type. More preferably, the self-assembling polypeptide is comprised in a liquid composition, particularly in an aqueous composition, e.g. an aqueous solution, and/or the factor enhancing self-assembly is comprised in a liquid composition, particularly aqueous composition, e.g. aqueous solution.

As to the definition of the term "pharmaceutical compound" and as to preferred embodiments of the "pharmaceutical compound", "tissue", "skin", "mucosa", and "hair", it is referred to the fourth aspect of the present invention.

The eighth aspect of the present invention, as described above, can alternatively be worded as follows: In an eighth aspect, the present invention relates to a method of using an application combination comprising a self-assembling polypeptide and a factor enhancing self-assembly to glue one or more pharmaceutical compounds on tissue, skin, mucosa, and/or hair.

The self-assembling polypeptide being part of the application combinations described with respect to the fifth to eight aspect of the present invention may be comprised in a composition such as an aqueous solution, and/or the factor enhancing self-assembly being part of the application combinations described with respect to the fifth to eight aspect of the present invention may be comprised in a composition such as an aqueous solution having a temperature of 20° C. and a pH of between 4.5 and 7.0 such as of between 4.5 and 6.5, between 4.8 and 5.9, or of between 5.4 and 5.9. The application combinations comprising the self-assembling polypeptide and the factor enhancing self-assembly may be applied to tissue, skin, mucosa, and/or hair. The adhesive effect of the self-assembling polypeptide and/or the factor enhancing self-assembly can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide and/or factor enhancing self-assembly can be improved by decreasing the pH of the composition such as aqueous solution by 0.1 to 2.5 pH units, e.g. by 0.1 to 0.5 pH units, below the pH of the tissue, skin, mucosa, and/or hair to be treated. The tissue, skin, mucosa, and/or hair to be treated may have a pH of between 4.5 and 7.0 such as of between 4.5 and 6.5, of between 4.8 and 5.9, or of between 5.4 and 5.9.

In a ninth aspect, the present invention relates to a self-assembling polypeptide for use as organ protection and/or organ isolation material. As to the definition of the term "self-assembling polypeptide" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

Preferably, the organ is a sense organ, preferably selected from the group consisting of skin, eye, ear, nose, and mouth.

The inventors of the present invention surprisingly found that the self-assembling polypeptide is suitable to protect and/or isolate an organ, preferably a sense organ (e.g. skin or eye), particularly from its environment, as environmental factors, for example, might influence and/or irritate an organ (e.g. skin or eye), or area surrounding it. Examples of environmental factors include, but are not limited to, microorganisms such as bacteria, viruses and fungi (can cause infections or inflammations), fine dust and fine particle (comprised in the air), and foreign matter. Its suitability, for example, has been demonstrated in the safety tests (e.g. acute eye irritation study, immunogenicity test, acute systemic toxicity test, and acute skin irritability test) described in the experimental section.

The organ may comprise an affected area, particularly an infected, inflamed or injured area, e.g. a wound. Preferably, the wound is selected from the group consisting of an abrasion, a burn, sunburn, scratch, scrap, an ulcer, a topical wound, an open wound, and a wound caused by heat, an electric current, chemicals (e.g. acids and/or bases), a biological agent, an inflammation or an infection.

It is preferred that the self-assembling polypeptide seals the affected area, particularly the infected, inflamed or injured area, e.g. the wound, comprised in the organ. The affected area may be a region of the skin, where the skin is damaged or missing. It is thereby advantageous that the self-assembling polypeptide, particularly silk polypeptide such as spider silk polypeptide, does not form an insurmountable barrier so that the protected and/or isolated sites can be entered and passed by cells as well as oxygen and water. For example, the cells comprised in the affected area can migrate, the affected tissue can be rebuilt, and/or the affected tissue can be reconnected. Furthermore, the self-assembling polypeptide, particularly silk polypeptide such as spider silk polypeptide, has the advantage that it is flexible which reduces or even abolishes the tensile force acting on the affected area, e.g. wound. In addition, the self-assembling polypeptide prevents drying out of the isolated and/or protected organ.

In preferred embodiments, the self-assembling polypeptide covers or coats the organ to be isolated and/or protected, for example, the affected area, particularly infected, inflamed or injured area, e.g. the wound, comprised in the organ.

The self-assembling polypeptide may be provided in several preferential compositions including, but not limited to, solid compositions such as powdery compositions, liquid compositions such as aqueous compositions, e.g. aqueous solutions, emulsions, or suspensions, aerosols such as dry or liquid aerosols, pump sprays, and pasty compositions. These compositions comprising the self-assembling polypeptide may additionally comprise one or more pharmaceutical compounds such as therapeutic or diagnostic compounds. Thus, for example, a liquid composition (e.g. aqueous composition) comprising the self-assembling polypeptide and optionally further comprising one or more pharmaceutical compounds is applied to the organ to be protected and/or isolated, for example, the affected area, particularly infected, inflamed or injured area, e.g. the wound, comprised in the organ.

The self-assembling polypeptide may further be provided as film, gel, particularly hydrogel, foam, mesh, scaffold, patch, nonwoven, or layer, particularly covering or coating layer. The film, gel, particularly hydrogel, foam, mesh, scaffold, path, nonwoven, or layer, particularly covering or coating layer, comprising the self-assembling polypeptide may additionally comprise one or more pharmaceutical compounds. Thus, for example, a film, gel, particularly hydrogel, foam, mesh, scaffold, patch, nonwoven, or layer, particularly covering or coating layer, comprising the self-assembling polypeptide and optionally further comprising one or more pharmaceutical compounds is applied to the organ to be protected and/or isolated, e.g. the affected area, particularly infected, inflamed or injured area, e.g. the wound, comprised in the organ.

The self-assembling polypeptide may also be applied to several preferential objects including, but not limited to, meshes, scaffolds, patches, nonwovens, and implants, for example, dental implants, microchip implants, soft tissue implants such as silicone implants, or implants with a silicone surface (e.g. cochlea implants). Due to this application, the objects including, but not limited to, meshes, scaffolds, patches, implants for example, dental implants, microchip implants, soft tissue implants such as silicone implants, or implants with a silicone surface (e.g. cochlea implants), and nonwovens may be covered or coated, e.g. partially or completely covered or coated, with the self-assembling polypeptide. It can be applied to these objects via dip-coating, spraying, or dropping. For dip-coating, preferential objects are dipped into liquid compositions such as aqueous compositions, e.g. aqueous solutions, comprising the self-assembling polypeptide. Further, for spraying, liquid compositions such as aqueous compositions, e.g. aqueous solutions, comprising the self-assembling polypeptide are sprayed onto preferential objects. Furthermore, for dropping, liquid compositions such as aqueous compositions, e.g. aqueous solutions, comprising the self-assembling polypeptide are dropped onto preferential objects. These liquid compositions comprising the self-assembling polypeptide may additionally comprise one or more pharmaceutical compounds such as therapeutic or diagnostic compounds. Thus, for example, a mesh, scaffold, patch, nonwoven, or implant coated and/or immersed with the self-assembling polypeptide and optionally further coated and/or immersed with one or more pharmaceutical compounds is applied to the organ to be protected and/or isolated, e.g. the affected area, particularly infected, inflamed or injured area, e.g. the wound, comprised in the organ.

The term "pharmaceutical compound", as used herein, is defined above. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof.

The ninth aspect of the present invention, as described above, can alternatively be worded as follows: In a ninth aspect, the present invention relates to a method of using a self-assembling polypeptide as organ protection and/or isolation material.

In a further aspect, the present invention relates to the use of a self-assembling polypeptide as organ protection and/or isolation material. As to the definition of the term "self-assembling polypeptide" and as to preferred embodiments of the "self-assembling polypeptide", particularly silk polypeptide, elastin, collagen, or keratin, it is referred to the first aspect of the present invention. For example, it is preferred that the self-assembling polypeptide further comprises at least one peptide which is capable of enhancing the adhesive effect. It is further preferred that the adhesive effect is mediated via binding of the peptide to a cell adhesion mediating protein (CAMP). It is also, additionally or alternatively, preferred that the peptide comprises at least one CAMP recognition sequence. As to the definition of the terms "peptide", "peptide which is capable of enhancing the adhesive effect", "cell adhesion mediating protein (CAMP)", and "cell adhesion" and as to preferred embodiments of the "peptide", "peptide which is capable of enhancing the adhesive effect", "cell adhesion mediating protein", "CAMP recognition sequence", it is referred to the first aspect of the present invention.

Preferably, the organ is a sense organ, preferably selected from the group consisting of skin, eye, ear, nose, and mouth. The organ may comprise an affected area, particularly an infected, inflamed or injured area, e.g. a wound. Preferably, the wound is selected from the group consisting of an abrasion, a burn, sunburn, scratch, scrap, an ulcer, a topical wound, an open wound, and a wound caused by heat, an electric current, chemicals (e.g. acids and/or bases), a biological agent, an inflammation or an infection.

It is preferred that the self-assembling polypeptide seals the affected area, particularly the infected, inflamed or injured area, e.g. the wound, comprised in the organ.

The affected area may be a region of the skin, where the skin is damaged or missing. In addition, the self-assembling polypeptide prevents drying out of the isolated and/or protected organ. As to other preferred embodiments, it is referred to the ninth aspect of the present invention.

It is another aspect of the present invention to provide a method of connecting two tissues by an adhesive comprising the steps of:
i) applying a self-assembling polypeptide to a first tissue, and
ii) contacting the first tissue with a second tissue, thereby connecting said two tissues.

Said tissues may particularly be tissue layers. The self-assembling polypeptide as tissue adhesive may be applied as part of a composition such as an aqueous solution having a temperature of 20° C. and a pH of between 4.5 and 7.0 such as of between 4.5 and 6.5, between 4.8 and 5.9, or of between 5.4 and 5.9 to the first tissue. The adhesive effect of the self-assembling polypeptide can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide can be improved by decreasing the pH of the composition such as aqueous solution by 0.1 to 2.5 pH units, e.g. by 0.1 to 0.5 pH units, below the pH of the tissue to be connected. The tissue to be connected may have a pH of between 4.5 and 7.0 such as of between 4.5 and 6.5, of between 4.8 and 5.9, or of between 5.4 and 5.9.

It is preferred that the method further comprises the step of applying a factor enhancing self-assembly to the first tissue. This step is preferably carried out subsequent to step i). The self-assembling polypeptide and the factor enhancing self-assembly may also be applied at the same time, e.g. comprised in a two component application combination device or in form of a two component application combination (see above), in step i). The self-assembling polypeptide may be comprised in a composition and/or the factor enhancing self-assembly may be comprised in a composition. The composition may be a solid composition such as a powdery composition, a liquid composition such as an aqueous composition, e.g. an aqueous solution, an emulsion, or a suspension, an aerosol such as a dry or liquid aerosol, a pump spray, and a pasty composition. Preferably, the composition comprising the self-assembling polypeptide and the composition comprising the factor enhancing self-assembly are of the same type. The composition comprising the self-assembling polypeptide and/or the composition comprising the factor enhancing self-assembly may comprise one or more pharmaceutical compounds. The term "pharmaceutical compound", as used herein, is defined above. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof. The self-assembling polypeptide may be dried before or after the contact with the tissue.

All aspects of the first, second, fifth, and sixth aspect of the invention also apply to this aspect of the invention.

It is also another aspect of the present invention to provide a method of filling a gap in a tissue by an adhesive comprising the steps of:
i) providing a tissue with a gap, and
ii) applying a self-assembling polypeptide to the gap in the tissue,
thereby filling the gap in the tissue.

The self-assembling polypeptide as tissue adhesive may be applied as part of a composition such as an aqueous solution having a temperature of 20° C. and a pH of between 4.5 and 7.0 such as of between 4.5 and 6.5, between 4.8 and 5.9, or of between 5.4 and 5.9 to the gap in the tissue. The adhesive effect of the self-assembling polypeptide can be improved by increasing the temperature of the composition such as aqueous solution above 20° C., e.g. from a temperature of 20° C. to 25° C., 30° C., 35° C., 37° C., 38° C., 39° C. or 40° C. Alternatively or additionally, the adhesive effect of the self-assembling polypeptide can be improved by decreasing the pH of the composition such as aqueous solution by 0.1 to 2.5 pH units, e.g. by 0.1 to 0.5 pH units, below the pH of the tissue to be treated. The tissue to be treated may have a pH of between 4.5 and 7.0 such as of between 4.5 and 6.5, of between 4.8 and 5.9, or of between 5.4 and 5.9.

It is preferred that the method further comprises the step of applying a factor enhancing self-assembly to the gap in the tissue. This step is preferably carried out subsequent to step ii). The self-assembling polypeptide and the factor enhancing self-assembly may also be applied at the same time, e.g. comprised in a two component application combination device or in form of a two component application combination (see above), in step ii). The self-assembling polypeptide may be comprised in a composition and/or the factor enhancing self-assembly may be comprised in a composition. The composition may be a solid composition such as a powdery composition, a liquid composition such as an aqueous composition, e.g. an aqueous solution, an emulsion, or a suspension, an aerosol such as a dry or liquid aerosol, a pump spray, and a pasty composition. Preferably, the composition comprising the self-assembling polypeptide and the composition comprising the factor enhancing self-assembly are of the same type. The composition comprising the self-assembling polypeptide and/or the composition comprising the factor enhancing self-assembly may comprise one or more pharmaceutical compounds. The term "pharmaceutical compound", as used herein, is defined above. Preferably, the pharmaceutical compound is selected from the group consisting of an anti-microbial compound, an anti-viral compound, an anti-fungal compound, an immunosuppressive compound, a growth factor, an enzyme, an anti-inflammatory compound, an anti-allergic compound, a sedative compound, a protein, particularly a glycoprotein or lipoprotein, a polysaccharide, and mixtures thereof. The self-assembling polypeptide may be dried before or after the contact with the tissue gap.

All aspects of the first, second, fifth, and sixth aspect of the invention also apply to this aspect of the invention.

In a further aspect, the present invention relates to a spider silk polypeptide characterized by a size of no more than 100 kDa, preferably of no more than 95 or 90 kDa, more preferably of no more than 85 or 80 kDa, even more preferably of no more than 75 or 70, most preferably of no more than 65 kDa, comprising at least one, preferably one or two, non-repetitive sequence(s) according to SEQ ID NO: 76 (NR5) or SEQ ID NO: 77 (NR6). Preferably, the spider silk polypeptide is a recombinant spider silk polypeptide. It is also preferred that the spider silk polypeptide is $C_{16}NR5$ or $C_{16}NR6$.

In another further aspect, the present invention relates to a spider silk polypeptide consisting of no more than 1000 amino acids, preferably of no more than 950 amino acids, more preferably of no more 900 amino acids, even more preferably of no more than 850 amino acids, most preferably of no more than 800 or 750 amino acids, comprising at least one, preferably one or two, non-repetitive sequence(s) according to SEQ ID NO: 76 (NR5) or SEQ ID NO: 77 (NR6). Preferably, the spider silk polypeptide is a recombinant spider silk polypeptide. It is also preferred that the spider silk polypeptide is $C_{16}NR5$ or $C_{16}NR6$.

In a further aspect, the present invention relates to an implant coated with a self-assembling polypeptide. As to the definition of the term "self-assembling polypeptide" and as to the preferred embodiments of the "self-assembling polypeptide", it is referred to the first aspect of the present invention. In particular, the self-assembling polypeptide is selected from the group consisting of a silk polypeptide such as a recombinant silk polypeptide. Preferably, the implant is a dental implant, a microchip implant, or a soft tissue implant, such as a silicone implant, or an implant with a silicone surface (e.g. a cochlea implant). The silicone implant or implant with a silicone surface may also be a breast implant. The term "coating" in this respect, refers to a covering that is comprised on the implant. The implant may be partially or completely covered or coated with the self-assembling polypeptide. Preferably, said "coating" completely covers or surrounds the implant. It is preferred that the "coating" has a thickness of between 1 nm and 50 µm, preferably 40 nm and 50 µm, more preferably between 0.5 µm and 10 µm and most preferably between 0.5 µm and 5 µm.

In a further aspect, the present invention relates to a self-assembling polypeptide for use as a coating material or to the use of a self-assembling polypeptide as a coating material. As to the definition of the term "self-assembling polypeptide" and as to the preferred embodiments of the "self-assembling polypeptide", it is referred to the first aspect of the present invention. In particular, the self-assembling polypeptide is selected from the group consisting of a silk polypeptide such as a recombinant silk polypeptide.

In another further aspect, the present invention relates to a composition comprising a self-assembling polypeptide and a factor enhancing self-assembly for use as a coating material or to the use of a composition comprising a self-assembling polypeptide and a factor enhancing self-assembly as a coating material. Preferably, the factor enhancing self-assembly is selected from the group consisting of alcohols, sulfates, phosphates, and a cross-linking agent.

The term "cross-linking" agent refers to a compound which is able to form chemical links between molecular chains such as protein chains to build a three-dimensional network of connected molecules such as proteins. As to the preferred embodiments of the "cross-linking agent", it is referred to the fifth aspect of the present invention. It is particularly preferred that the cross-linking agent is genipin.

Said composition includes, but is not limited to, a solid composition such as a powdery composition, a liquid composition such as an aqueous composition, e.g. an aqueous solution, emulsion, or suspension, an aerosol such as a dry or liquid aerosol, a pump spray, and a pasty composition. The composition comprising the self-assembling polypeptide and the factor enhancing self-assembly may additionally comprise one or more pharmaceutical compounds such as therapeutic or diagnostic compounds. Thus, for example, a liquid composition (e.g. aqueous composition) comprising the self-assembling polypeptide, the factor enhancing self-assembly and one or more pharmaceutical compounds such as therapeutic or diagnostic compounds may be used as a coating material.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The following figures and examples are merely illustrative of the present invention and should not be construed to limit the scope of the invention as indicated by the appended claims in any way.

FIGURE LEGEND

FIG. 1: Production of $C_{16}$spRGD and ntag$^{Cys}C_{16}$-c(RGDfK). (A) Chemical structure of the synthetic cyclic RGD peptide c(RGDfK)-spacer moiety-part of SMCC employed for chemical modification of ntag$^{Cys}C_{16}$. (B) eADF4 ($C_{16}$), the RGD-containing variant ntag$^{Cys}C_{16}$-c(RGDfK) (chemically modified) and $C_{16}$spRGD (genetically modified). For ntag$^{Cys}C_{16}$-c(RGDfK), c(RGDfK)-spacer moiety-part of SMCC was covalently coupled to the thiol-group of a cysteine residue of ntag$^{Cys}C_{16}$. $C_{16}$spRGD was modified by genetic engineering hybridizing a spacer and an RGD domain with eADF4 ($C_{16}$).

Figure 2:
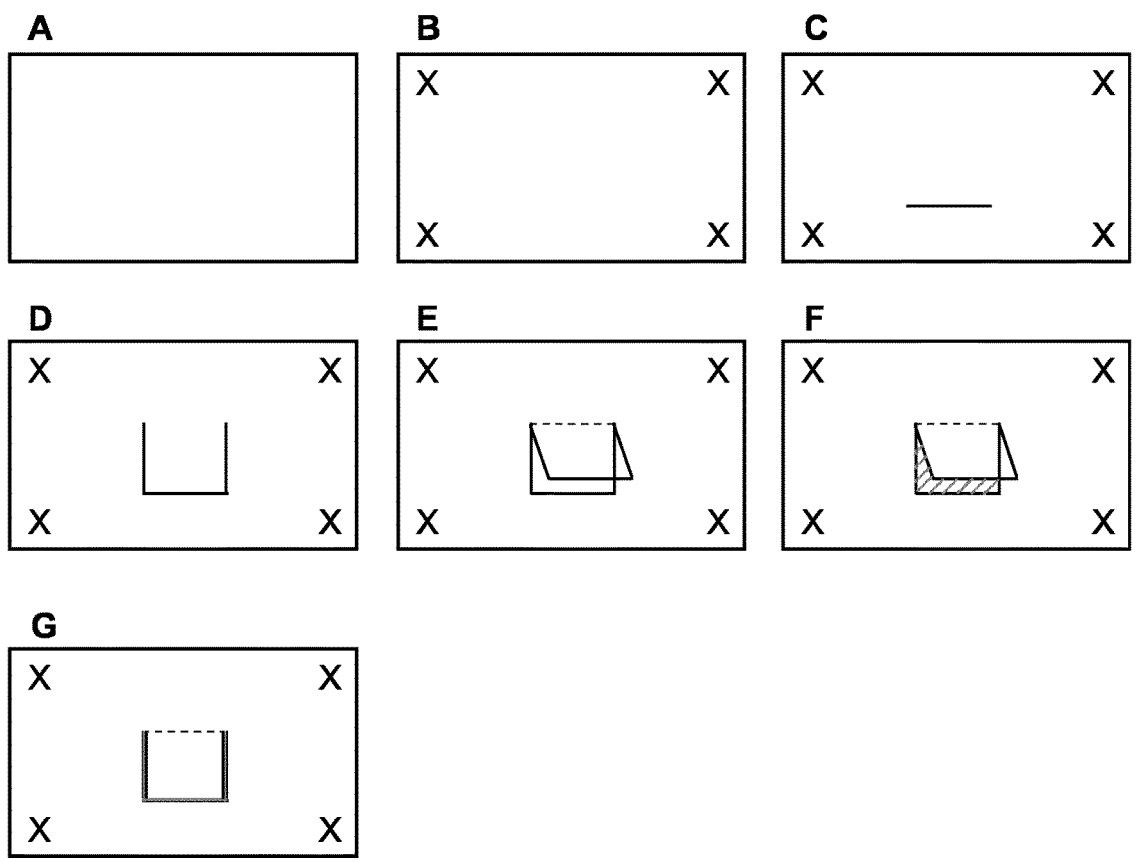

FIG. 2: Preparation of the pig skin and application of the $C_{16}$ or $C_{16}$spRGD solution to the pig skin for the adhesive test. (A) Pig skin was used for the adhesive test. The pig skin was cut into pieces having a size of about 9.5×11.0 cm (a size which fits in a Petri dish having a diameter of 14.5 cm) using a scalpel. (B) The pieces were fixed at their edges with nails onto a board to tighten the skin. (C) and (D) Three incisions per piece of skin were made according to an exemplary sample of 1 cm×1 cm using a scalpel. (E) The resulting skin graft was subsequently lifted with tweezers and cut to produce a skin pocket. (F) The $C_{16}$ or $C_{16}$spRGD solution was dropped on the cutting area using a pipette (at low protein concentrations of <40 mg/ml) or spread on the cutting area using a spatula (at high protein concentrations of ≥40 mg/ml) to cover the surface of the "wound". (G) The separated skin flap was subsequently repositioned on the cutting area.

Figure 3:
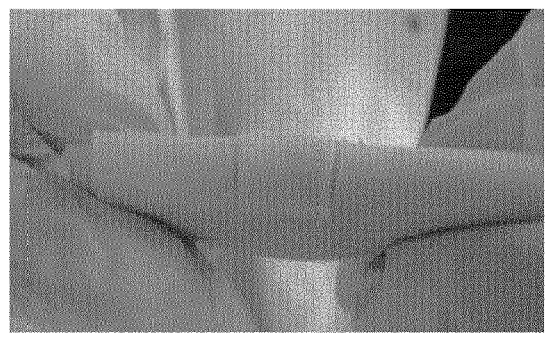
Figure 3:
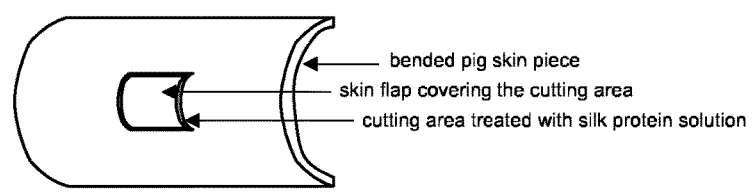
Figure 3:
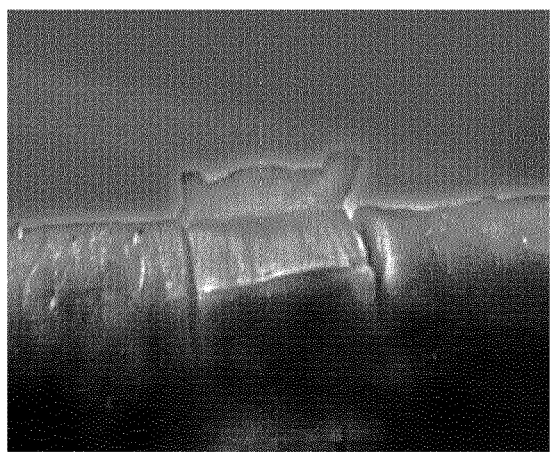
Figure 3:
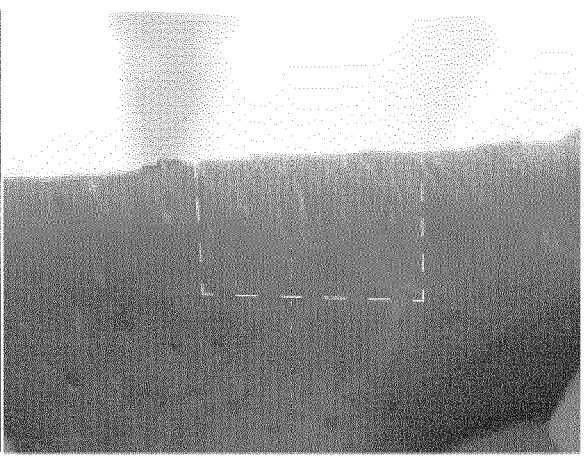

FIG. 3: Adhesive test. The adhesive effect of $C_{16}$ or $C_{16}$spRGD was tested by bending (e.g. rolling) the pig skin piece as prepared above (see FIG. 2). The bending (e.g. rolling) was carried out in order to apply tension to the "wound". (A) Photographic picture of a bended pig skin piece comprising a cutting area treated with a $C_{16}$ solution. The skin flap remained connected to the treated cutting area. (B) Schematic picture of the bended pig skin piece as shown in (A). (C) Shows a skin flap before the application of a $C_{16}$spRGD solution and (D) Shows a skin flap after application of a $C_{16}$spRGD solution (concentration: 40 mg/ml and incubation time: 1 hour). The dotted line represents the cutting edges of the skin flap.

Figure 4:
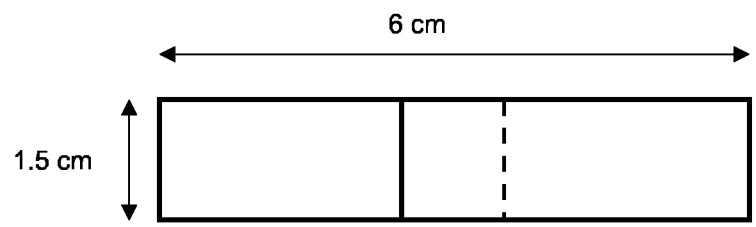
Figure 4:
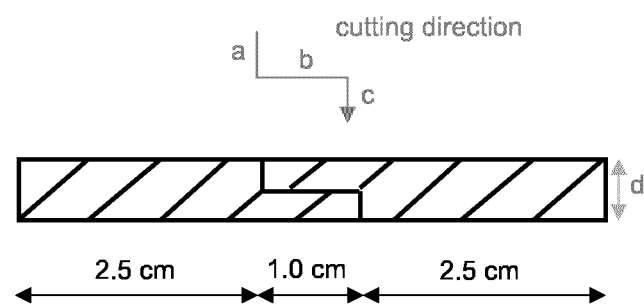
Figure 4:
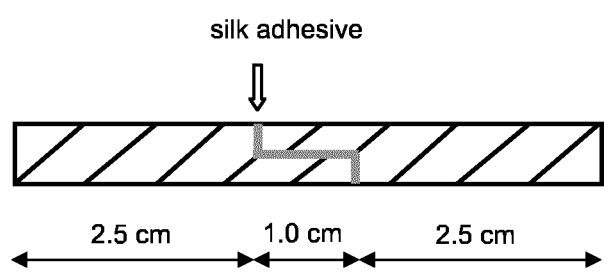

FIG. 4: Preparation of the pig skin and application of the $C_{16}$ or $C_{16}$spRGD solution to the pig skin for the pulling test. (A) Pig skin was used for the pulling test. Pig skin stripes having a size of 1.5 cm×6 cm were generated. One vertical incision of 1.5 cm in length was made at a distance of 2.5 cm from the short end of the stripe using a scalpel (see continuous line within the pig skin stripe). (B) The incision was terminated at half of the thickness (the thickness is marked with a "d") of the pig skin piece (see incision marked with "a"). The incision was continued horizontally for 1 cm (see incision marked with "b") before turning in vertical direction to cut the tissue (see incision marked with "c"). The incision to cut the tissue is also indicated as dotted line within the pig skin stripe in (A). (C) The cutting areas/surfaces of the produced two pig skin strip halves were coated with a $C_{16}$ or $C_{16}$spRGD solution.

Figure 5:
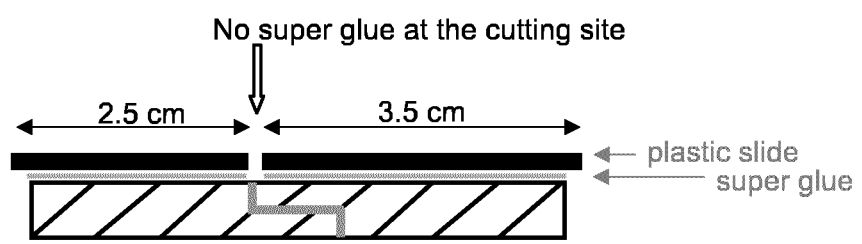
Figure 5:
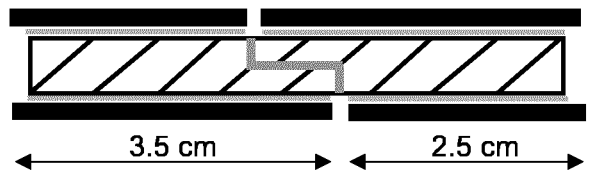
Figure 5:
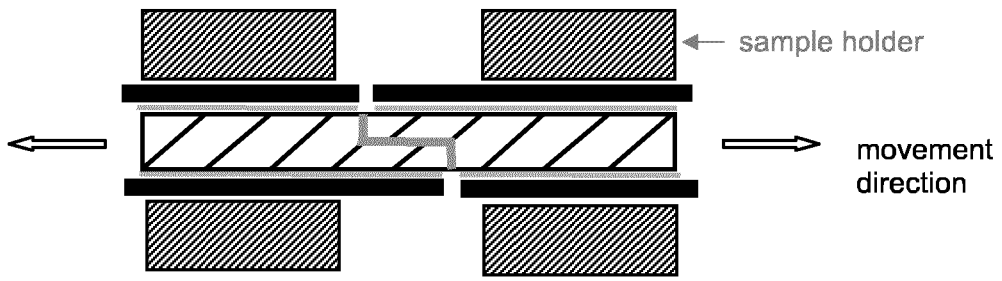

FIG. 5: (A) a super glue (e.g. "UHU Kunststoff Spezialsekundenkleber") was applied to the skin side of the stripe. The super glue was spread using a spatula or cell scraper. No glue was applied in near vicinity of the cutting site. Plastic slides (e.g. "Rinzle plastic micro-slides") having a length of 2.5 and 3.5 cm were subsequently connected with the glued site of the skin stripe (the slide having a length of 2.5 cm was positioned on the short site of the skin slide and the slide having a length of 3.5 cm was positioned on the longer site of the skin slide). (B) The same was done for the side opposite to the skin side of the stripe. (C) The adhesion force under tangential stress was tested using a tensile tester. Therefore, the glued pig skin stripe was fixed in the tensile tester using sample holders. The arrows indicate the direction of movement.

Figure 6:
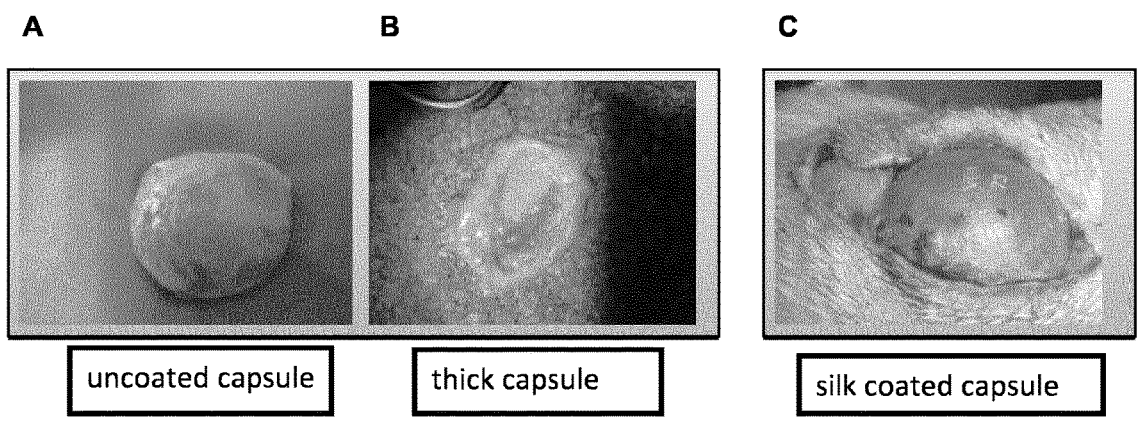

FIG. 6: Visual analysis of silk protein coated or uncoated implants after submuscular implantation in the back of rats. (A) and (B) The uncoated implants showed capsular fibrosis. (C) The capsular fibrosis in the silk protein coated implants was strongly reduced (the capsule was thinner). In addition, no scarring was visible.

Figure 7:
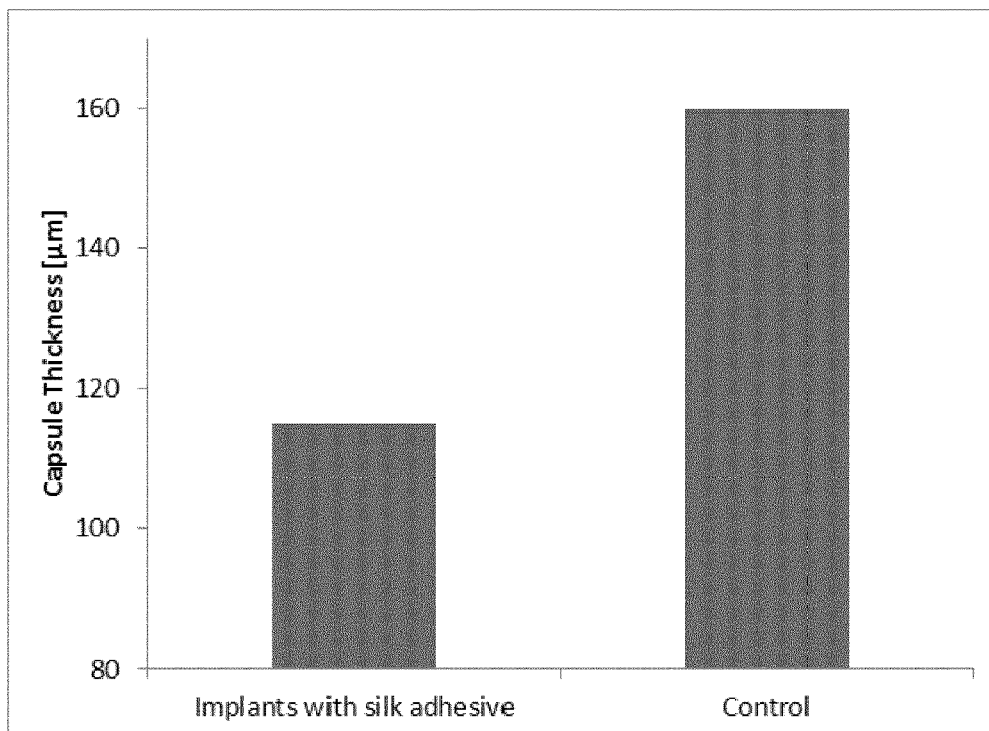

FIG. 7: Comparison of the capsule thickness: implants coated with the silk adhesive and non-coated implants (control).

Figure 8:
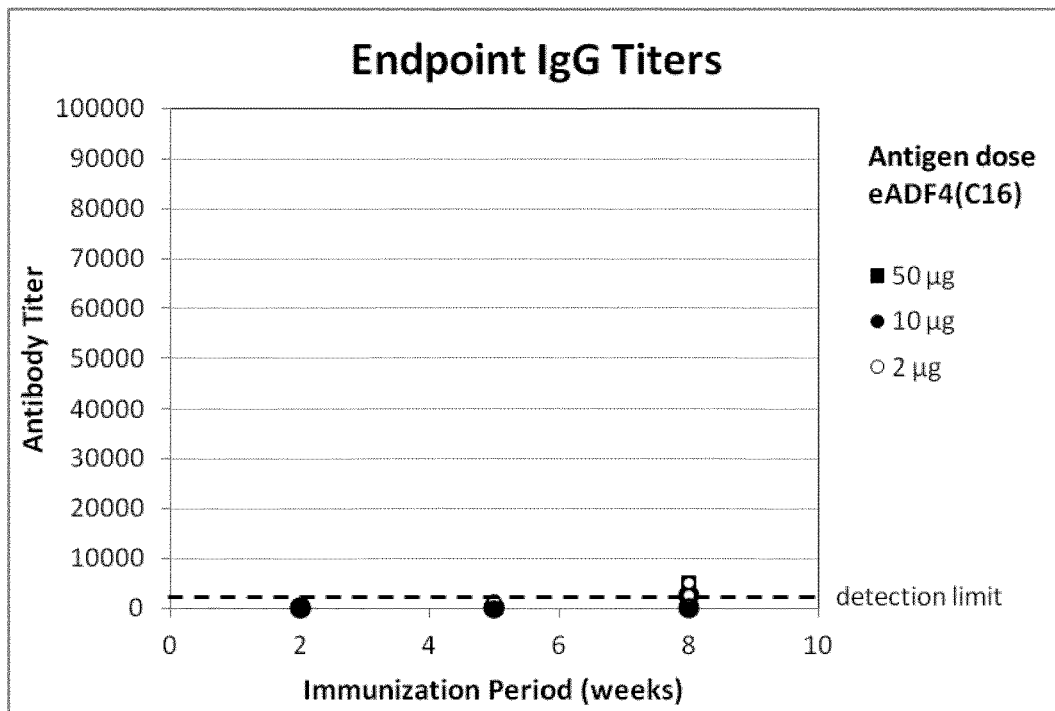

FIG. 8: Immunogenicity test. Endpoint IgG titers 2, 5 and 8 weeks after administration of eADF4 ($C_{16}$). The entire group of five mice showed no or no significant increase of IgG and therefore no or no significant specific antibody formation.

EXAMPLES

1. Production of eADF4 ($C_{16}$), $C_{16}$spRGD, and ntagCys$C_{16}$-c(RGDfK)
1.1 Production of eADF4 ($C_{16}$)

The recombinant spider silk protein eADF4 (also designated as $C_{16}$ herein) is based on the consensus sequence of one of three spidroins of the dragline silk of the European garden spider (*Araneus diadematus*). The consensus motif (C module) of ADF4 (GSSAAAAAAAASGPGGYGPEN-QGPSGPGGYGPGGP (SEQ ID NO: 21)) is repeated 16 times in the recombinant protein (FIG. 1B). For detection, an N-terminal T7-tag may be attached to the molecule. Production in *E. coli* and purification was performed as described in WO 2011/120690 A2 ("Separation of insoluble target proteins").

1.2 Genetic Modification of eADF4 ($C_{16}$)

DNA cassettes encoding RGD and a spacer sequence were created by annealing two synthetic oligonucleotides. For the RGD-tag: GATCCATGGGCGGTCGTGGTG ACTCTCCGGGTTAATGAA (SEQ ID NO: 72) and AGCTTTCATTAACCCGGAGAGTCACCACGACCGC-CCATG (SEQ ID NO: 73) and for the spacer sequence: GATCCATGGGCGGTGGCTCTGGTTAATGAA (SEQ ID NO: 74) and AGCTTT CATTAACCAGAGCCACCGC-CCATG (SEQ ID NO: 75) were used. The resulting amino acid sequence for the specific tag spRGD was GGSGGRGDSPG (SEQ ID NO: 53) (FIG. 1B). The insertion of the DNA sequences into the cloning vector and the ligation with the gene encoding eADF4 ($C_{16}$) were accomplished by a seamless cloning strategy as described previously by Huemmerich et al. ("Primary structure elements of spider dragline silks and their contribution to protein solubility", Biochemistry, 2004, 43: 13604-12). The DNA sequence of the genetically engineered $C_{16}$spRGD was confirmed by sequencing. Protein production and purification procedures were identical to that of eADF4 ($C_{16}$) (see above). A sequence of the genetically engineered $C_{16}$spRGD including a T7 Tag is shown in SEQ ID NO: 78.

1.3 Chemical Coupling of RGD to a Cysteine-Modified Variant of eADF4 ($C_{16}$)

For high coupling specificity, chemical coupling of RGD peptides was performed with the cysteine containing eADF4 ($C_{16}$) variant ntagCe$C_{16}$ which has been previously established by Spiess et al. ("Structural characterization and functionalization of engineered spider silk films", Soft Matter, 2010, 6: 4168-74) (FIG. 1B) (ntag$^{Cys}$, also designated as TAG$^{CYS3}$ herein, has a sequence according to SEQ ID NO: 37, and $C_{16}$ comprises 16 times module C having a sequence according to SEQ ID NO: 21). For coupling of the cyclic RGD c(RGDfK)-spacer moiety-part of SMCC (SMCC=Succinimidyl-4-(N-maleimidomethyl)cyclo-hexane-1-carboxylate) (see Peptides International, Louisville, Ky., USA) (see also Pierschbacher and Ruoslahti, "Influence of stereochemistry of the sequence Arg-Gly-Asp-Xaa on binding specificity in cell adhesion", J Biol Chem, 1987, 262: 17294-8; Haubner et al. "Stereoisomeric peptide libraries and peptidomimetics for designing selective inhibitors of the alpha(V)beta(3) integrin for a new cancer therapy", Angew. Chem. Int. Edit., 1997, 36: 1375-89; and Aumailley et al. "Arg-Gly-Asp constrained within cyclic pentapeptides, Strong and selective inhibitors of cell adhesion to vitronectin and laminin fragment P1", FEBS Lett, 1991, 291: 50-4) (FIG. 1A), lyophilized ntag$^{Cys}C_{16}$ was dissolved in 6 M guanidinium thiocyanate (GdmSCN), dialyzed against 20 mM HEPES, pH 7, and diluted to a final concentration of 2 mg/ml. For reduction of disulfide bonds, proteins were incubated in a ten-fold excess of tris(2-carboxyethyl)phosphine (TCEP) for 2 h at RT. After addition of a twenty-fold excess of c(RGDfK)-spacer moiety-part of SMCC, the reaction of maleimide and free thiol-groups was carried out for 2 h at RT. The protein was purified by precipitation with potassium phosphate (pH 8) at a final concentration of 1 M, followed by washing the pellet three times with deionized water.

2. Preparation of the Silk Protein Solution $C_{16}$ and $C_{16}$spRGD have been produced as described above. Respective amounts of $C_{16}$ and $C_{16}$spRGD were dissolved in 6M Guanidinium thiocyanate and dialyzed for at least 3 days at 4° C. against 5 mM Tris, pH 9. After dialysis, the samples were centrifuged for 15 min at 14.000 rpm at 4° C. Then the protein concentration was estimated by UV-Vis spectrometer. The protein solutions were diluted with 5 mM Tris solution, pH 9 to the requested concentrations.

3. Adhesive Test 3.1 Preparation of Skin

Pig skin was used for the adhesive test. The pig skin was cut into pieces having a size of about 9.5×11.0 cm (a size which fits in a Petri dish having a diameter of 14.5 cm) using a scalpel. The pieces were fixed at their edges with nails onto a board to tighten the skin (see FIGS. 2A and B). Three incisions per piece of skin were made according to an exemplary sample of 1 cm×1 cm using a scalpel (see FIGS. 2C and D). The resulting skin graft was subsequently lifted with tweezers and cut to produce a skin pocket as shown in FIG. 2E.

3.2 Application of the Silk Protein Solution to the Skin

The $C_{16}$ or $C_{16}$spRGD solution as produced above was dropped on the cutting area using a pipette (at low protein concentrations of <40 mg/ml), or spread on the cutting area using a spatula or cell scraper (at high protein concentrations of ≥40 mg/ml) to cover the surface of the "wound" (see FIG. 2F). The separated skin flap was subsequently repositioned on the cutting area (see FIG. 2G). The cutting area may also be designated as cutting surface. The samples were incubated at 37° C.

The adhesive effect was tested by bending (e.g. rolling) the pig skin piece as prepared above (see FIGS. 3A and 3B). The bending (e.g. rolling) was carried out in order to apply tension to the "wound". If the skin flap remained connected to the cutting area treated with the $C_{16}$ or $C_{16}$spRGD solution during bending (e.g. rolling), the sample was graded as a sample showing adhesive properties. If the skin flap detached from the cutting area treated with the $C_{16}$ or $C_{16}$spRGD solution during bending (e.g. rolling), the sample was graded as a sample showing no adhesive properties.

In the following, the results of the adhesive test using pig skin pieces treated with $C_{16}$spRGD solutions having a concentration of 30, 40, 50, and 70 m g/ml (see Tables 2 and 3), or $C_{16}$ solutions having a concentration of 40, 50, and 70 mg/ml (see Table 3) are shown.

TABLE 2

Results of a first $C_{16}$spRGD adhesive test with different silk protein concentrations at an incubation time of 15 min and 1 h

| $C_{16}$spRGD concentration [mg/ml] | after 15 min | after 1 h |
| --- | --- | --- |
| 30 | ✗ | ✓ |
| 40 | + | ✓ |

✗: no adhesive effect,
+: adhesive effect at the edges of the cutting surface,
✓: adhesive effect at the complete cutting surface

TABLE 3

Results of a second $C_{16}$ and $C_{16}$spRGD adhesive test with different silk protein concentrations and volumes at an incubation time of 1 h

| Volume [µl/cm²] | Concentration [mg/ml] | $C_{16}$ | $C_{16}$spRGD | References |
| --- | --- | --- | --- | --- |
| 50 | 70 | ✓ | ✓ | Ref-Tris ✗ |
|  | 50 | ✓ | ✓ | Ref ✗ |
|  | 40 | + | + |  |
| 25 | 70 | ✓ | ✓ | Ref-Tris ✗ |
|  | 50 | ✓ | ✓ | Ref ✗ |
|  | 40 | ✓ | ✓ |  |

Ref-Tris: Tris buffer
Ref: H₂O
✗: no adhesive effect,
+: adhesive effect at the edges of the cutting surface,
✓: adhesive effect at the complete cutting surface An adhesive effect of $C_{16}$ and $C_{16}$spRGD has been shown for all samples treated with $C_{16}$ and $C_{16}$spRGD solutions (concentration 40 to 70 mg/ml, volume of 50 µl/cm² and concentration 40 to 70 mg/ml, volume of 25 µl/cm²) after an incubation time of 1 hour. In each case, the skin flap remained connected to the cutting area during bending (see, for example, FIGS. 3A and B for $C_{16}$). No adhesive effect has been shown for both reference samples (Ref-Tris: cutting area treated with Tris buffer and Ref: cutting area treated with H₂O) used as negative controls. In these samples, the skin flap detached from the cutting area during bending.

FIG. 3C further shows a skin flap before the application of the $C_{16}$spRGD solution and FIG. 3D shows a skin flap after application of the $C_{16}$spRGD solution (concentration: 40 mg/ml and incubation time: 1 hour). The dotted line represents the cutting edges of the skin flap.

Similar results were achieved with pig skin pieces having the skin flap completely removed. The cutting area was covered with the $C_{16}$ and $C_{16}$spRGD solutions as described above. Afterwards, the skin flap was repositioned on the cutting area. The adhesive test was carried out as described above.

4. Pulling Test 4.1 Preparation of Skin

Pig skin was used for the pulling test. The pig skin was cut into pieces having a size of about 6.0×11.0 cm using a scalpel. The pieces were fixed at their edges with nails onto a board to tighten the skin. In a next step, pig skin stripes having a size of 1.5 cm×6 cm were cut out from the pig skin pieces (see FIG. 4A). The single pig skin stripes were further processed as follows: One vertical incision of 1.5 cm in length was made at a distance of 2.5 cm from the short end of a stripe using a scalpel (see continuous line within the pig skin stripe in FIG. 4A). The incision was terminated at half of the thickness (the thickness is marked with a "d" in FIG. 4B) of the pig skin stripe (see incision marked with "a" in FIG. 4B). The incision was continued horizontally for 1 cm (see incision marked with "b" in FIG. 4B) before turning in vertical direction to cut the tissue (see incision marked with "c" in FIG. 4B and dotted line within the pig skin stripe in FIG. 4A).

4.2 Application of the Silk Protein Solution to the Skin

The above described incision/cutting procedure separated the pig skin stripe in two halves. The pig skin stripe halves were separated from each other to treat the cutting areas with the $C_{16}$ or $C_{16}$spRGD solution as produced above. Therefore, the $C_{16}$ or $C_{16}$spRGD solution was dropped on the cutting areas using a pipette (at low protein concentrations of <40 mg/ml), or spread on the cutting areas using a spatula or cell scraper (at high protein concentrations of ≥40 mg/ml)

to cover the surface of the "wound". The two pig skin stripe halves were subsequently repositioned so that the treated cutting areas came in contact with each other (see FIG. 4C). The samples were incubated at 37° C. for 30 min.

4.3 Sample Preparation for Pulling Test

Upon expiry of the incubation time of 30 min, a super glue (e.g. "UHU Kunststoff Spezialsekundenkleber") was applied to the skin side of the stripe. The super glue was spread using a spatula or cell scraper. No glue was applied to the cutting site. Plastic slides (e.g. "Rinzle plastic microslides") having a length of 2.5 and 3.5 cm were subsequently connected with the glued site of the skin stripe (the slide having a length of 2.5 cm was positioned on the short site of the skin slide and the slide having a length of 3.5 cm was positioned on the longer site of the skin slide) (see FIG. 5A). The same was done for the side opposite to the skin side of the stripe (see FIG. 5B).

The adhesion force under tangential stress was tested using a tensile tester (e.g. Zwicki Z 0.5; Zwick Roell, 50 N load cell). Therefore, the glued pig skin stripe was fixed in the tensile tester using sample holders as shown in FIG. 5C.

The parameters of the pulling test were as follows:
Preload: 0.01 MPa
Testing speed: 10 mm/min
Clamping length at starting position: 15.00 mm
Speed tensile modulus: 10 mm/min In the following, the results of the pulling test using pig skin stripes treated with $C_{16}$spRGD or $C_{16}$ solutions having a concentration of 35 mg/ml are shown.

TABLE 4

Results of the $C_{16}$ and $C_{16}$spRGD pulling test

| Concentration [35 mg/ml] of | Incubation time | Average $\sigma_{max}$ (N) |
|---|---|---|
| $C_{16}$ | 30 min | 2.92 |
| $C_{16}$spRGD | 30 min | 5.29 |

The average maximal adhesion strength is indicated in Table 4. The maximal adhesion strength can be defined as the maximal load per unit width of the bond line required to produce progressive separation of two bonded adherents, particularly flexible adherents. The average maximal adhesion strength for $C_{16}$spRGD was increased by about 80% compared to the average maximal adhesion strength for $C_{16}$.

The above experimental data clearly demonstrate that silk proteins (e.g. $C_{16}$) or modified silk proteins (e.g. $C_{16}$spRGD) function as tissue adhesives. Thus, silk proteins can be used, for example, as tissue adhesives to treat wounds or sutured wounds.

5. Implant Coating with Silk Proteins

Textured silicone implants (Polytech Health & Aesthetics/Germany) having a diameter of 2.6 cm and a volume of 3 ml were covered with a silk protein layer of a thickness of 10 m according to the following protocol: $C_{16}$ protein was produced as described above. 1.35 g of $C_{16}$ protein was dissolved in 135 ml of 6M Guanidinium Thiocyanate under gentle agitation. 135 ml of 50 mM Tris buffer (pH 9 (Roth) 4° C.) was slowly added to obtain a homogeneous solution. The resulting protein solution was dialyzed overnight against 50 mM Tris buffer pH 9 at 4° C. Guanidinium-SCN remnants were removed via cross-flow filtration at 4° C. while Tris buffer (50 mM, pH 9) was constantly added. Subsequently the $C_{16}$ protein solution was concentrated to 60 ml. The final concentration was 10.8 mg/ml (determined by UV/Vis-Spectroscopy, Beckman Coulter, DU 800).

The coating was performed in a sterile chamber (sterilized at 140° C. for 1 hour). The silicone implants were washed with ethanol and dried at RT prior to the coating process. The silicone implants were coated 3 times with the $C_{16}$ protein solution (30 ml at 10.8 mg/ml) by dipping the silicone implants into the solution for 120 s and drying at air for 300 s, respectively. For post-treatment, the transplants were dipped in $KH_2PO_4$ solution (1M pH4 (Roth, 99%), NaCl 0.91% w/v (Roth, 99.5%)) for 120 s and dried for 120 s before washing the transplants in a saline solution (9 g/l). After sterilization by gamma-irradiation with a dose of 5 kGray (at Isotron, Allershausen), the silk protein coated implants were implanted submuscular in the back of Sprague-Dawley rats having a weight of 250 to 300 mg. As a control, uncoated implants were used.

After 3 months, the Sprague-Dawley rats were sacrificed. The implants were exposed and subsequently analyzed. The results are illustrated in FIG. 6. While the uncoated implants showed capsular fibrosis (see FIGS. 6A and B), the capsular fibrosis in the silk protein coated implants was strongly reduced (see FIG. 6C). This results in less scarring tissue being formed at the interface of the implant and the host tissue, as evident by a 30% reduction of the scarring tissue forming the implant capsule compared to the control group (see FIG. 7). Further, the capsules of the silk protein coated implants were thinner (see FIG. 6C) in contrast to the capsules of the uncoated implants (see FIG. 6A).

These data allow the conclusion that wounds which are glued with self-assembling proteins, particularly silk proteins, exhibit reduced or no scarring and/or reduced or no fibrosis, particularly capsular fibrosis.

6. Safety Tests 6.1 Acute Eye Irritation Test

The acute eye irritation test was performed according to DIN EN ISO 1093-1 und GLP conditions. Particularly, 0.3 mg spider silk protein eADF4 ($C_{16}$) dissolved in 100 μl phosphate-buffered saline was applied to one of the two eyes of three female New Zealand white rabbits. The non-treated eye of each female New Zealand white rabbit was taken as a control. This treatment did not cause any signs of pain and did not result in any clinical findings. It showed neither eye damage (a risk of serious damage to the eyes could be excluded according to GHS H 318 (Global Harmonizing System)) nor eye irritation (eADF4 ($C_{16}$) was not classified as irritant according to GHS H 319).

6.2 Immunogenicity Test

A composition of eADF4 ($C_{16}$) was administered subcutaneously to five female BALB/c mice at final doses of 2, 10 and 50 μg, respectively. One week before and two, five and eight weeks after administration, sera were harvested and analyzed for the presence of antibodies directed against the test substances. The entire group of five mice showed no significant specific antibody formation (see FIG. 8).

6.3 Acute Systemic Toxicity Test

The Acute systemic toxicity test was performed according to DIN EN ISO 10993-11 under GLP conditions. Particularly, eADF4 ($C_{16}$) was given once i.p. at a dose of 250 mg/kg to female NMRI mice. Two groups of five female mice each were tested, one with the test item dissolved in phosphate-buffered saline, one with the vehicle. No test item group animal showed any clinical findings at the end of the observation period. There was no significant change of body weight. No further findings, such as macroscopic findings or change of organ weights were noted during the observation period.

6.4 Acute Skin Irritability Test

The acute skin irritability test was performed according to OECD 404 guidelines und GLP conditions. Particularly, an ADF4 ($C_{16}$) film patch of 42.5 mg and 6 cm² area was moistened with 100 µl saline, applied to previously shaved skin on the backs of each of three male New Zealand white rabbits, and fixated with sterile gauze pads and hypoallergic plaster. After four hours incubation the film patches were removed and the treated skin was examined. The treatment with a eADF4 ($C_{16}$) film did not cause any erythema formation or edema formation directly after the application or during the observation period. No general clinical findings and no initial pain reaction were observed after administration.

The invention claimed is:

1. An implant uniformly coated with a spider silk polypeptide by dipping or immersing the implant into a liquid composition consisting essentially of the spider silk polypeptide and a solvent or by spraying a liquid aerosol consisting essentially of the spider silk polypeptide and a solvent onto the implant, before subsequently drying the implant.

2. The implant of claim 1, wherein the implant is a soft tissue implant.

3. The implant of claim 2, wherein the soft tissue implant is a silicone implant or an implant with a silicone surface.

4. The implant of claim 1, wherein the silk polypeptide is a recombinant silk polypeptide.

5. A method for uniformly coating an implant with a spider silk polypeptide comprising the step of dipping or immersing the implant into a liquid composition consisting essentially of the spider polypeptide and a solvent, or spraying a liquid aerosol consisting essentially of the spider polypeptide and a solvent onto the implant, before subsequently drying the implant, thereby uniformly coating the implant.

6. The implant of claim 2, wherein the soft tissue implant is a breast implant.

7. An implant uniformly coated with a spider silk polypeptide film by dipping or immersing the implant into a liquid composition consisting essentially of the spider silk polypeptide and a solvent or by spraying a liquid aerosol consisting essentially of the spider silk polypeptide and a solvent onto the implant, before subsequently drying the implant.

8. An implant coated with a spider silk polypeptide film by the method of claim 5.

* * * * *